US009765347B2

(12) United States Patent
Kobayashi et al.

(10) Patent No.: US 9,765,347 B2
(45) Date of Patent: Sep. 19, 2017

(54) **TRANSFORMANT OF *SCHIZOSACCHAROMYCES POMBE* MUTANT AND CLONING VECTOR**

(71) Applicant: Asahi Glass Company, Limited, Tokyo (JP)

(72) Inventors: Mayumi Kobayashi, Tokyo (JP); Hideki Tohda, Tokyo (JP); Shuichiro Kimura, Tokyo (JP); Susumu Zen-In, Tokyo (JP); Futoshi Hara, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 14/627,459

(22) Filed: Feb. 20, 2015

(65) Prior Publication Data

US 2015/0240250 A1    Aug. 27, 2015

Related U.S. Application Data

(63) Continuation of application No. PCT/JP2013/072195, filed on Aug. 20, 2013.

(30) Foreign Application Priority Data

Aug. 20, 2012 (JP) ................................. 2012-181865

(51) Int. Cl.
*C12N 15/81* (2006.01)
*C12N 9/42* (2006.01)

(52) U.S. Cl.
CPC ......... *C12N 15/815* (2013.01); *C12N 9/2445* (2013.01)

(58) Field of Classification Search
None
See application file for complete search history.

(56) References Cited

U.S. PATENT DOCUMENTS 7,790,450 B2 * 9/2010 Fujita .................. C12N 15/815
435/320.1

FOREIGN PATENT DOCUMENTS

| JP | 5-15380 | A | 1/1993 |
| JP | 7-163373 | A | 6/1995 |
| JP | 2776085 | B2 | 5/1998 |
| JP | 10-234375 | A | 9/1998 |
| JP | 11-192094 | A | 7/1999 |
| JP | 2000-106867 | A | 4/2000 |
| JP | 2000-136199 | A | 5/2000 |
| JP | 2000-262284 | A | 9/2000 |
| WO | 96/23890 | A1 | 8/1996 |
| WO | 99/23223 | A1 | 5/1999 |
| WO | 2007/026617 | A1 | 3/2007 |
| WO | 2012/060389 | A1 | 5/2012 |
| WO | 2012/128260 | A1 | 9/2012 |

OTHER PUBLICATIONS

Orlandi et al. (1996) Cloning, sequencing and regulation of a cDNA encoding a small heat-shock protein from *Schizosaccharomyces pombe*. Biochimica et Biophysica Acta, 1307:129-131.*
CU329670.1 (*Schizosaccharomyces pombe* chromosome I, GenBank Accession, GI: 159883886, priority to Jul. 28, 2009, Region: 5320402 . . . 5321005), 3 pages.*
CU329670.1 (*Schizosaccharomyces pombe* chromosome I, GenBank Accession, GI: 159883886, priority to Jul. 28, 2009, Region: 755080 . . . 756003), 3 pages.*
SPAC22G7.11c PomBase entry (accessed from <https://www.pombase.org/spombe/result/SPAC22G7.11c> on Jun. 24, 2016), 6 pages.*
Wray et al. (2007) The evolutionary significance of cis-regulatory mutations. Nature, 8:206-216.*
Takada et al.—Expression of *Aspergillus aculeatus* No. F-50 Cellobiohydrolase I (cbhI) and β-glucosidase 1 (bgl1) genes by *Saccharomyces cerevisiae* Biosci. Biotechnol. Biochem., 62(8), pp. 1615-1618, 1998.
Giga-Hama et al.—"Foreign Gene Expression in Fission Yeast *Schizosaccharomyces pombe*", Springer-Verlag and Landes Bioscience, pp. 1-28, 1997.
Tomohiko Matsuzawa, et al., "Identification of a galactose-specific flocculin essential for non-sexual flocculation and filamentous growth in *Schizosaccharomyces pombe*" Molecular Microbiology, vol. 82, No. 6, 2011, pp. 1531-1544.
Tomohiko Matsuzawa, et al., "MADS Box Transcription Factor Mbx2/Pvg4 Regulates Invasive Growth and Flocculation by Inducing gsf2* Expression in Fission Yeast", Eukaryotic Cell, vol. 11, No. 2, XP-002751459, Feb. 2012, pp. 151-158.
Tomohiko Matsuzawa, et al., "Galactose-Specific Recognition System in the Fission Yeast *Schizosaccharomyces pombe*", Trends in Glycoscience and Glycotechnology, vol. 24, No. 135, XP-002751460, Jan. 2012, pp. 24-42.
Caroline Wilde, et al., "Expression of a library of fungal β-glucosidases in *Saccharomyces cerevisiae* for the development of a biomass fermenting strain", Applied Microbiology and Biotechnology, vol. 95, No. 3, XP035084638, ISSN: 1432-0614, Jan. 5, 2012, pp. 647-659.

(Continued)

*Primary Examiner* — Neil P Hammell
(74) *Attorney, Agent, or Firm* — Oblon, McClelland, Maier & Neustadt, L.L.P.

(57) ABSTRACT

Provided is a transformant of *S. pombe* mutant which can produce and collect β-glucosidase without requiring complicated separation steps, and a vector which is useful for transforming a yeast of the genus *Schizosaccharomyces*. The transformant of a *S. pombe* mutant of the present invention is a transformant of a *Schizosaccharomyces pombe* mutant which exhibits an increased Gsf activity and decreased or no pyruvyl transferase Pvg1 enzymatic activity, and is comprised of a structural gene sequence encoding a β-glucosidase derived from a filamentous fungus, and a promoter sequence and a terminator sequence for expressing the structural gene in a chromosome or as an extrachromosomal gene. Further, the present invention relates to a cloning vector which is characterized by comprising a hsp9 gene promoter or an ihc1 gene promoter of a yeast of the genus *Schizosaccharomyces*, and is useful for transforming a yeast of the genus *Schizosaccharomyces*, an expression vector, a transformant, etc.

6 Claims, 15 Drawing Sheets

(56) References Cited

OTHER PUBLICATIONS

Nassapat Boonvitthya, et al., "Cloning and expression of the *Aspergillus wyzae* glucan 1,3-beta-glucosidase A (exgA) in Pichia pastoris", Biotechnology Letters, vol. 34, No. 10, XP035131438, ISSN: 1573-6776, Jul. 11, 2012, pp. 1937-1943.

A. P. Njokvveni, et al., "Fungal β-glucosidase expression in *Saccharomyces cerevisiae*", Journal of Industrial Microbiology & Biotechnology, vol. 39, No. 10, XP009190363, ISSN: 1476-5535, Jun. 16, 2012, pp. 1445-1452.

M.I. Rajoka, et al., "Cloning and Expression of (β-Glucosidase Genes in *Escherichia coli* and *Saccharomyces cerevisiae* Using Shuttle Vector pYES 2.0", Folia Microbiologica, vol. 43, No. 2, XP009190366, ISSN: 0015-5632, 1998, pp. 129-135.

Jiwon Ahn, et al. "Small heat-shock protein Hsp9 has dual functions in stress adaptation and stress-induced G2-M checkpoint regulation via Cdc25 inactivation in *Schizosaccharomyces pombe*", Biochemical and Biophysical Research Communications, vol. 417, 2012, pp. 613-618.

\* cited by examiner

SEQUENCE LISTING

<160> NUMBER OF SEQ ID NOS: 20

<210> SEQ ID NO 1
<211> LENGTH: 841
<212> TYPE: PRT
<213> ORGANISM: Aspergillus aculeatus

<400> SEQUENCE: 1

```
Asp Glu Leu Ala Phe Ser Pro Pro Phe Tyr Pro Ser Pro Trp Ala Asn
 1               5                  10                  15

Gly Gln Gly Glu Trp Ala Glu Ala Tyr Gln Arg Ala Val Ala Ile Val
            20                  25                  30

Ser Gln Met Thr Leu Asp Glu Lys Val Asn Leu Thr Thr Gly Thr Gly
        35                  40                  45

Trp Glu Leu Glu Lys Cys Val Gly Gln Thr Gly Gly Val Pro Arg Leu
    50                  55                  60

Asn Ile Gly Gly Met Cys Leu Gln Asp Ser Pro Leu Gly Ile Arg Asp
65                  70                  75                  80

Ser Asp Tyr Asn Ser Ala Phe Pro Ala Gly Val Asn Val Ala Ala Thr
                85                  90                  95

Trp Asp Lys Asn Leu Ala Tyr Leu Arg Gly Gln Ala Met Gly Gln Glu
            100                 105                 110

Phe Ser Asp Lys Gly Ile Asp Val Gln Leu Gly Pro Ala Ala Gly Pro
        115                 120                 125

Leu Gly Arg Ser Pro Asp Gly Gly Arg Asn Trp Glu Gly Phe Ser Pro
    130                 135                 140

Asp Pro Ala Leu Thr Gly Val Leu Phe Ala Glu Thr Ile Lys Gly Ile
145                 150                 155                 160

Gln Asp Ala Gly Val Val Ala Thr Ala Lys His Tyr Ile Leu Asn Glu
                165                 170                 175

Gln Glu His Phe Arg Gln Val Ala Glu Ala Ala Gly Tyr Gly Phe Asn
            180                 185                 190

Ile Ser Asp Thr Ile Ser Ser Asn Val Asp Asp Lys Thr Ile His Glu
        195                 200                 205

Met Tyr Leu Trp Pro Phe Ala Asp Ala Val Arg Ala Gly Val Gly Ala
    210                 215                 220

Ile Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Gly Ala His His Ser Gly Val Gly Ser Ala
            260                 265                 270

Leu Ala Gly Leu Asp Met Ser Met Pro Gly Asp Ile Thr Phe Asp Ser
        275                 280                 285

Ala Thr Ser Phe Trp Gly Thr Asn Leu Thr Ile Ala Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Tyr Gln Pro Pro Asn Phe
                325                 330                 335

Ser Ser Trp Thr Arg Asp Glu Tyr Gly Phe Lys Tyr Phe Tyr Pro Gln
            340                 345                 350

Glu Gly Pro Tyr Glu Lys Val Asn His Phe Val Asn Val Gln Arg Asn
        355                 360                 365
```

His Ser Glu Val Ile Arg Lys Leu Gly Ala Asp Ser Thr Val Leu Leu
370             375                 380

Lys Asn Asn Ala Leu Pro Leu Thr Gly Lys Glu Arg Lys Val Ala
385             390                 395                 400

Ile Leu Gly Glu Asp Ala Gly Ser Asn Ser Tyr Gly Ala Asn Gly Cys
                405                 410                 415

Ser Asp Arg Gly Cys Asp Asn Gly Thr Leu Ala Met Ala Trp Gly Ser
            420                 425                 430

Gly Thr Ala Glu Phe Pro Tyr Leu Val Thr Pro Gln Ala Ile Gln
            435                 440                 445

Ala Glu Val Leu Lys His Lys Gly Ser Val Tyr Ala Ile Thr Asp Asn
450                 455                 460

Trp Ala Leu Ser Gln Val Glu Thr Leu Ala Lys Gln Ala Ser Val Ser
465                 470                 475                 480

Leu Val Phe Val Asn Ser Asp Ala Gly Glu Gly Tyr Ile Ser Val Asp
                485                 490                 495

Gly Asn Glu Gly Asp Arg Asn Asn Leu Thr Leu Trp Lys Asn Gly Asp
            500                 505                 510

Asn Leu Ile Lys Ala Ala Ala Asn Asn Cys Asn Asn Thr Ile Val Val
                515                 520                 525

Ile His Ser Val Gly Pro Val Leu Val Asp Glu Trp Tyr Asp His Pro
530                 535                 540

Asn Val Thr Ala Ile Leu Trp Ala Gly Leu Pro Gly Gln Glu Ser Gly
545                 550                 555                 560

Asn Ser Leu Ala Asp Val Leu Tyr Gly Arg Val Asn Pro Gly Ala Lys
                565                 570                 575

Ser Pro Phe Thr Trp Gly Lys Thr Arg Glu Ala Tyr Gly Asp Tyr Leu
            580                 585                 590

Val Arg Glu Leu Asn Asn Gly Asn Gly Ala Pro Gln Asp Asp Phe Ser
            595                 600                 605

Glu Gly Val Phe Ile Asp Tyr Arg Gly Phe Asp Lys Arg Asn Glu Thr
610                 615                 620

Pro Ile Tyr Glu Phe Gly His Gly Leu Ser Tyr Thr Thr Phe Asn Tyr
625                 630                 635                 640

Ser Gly Leu His Ile Gln Val Leu Asn Ala Ser Ser Asn Ala Gln Val
                645                 650                 655

Ala Thr Glu Thr Gly Ala Ala Pro Thr Phe Gly Gln Val Gly Asn Ala
            660                 665                 670

Ser Asp Tyr Val Tyr Pro Glu Gly Leu Thr Arg Ile Ser Lys Phe Ile
            675                 680                 685

Tyr Pro Trp Leu Asn Ser Thr Asp Leu Lys Ala Ser Ser Gly Asp Pro
690                 695                 700

Tyr Tyr Gly Val Asp Thr Ala Glu His Val Pro Glu Gly Ala Thr Asp
705                 710                 715                 720

Gly Ser Pro Gln Pro Val Leu Pro Ala Gly Gly Ser Gly Gly Asn
            725                 730                 735

Pro Arg Leu Tyr Asp Glu Leu Ile Arg Val Ser Val Thr Val Lys Asn
            740                 745                 750

Thr Gly Arg Val Ala Gly Asp Ala Val Pro Gln Leu Tyr Val Ser Leu
            755                 760                 765

Gly Gly Pro Asn Glu Pro Lys Val Val Leu Arg Lys Phe Asp Arg Leu
770                 775                 780

Thr Leu Lys Pro Ser Glu Glu Thr Val Trp Thr Thr Thr Leu Thr Arg

```
                785                 790                 795                 800
Arg Asp Leu Ser Asn Trp Asp Val Ala Ala Gln Asp Trp Val Ile Thr
                    805                 810                 815
Ser Tyr Pro Lys Lys Val His Val Gly Ser Ser Arg Gln Leu Pro
                820                 825                 830
Leu His Ala Ala Leu Pro Lys Val Gln
                835                 840

<210> SEQ ID NO 2
<211> LENGTH: 2664
<212> TYPE: DNA
<213> ORGANISM: Artificial Sequence
<220> FEATURE:
<223> OTHER INFORMATION: Description of Artificial Sequence: modified
      AaBGL1 gene

<400> SEQUENCE: 2
cgaattggcg gaaggccgtc aaggccgcat ggtacctcat gaagttgtcc tggcttgagg      60
ccgctgccct taccgccgcc tccgtcgttt ccgccgacga gttggccttc tcccccccct     120
tctaccccct ccctgggcc aacggtcaag gtgagtgggc cgaggcttac aacgtgccg      180 tcgccattgt ctcccaaatg acccttgacg agaaggtcaa ccttaccacc ggtactggtt     240
gggagcttga agtgcgtc ggtcaaaccg gtggtgtccc ccgtcttaac atcggtggta      300
tgtgccttca agactccccc cttggtatcc gtgactccga ctacaactcc gccttccctg     360
ccggtgtcaa cgtcgccgcc acctgggaca gaaaccttgc ctaccttcgt ggtcaagcta     420
tgggtcaaga gttctccgac aagggtatcg acgtccaact tggtcctgcc gccggtcccc     480
ttggtcgttc ccccgacggt ggtcgtaact gggagggttt ctcccccgac cccgccctta     540
ccggtgtcct tttcgccgag actatcaagg gtatccaaga cgctggtgtc gtcgccaccg     600
ccaagcacta catccttaac gagcaagagc acttccgtca agtcgccgag ccgctggtt     660 acggtttcaa catctccgac accatctctt ccaacgttga cgacaagacc atccacgaga     720 tgtaccttg ccccttcgcc gacgccgtcc gtgccggtgt cggtgccatc atgtgctcct     780
acaaccaaat caacaactcc tacggttgcc aaaactccta cacccttaac aagttgttga     840
aggccgagct tggttttccaa ggtttcgtca tgtccgactg gggtgcccac cactccggtg     900
ttggttccgc ccttgccggt cttgacatgt ccatgcccgg tgacatcacc ttcgactccg     960
ctacctcctt ctggggcacc aaccttacca ttgccgtcct aacggtact gtcccccaat    1020 ggcgtgttga cgacatggcc gtccgtatca tggccgccta ctacaaggtc ggtcgtgacc    1080
gtctttacca accccccaac ttctcctcct ggacccgtga cgagtacggt ttcaagtact    1140 tctacccca gagggtcccc tacgagaagg ttaaccactt cgtcaacgtc aacgtaacc    1200 actccgaggt catccgtaag ttgggtgccg actccaccgt ccttttgaag aacaacaacg    1260
ccttgccctt gaccggtaag gagcgtaagg tcgccatcct ggtgaggac gccggttcca    1320 actcttacgg tgccaacggt tgctccgacc gtggttgcga caacggtact cttgctatgg    1380
cctggggttc cggtactgcc gagttccccc accttgtcac ccccgagcaa gccatccaag    1440
ccgaggtctt gaagcacaag ggttccgtct acgccatcac cgacaactgg gccttgtccc    1500
aagtcgagac tcttgccaag caagcctctg tctcccttgt tttcgtcaac tccgacgccg    1560
gtgagggtta catctccgtt gacggtaacg agggtgaccg taacaacctt acccttggga    1620 agaacgtga caaccttatc aaggccgctg ccaacaactg caacaacacc atcgtcgtca    1680
tccactccgt cggtcccgtc cttgttgacg agtggtacga ccacccaac gtcaccgcca    1740
```

```
tcctttgggc cggtttgccc ggtcaagagt ccggtaactc ccttgccgac gtcctttacg    1800
gtcgtgtcaa ccccggtgcc aagtccccct tcacctgggg taagacccgt gaggcttacg    1860
gtgactacct tgtccgtgag cttaacaacg gtaacggtgc cccccaagac gacttctccg    1920
agggtgtttt catcgactac cgtggtttcg acaagcgtaa cgagactccc atctacgagt    1980
tcggtcacgg tttgtcctac accaccttca actactccgg tctccacatc caagtcctta    2040
acgcctcctc caacgcccaa gtcgccaccg agactggtgc cgcccctacc ttcggtcaag    2100
tcggtaacgc ctccgactac gtctaccccg agggtcttac ccgtatctcc aagttcatct    2160
accccctggc taactctacc gacttgaagg cttcctccgg tgaccctac tacggtgttg     2220 acaccgccga gcacgtcccc gagggtgcca ccgacggttc cccccaaccc gtccttcccg    2280
ctggtggtgg ttccggtggt aaccctcgtc tttacgacga gcttatccgt gtctccgtca    2340
ccgtcaagaa caccggtcgt gtcgccggtg acgccgtccc ccaactttac gtttcccttg    2400
gtggtcccaa cgagcccaag gtcgtccttc gtaagttcga ccgtcttacc ttgaagccct    2460
ccgaggagac tgtctggacc accacccta cccgtcgtga ccttcccaac tgggacgtcg     2520
ccgcccaaga ctgggtcatc acctcctacc ccaagaaggt ccacgtcggt tcctcttccc    2580
gtcaacttcc ccttcacgcc gcccttccca aggtccaatg ataatctaga gctcctgggc    2640
ctcatgggcc ttccgctcac tgcc                                          2664

<210> SEQ ID NO 3
<211> LENGTH: 8515
<212> TYPE: DNA
<213> ORGANISM: Artificial Sequence
<220> FEATURE:
<223> OTHER INFORMATION: Description of Artificial Sequence: pSL6AaBGL1

<400> SEQUENCE: 3
cgtacgattt aaatgcggcc gcttcggctg cggcgagcgg gtatcagctc actcaaaggc     60
ggtaatacgg ttatccacag aatcagggga taacgcagga agaacatgt gagcaaaagg     120 ccagcaaaag gccaggaacc gtaaaaaggc cgcgttgctg cgttttttcc ataggctccg    180
cccccctgac gagcatcaca aaaatcgacg ctcaagtcag aggtggcgaa acccgacagg    240
actataaaga taccaggcgt ttccccctgg aagctccctc gtgcgctctc ctgttccgac    300
cctgccgctt accggatacc tgtccgcctt tctcccttcg ggaagcgtgg cgctttctca    360
atgctcacgc tgtaggtatc tcagttcggt gtaggtcgtt cgctccaagc tgggctgtgt    420
gcacgaaccc ccgttcagcc cgaccgctg cgccttatcc ggtaactatc gtcttgagtc     480
caacccggta agacacgact tatcgccact ggcagcagcc actggtaaca ggattagcag    540
agcgaggtat gtaggcggtg ctacagagtt cttgaagtgg tggcctaact acggctacac    600
tagaaggaca gtatttggta tctgcgctct gctgaagcca gttaccttcg gaaaaagagt    660
tggtagctct tgatccggca acaaaccac cgctggtagc ggtggttttt ttgtttgcaa     720
gcagcagatt acgcgcagaa aaaaggatc tcaagaagat cctttgatct tttctacggg    780
gtctgacgct cagtggaacg aaaactcacg ttaagggatt ttggtcatga gcttgcgccg    840
tcccgtcaag tcagcgtaat gctctgccag tgttacaacc aattaaccaa ttctgattag    900
aaaaactcat cgagcatcaa atgaaactgc aatttattca tatcaggatt atcaatacca    960
tatttttgaa aaagccgttt ctgtaatgaa ggagaaaact caccgaggca gttccatagg    1020
atggcaagat cctggtatcg gtctgcgatt ccgactcgtc caacatcaat acaacctatt    1080
```

```
aatttcccct cgtcaaaaat aaggttatca agtgagaaat caccatgagt gacgactgaa    1140
tccggtgaga atggcaagag cttatgcatt tctttccaga cttgttcaac aggccagcca    1200
ttacgctcgt catcaaaatc actcgcatca accaaaccgt tattcattcg tgattgcgcc    1260
tgagcgaggc gaaatacgcg atcgctgtta aaggacaat  tacaaacagg aatcgaatgc    1320
aaccggcgca ggaacactgc cagcgcatca acaatatttt cacctgaatc aggatattct    1380
tctaatacct ggaatgctgt tttcccaggg atcgcagtgg tgagtaacca tgcatcatca    1440
ggagtacgga taaaatgctt gatggtcgga agaggcataa attccgtcag ccagtttagt    1500
ctgaccatct catctgtaac atcattggca acgctacctt tgccatgttt cagaaacaac    1560
tctggcgcat cgggcttccc atacaatcgg tagattgtcg cacctgattg cccgacatta    1620
tcgcgagccc atttataccc atataaatca gcatccatgt tggaatttaa tcgcggcctc    1680
gtcgagcaag acgtttcccg ttgaatatgg ctcataacac cccttgtatt actgtttatg    1740
taagcagaca gttttattgt tcatttaaat gcggccgcgt acggcggctt cgatagcttc    1800
agcctcctta ggagcattca aaccataacg aaggagaagg gaagcagata aaattgtacc    1860
aacaggatta acaatgccct tgccagcgat atcgggagcg ctaccgtgaa tgggctcaac    1920
caaacaatga accttttctt ctgattttcc taccacaccg gaaagggagg cagaaggcaa    1980
aaggcccaag ctaccaggaa tgacagaagc ctcatctgaa ataatgtcac caaacaagtt    2040
gtcagtcaaa caacaccgt  taagtgtacg agggctcttg accaaaagca tggctgcgga    2100
gtcaatgagc tggttttta  aggtaaggtg aggatattcc tccttaaaaa tcttagctac    2160
agtcttgcgc caaagacgag aagttgccaa acattagct  ttgtcgagta atgtgacggg    2220
agcaggaggg ttggaagttt cagctaacca agcagccaaa cgagcaatac gagaaacttc    2280
ttccaaactg taaggccaag tgtccatagc ataacccgat ccgttgtcct cagtgcgctc    2340
accaaagtaa caacctccag taagttctcg tacaacacaa aaatcgacac cttcaacgat    2400
ttcaggcttc aaagggctgt acttgactaa agacttgctg gcaaagttgc aaggtcgaag    2460
gttggcccaa acacccatac tcttacgaag cttcaataaa ccttgctcag gacgacaatt    2520
ggggttggtc cattcaggac caccaacggc acccaaaaga acaccgtcag cttccaaaca    2580
agccttcaca gtctcgtcag tcaaaggggt tccataggca tcaatagagg cacctccaat    2640
cttgtgttct tcaaactcga gttttaactc aggtcgcttc ttctcaacga cttcaaaac    2700 ctccaaggca gaagcaacaa tttcagggcc aatatggtct cctggtaaga cgacgatttt    2760
ctttgcacac atgttgttga agaagttttg ttgtgaaatg gtttcgtgaa agtttcagac    2820
cctaccgcaa aaatgcctgg tttcgggaaa ctcaacactg ttgcactttt tatactacag    2880
attgggatat cgtaatatt  gcgtaaaaaa tcctttttt  aaaaagcttg tttacagtaa    2940
cgtaaatgac cagaaatcag atgaaaatca caagaaagca ataattcac  gttaaatcct    3000 gatatgtttg attttgtgat gaaatcatgg atgttcatag gaattgttga aattgcgctt    3060
ttttaacgaa atatacaagt atcctggagc ttacttaatt aattaatgaa tctttgttcc    3120
taggcccggg ctagtaatca attacggggt cattagttca tagcccatat atggagttcc    3180
gcgttacata acttacggta aatggcccgc ctggctgacc gcccaacgac cccgcccat    3240 tgacgtcaat aatgacgtat gttcccatag taacgccaat agggactttc cattgacgtc    3300
aatgggtgga gtatttacgg taaactgccc acttggcagt acatcaagtg tatcatatgc    3360
caagtacgcc ccctattgac gtcaatgacg gtaaatggcc cgcctggcat ttgcccagt     3420 acatgacctt atgggacttt cctacttggc agtacatcta cgtattagtc atcgctatta    3480
```

```
ccatggtgat gcggttttgg cagtacatca atgggcgtgg atagcggttt gactcacggg    3540
gatttccaag tctccacccc attgacgtca atggagttt gttttggcac caaaatcaac    3600
gggactttcc aaaatgtcgt aacaactccg ccccattgac gcaaatgggc ggtaggcgtg    3660
tacggtggga ggtctatata agcagatttc tctttagttc tttgcaagaa ggtagagata    3720
aagacacttt ttcaaacatg aagttgtcct ggcttgaggc cgctgccctt accgccgcct    3780
ccgtcgtttc cgccgacgag ttggccttct cccccccctt ctacccctcc cctgggcca    3840 acggtcaagg tgagtgggcc gaggcttacc aacgtgccgt cgccattgtc tcccaaatga    3900
cccttgacga aaggtcaac cttaccaccg gtactggttg ggagcttgag aagtgcgtcg    3960
gtcaaaccgg tggtgtcccc cgtcttaaca tcggtggtat gtgccttcaa gactcccccc    4020
ttggtatccg tgactccgac tacaactccg ccttccctgc cggtgtcaac gtcgccgcca    4080
cctgggacaa gaaccttgcc taccttcgtg gtcaagctat gggtcaagag ttctccgaca    4140
agggtatcga cgtccaactt ggtcctgccg ccggtccct tggtcgttcc cccgacggtg    4200
gtcgtaactg ggagggtttc tcccccgacc ccgcccttac cggtgtcctt ttcgccgaga    4260
ctatcaaggg tatccaagac gctggtgtcg tcgccaccgc caagcactac atccttaacg    4320
agcaagagca cttccgtcaa gtcgccgagg ccgctggtta cggtttcaac atctccgaca    4380
ccatctcttc caacgttgac gacaagacca tccacgagat gtacctttgg cccttcgccg    4440
acgccgtccg tgccggtgtc ggtgccatca tgtgctccta caaccaaatc aacaactcct    4500
acggttgcca aaactcctac acccttaaca agttgttgaa ggccgagctt ggtttccaag    4560
gtttcgtcat gtccgactgg ggtgcccacc actccggtgt tggttccgcc cttgccggtc    4620
ttgacatgtc catgcccggt gacatcacct tcgactccgc tacctccttc tggggcacca    4680
accttaccat tgccgtcctt aacggtactg tcccccaatg gcgtgttgac gacatggccg    4740
tccgtatcat ggccgcctac tacaaggtcg gtcgtgaccg tctttaccaa cccccccaact    4800 tctcctcctg gacccgtgac gagtacggtt tcaagtactt ctaccccccaa gagggtccct    4860 acgagaaggt taaccacttc gtcaacgtcc aacgtaacca ctccgaggtc atccgtaagt    4920
tgggtgccga ctccaccgtc cttttgaaga caacaacgc cttgcccttg accggtaagg    4980
agcgtaaggt cgccatcctt ggtgaggacg ccggttccaa ctcttacggt gccaacggtt    5040
gctccgaccg tggttgcgac aacggtactc ttgctatggc ctggggttcc ggtactgccg    5100
agttccccta ccttgtcacc cccgagcaag ccatccaagc cgaggtcttg aagcacaagg    5160
gttccgtcta cgccatcacc gacaactggg ccttgtccca gtcgagact cttgccaagc    5220 aagcctctgt ctcccttgtt ttcgtcaact ccgacgccgg tgagggttac atctccgttg    5280
acggtaacga gggtgaccgt aacaaccta ccctttggaa gaacggtgac aaccttatca    5340
aggccgctgc caacaactgc aacaacacca tcgtcgtcat ccactccgtc ggtcccgtcc    5400
ttgttgacga gtggtacgac caccccaacg tcaccgccat cctttgggcc ggtttgcccg    5460
gtcaagagtc cggtaactcc cttgccgacg tccttacgg tcgtgtcaac cccggtgcca    5520
agtccccctt cacctggggt aagacccgtg aggcttacgg tgactacctt gtccgtgagc    5580
ttaacaacgg taacggtgcc ccccaagacg acttctccga gggtgttttc atcgactacc    5640
gtggtttcga caagcgtaac gagactccca tctacgagtt cggtcacggt ttgtcctaca    5700
ccaccttcaa ctactccggt ctccacatcc aagtccttaa cgcctcctcc aacgcccaag    5760
tcgccaccga gactggtgcc gcccctacct tcggtcaagt cggtaacgcc tccgactacg    5820
```

```
tctaccccga gggtcttacc cgtatctcca agttcatcta ccctggctt aactctaccg      5880 acttgaaggc ttcctccggt gaccctact acggtgttga caccgccgag cacgtccccg     5940
agggtgccac cgacggttcc ccccaacccg tccttcccgc tggtggtggt tccggtggta     6000
accctcgtct ttacgacgag cttatccgtg tctccgtcac cgtcaagaac accggtcgtg     6060
tcgccggtga cgccgtcccc caactttacg tttcccttgg tggtcccaac gagcccaagg     6120
tcgtccttcg taagttcgac cgtcttacct tgaagccctc cgaggagact gtctggacca     6180 ccaccccttac ccgtcgtgac ctttccaact gggacgtcgc cgcccaagac tgggtcatca    6240
cctcctaccc caagaaggtc cacgtcggtt cctcttcccg tcaacttccc cttcacgccg     6300
cccttcccaa ggtccaatga taatctagag tcgacctgca ggcatgcaag cttaaatagg     6360
aaagtttctt caacaggatt acagtgtagc tacctacatg ctgaaaaata tagccttttaa   6420 atcatttta tattataact ctgtataata gagataagtc cattttttaa aaatgttttc      6480
cccaaaccat aaaaccctat acaagttgtt ctagtaacaa tacatgagaa agatgtctat     6540
gtagctgaaa ataaaatgac gtcacaagac gatctgcctc gcgcgtttcg gtgatgacgg     6600
tgaaaacctc tgacacatgc agctcccgga gacggtcaca gcttgtctgt aagcggatgc     6660
cgggagcaga caagcccgtc agggcgcgtc agcgggtgtt ggcgggtgtc ggggcgcagc     6720
catgacccag tcacgtagcg atagcggagc ccgggcacta gtgaattcga gtatgtgtac     6780
gagttgtctt taaacccaca gaggtagaat gtatatataa aattaataag ctaagtgtaa     6840
tacttaaaaa atacattaat tggaactcgt atcctaccat ttacaatgtt catccaattt     6900
tttcagattg tactgtaaat agcgtttgaa acaccaaat tttagaagct aatcactctc      6960
atcataatcg tctacatcct catcgttatc gacgataaaa gaatcatctt gcatgctggg     7020
ttcatccatg ctatcaaacg agggatcaac gtaaataggt gttttcactg tagccgctgc     7080
tcttctggtt ggcctctttc taatcggaga atctgaatct tctggtggct ctgcgttagt     7140
cgaactagct tttggagttg aactactacc tggaataata aaatcatcat cgtcatcttc     7200
aggtgattgt ttctttaccg agcttgcttt tttcccttta ttcttcgcag aagccttcgt     7260
ggatgttatg gtgaaggtt tcaaactgct aggcaacaaa tcatcttcat cgtctgaaga     7320
aaatatggta gtagcaactg gtttattagt ctttcttcct cttccagacg ccgaggctgc     7380
tatttttttg acgggttttt tactacctgc gtcttcagag tcaacagatt gacttctttt     7440
tcttgatttt ccactatcac tgctatccaa tcccgggctc ttagatatgc gattttcttc     7500
aactgataag ccatgagagt tatcctctgt cttgacaatg tttatgtcag atgatttctc    7560
aggttctttc gacgctgcga actcaagtaa agtttgttgc tttcgatttg ttgtagatgg     7620
tttggattcg ctgctagctt ctttttttaac agcagtactt gaggaggatc cggcaatagc    7680
cctgggtttc ctagtaccag tggatttacc tcgaggcttc ttttttcgttc gatttacaaa   7740 atctcttgag gattgctctt cttctaacat ttctctctga atatcatcca taaccttatt    7800
ccaagcatgc tcaaatgcat ccaaatcatg aagccacaat tctttaggag tttttttaat    7860
caaagcatcc agttcggcca ttacttcgtc ctttttcttg agaagttcca cataccgttc    7920
ataggtcaaa gaccataaag gcattgaaag aaggtaattg taggcatctg aatcctcgtc    7980
ttgcgaaaca tcaccagatt gttcttcttc agcaagagca ttttcaactt ctaaatcaac    8040
caaatgccct ttctttggtt tactgatagg ttgaaacttc ttttccttca gctccacaat    8100
gagatccttt ttcttctttt ttgaaactac aagctccccc tctataatca tatgaataaa    8160
ccgcgcttga tttgaaaatc tatcaaacct tttttccaat tcattaacca tatgctcttt    8220
```

-continued

```
acgtctctgg tatgtcctta aacgtacttc gtaaaactcg gtcaaaatat cttcaacact    8280
gtcatacttc ttgatccgtc cagatgcatc aaaagcaatc atattactcg ttgcttgagt    8340
acgcgacagt ttaaacttaa cttccaagga ttcatttaat gcttctttca tgccagcttc    8400
ggtaagcgtg acattaaagt gaacatttcc ttcaccgtga tggctttcat agtccacgat    8460
gaatttacga atttttccg taccaacaag accagcctcc agatactcct tcatt          8515
```

<210> SEQ ID NO 4
<211> LENGTH: 8563
<212> TYPE: DNA
<213> ORGANISM: Artificial Sequence
<220> FEATURE:
<223> OTHER INFORMATION: Description of Artificial Sequence:
    pSL6P3AaBGL1

<400> SEQUENCE: 4

```
ctctgccagt gttacaacca attaaccaat tctgattaga aaaactcatc gagcatcaaa      60
tgaaactgca atttattcat atcaggatta tcaataccat atttttgaaa aagccgtttc     120
tgtaatgaag gagaaaactc accgaggcag ttccatagga tggcaagatc ctggtatcgg    180
tctgcgattc cgactcgtcc aacatcaata caacctatta atttccctc gtcaaaaata     240
aggttatcaa gtgagaaatc accatgagtg acgactgaat ccggtgagaa tggcaagagc    300
ttatgcattt ctttccagac ttgttcaaca ggccagccat tacgctcgtc atcaaaatca    360
ctcgcatcaa ccaaaccgtt attcattcgt gattgcgcct gagcgaggcg aaatacgcga    420
tcgctgttaa aaggacaatt acaaacagga tcgaatgca accggcgcag gaacactgcc    480
agcgcatcaa caatattttc acctgaatca ggatattctt ctaatacctg gaatgctgtt    540
ttcccaggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact ctggcgcatc gggcttccca    720
tacaatcggt agattgtcgc acctgattgc ccgacattat cgcgagccca tttataccca    780
tataaatcag catccatgtt ggaatttaat cgcggcctcg tcgagcaaga cgtttcccgt    840
tgaatatggc tcataacacc ccttgtatta ctgtttatgt aagcagacag ttttattgtt    900
catttaaatg cggccgcgta cggcggcttc gatagcttca gcctccttag gagcattcaa    960
accataacga aggagaaggg aagcagataa aattgtacca acaggattaa caatgccctt   1020
gccagcgata tcgggagcgc taccgtgaat gggctcaacc aaacaatgaa ccttttcttc   1080
tgatttcct accacaccgg aaagggaggc agaaggcaaa aggcccaagc taccaggaat   1140
gacagaagcc tcatctgaaa taatgtcacc aaacaagttg tcagtcaaaa caacaccgtt   1200
aagtgtacga gggctcttga ccaaaagcat ggctgcggag tcaatgagct ggttttttaa   1260
ggtaaggtga ggatattcct ccttaaaaat cttagctaca gtcttgcgcc aaagacgaga   1320
agttgccaaa acattagctt tgtcgagtaa tgtgacggga gcaggagggt tggaagtttc   1380
agctaaccaa gcagccaaac gagcaatacg agaaacttct tccaaactgt aaggccaagt   1440
gtccatagca taccccgatc cgttgtcctc agtgcgctca ccaaagtaac aacctccagt   1500
aagttctcgt acaacacaaa aatcgacacc ttcaacgatt tcaggcttca aagggctgta   1560
cttgactaaa gacttgctgg caaagttgca aggtcgaagg ttggcccaaa cacccatact   1620
cttacgaagc ttcaataaac cttgctcagg acgacaattg gggttggtcc attcaggacc   1680
accaacggca cccaaaagaa caccgtcagc ttccaaacaa gccttcacag tctcgtcagt   1740
```

```
caaagggtt  ccataggcat  caatagaggc  acctccaatc  ttgtgttctt  caaactcgag   1800
ttttaactca  ggtcgcttct  tctcaacgac  tttcaaaacc  tccaaggcag  aagcaacaat   1860
ttcagggcca  atatggtctc  ctggtaagac  gacgattttc  tttgcacaca  tgttgttgaa   1920
gaagttttgt  tgtgaaatgg  tttcgtgaaa  gtttcagacc  ctaccgcaaa  aatgcctggt   1980
ttcgggaaac  tcaacactgt  tgcactttt  atactacaga  ttgggatatc  gataatattg   2040
cgtaaaaaat  ccttttttta  aaaagcttgt  ttacagtaac  gtaaatgacc  agaaatcaga   2100
tgaaaatcac  aagaaagcaa  ataattcacg  ttaaatcctg  atatgtttga  ttttgtgatg   2160
aaatcatgga  tgttcatagg  aattgttgaa  attgcgcttt  tttaacgaaa  tatacaagta   2220
tcctggagct  tacttaatta  attaatgaat  ctttgttcct  aggcccgggc  tagtaatcaa   2280
ttacggggtc  attagttcat  agcccatata  tggagttccg  cgttacataa  cttacggtaa   2340
atggcccgcc  tggctgaccg  cccaacgacc  cccgcccatt  gacgtcaata  atgacgtatg   2400
ttcccatagt  aacgccaata  gggactttcc  attgacgtca  atgggtggag  tatttacggt   2460
aaactgccca  cttggcagta  catcaagtgt  atcatatgcc  aagtacgccc  cctattgacg   2520
tcaatgacgg  taaatggccc  gcctggcatt  tgcccagta  catgacctta  tgggactttc   2580
ctacttggca  gtacatctac  gtattagtca  tcgctattac  catggtgatg  cggttttggc   2640
agtacatcaa  tgggcgtgga  tagcggtttg  actcacgggg  atttccaagt  ctccacccca   2700
ttgacgtcaa  tgggagtttg  ttttggcacc  aaaatcaacg  ggactttcca  aaatgtcgta   2760
acaactccgc  cccattgacg  caaatgggcg  gtaggcgtgt  acggtgggag  gtctatataa   2820
gcagatttct  ctttagttct  tgcaagaag  gtagagataa  agacactttt  tcaaacatga   2880
agatcaccgc  tgtcattgcc  cttttattct  cacttgctgc  tgcctcacct  attccagttg   2940
ccgatcctgg  tgtggtttca  gttagcctta  agaagcgtgc  cgacgagttg  gccttctccc   3000
cccccttcta  cccctcccc  tgggccaacg  gtcaaggtga  gtgggccgag  gcttaccaac   3060
gtgccgtcgc  cattgtctcc  caaatgaccc  ttgacgagaa  ggtcaaccttt  accaccggta   3120 ctggttggga  gcttgagaag  tgcgtcggtc  aaaccggtgg  tgtccccgt  cttaacatcg   3180 gtggtatgtg  ccttcaagac  tccccccttg  gtatccgtga  ctccgactac  aactccgcct   3240
tccctgccgg  tgtcaacgtc  gccgccacct  gggacaagaa  ccttgcctac  cttcgtggtc   3300
aagctatggg  tcaagagttc  tccgacaagg  gtatcgacgt  ccaacttggt  cctgccgccg   3360
gtccccttgg  tcgttccccc  gacggtggtc  gtaactggga  gggtttctcc  cccgaccccg   3420
cccttaccgg  tgtcctttc  gccgagacta  tcaagggtat  ccaagacgct  ggtgtcgtcg   3480
ccaccgccaa  gcactacatc  cttaacgagc  aagagcactt  ccgtcaagtc  gccgaggccg   3540
ctggttacgg  tttcaacatc  tccgacacca  tctcttccaa  cgttgacgac  aagaccatcc   3600
acgagatgta  cctttggccc  ttcgccgacg  ccgtccgtgc  cggtgtcggt  gccatcatgt   3660
gctcctacaa  ccaaatcaac  aactcctacg  gttgccaaaa  ctcctacacc  cttaacaagt   3720
tgttgaaggc  cgagcttggt  ttccaaggtt  tcgtcatgtc  cgactggggt  gcccaccact   3780
ccggtgttgg  ttccgccctt  gccggtcttg  acatgtccat  gcccggtgac  atcaccttcg   3840
actccgctac  ctccttctgg  ggcaccaacc  ttaccattgc  cgtccttaac  ggtactgtcc   3900
cccaatggcg  tgttgacgac  atggccgtcc  gtatcatggc  cgcctactac  aaggtcggtc   3960
gtgaccgtct  ttaccaaccc  cccaacttct  cctcctggac  ccgtgacgag  tacggtttca   4020
agtacttcta  cccccaagag  ggtccctacg  agaaggttaa  ccacttcgtc  aacgtccaac   4080
```

```
gtaaccactc cgaggtcatc cgtaagttgg gtgccgactc caccgtcctt ttgaagaaca    4140
acaacgcctt gcccttgacc ggtaaggagc gtaaggtcgc catccttggt gaggacgccg    4200
gttccaactc ttacggtgcc aacggttgct ccgaccgtgg ttgcgacaac ggtactcttg    4260
ctatggcctg gggttccggt actgccgagt tcccctacct tgtcaccccc gagcaagcca    4320
tccaagccga ggtcttgaag cacaagggtt ccgtctacgc catcaccgac aactgggcct    4380
tgtcccaagt cgagactctt gccaagcaag cctctgtctc ccttgttttc gtcaactccg    4440
acgccggtga gggttacatc tccgttgacg gtaacgaggg tgaccgtaac aaccttaccc    4500
tttggaagaa cggtgacaac cttatcaagg ccgctgccaa caactgcaac aacaccatcg    4560
tcgtcatcca ctccgtcggt cccgtccttg ttgacgagtg gtacgaccac cccaacgtca    4620
ccgccatcct ttgggccggt ttgcccggtc aagagtccgg taactccctt gccgacgtcc    4680
tttacggtcg tgtcaacccc ggtgccaagt ccccccttca ctggggtaag acccgtgagg    4740
cttacggtga ctaccttgtc cgtgagctta caacggtaa cggtgccccc caagacgact    4800
tctccgaggg tgttttcatc gactaccgtg gtttcgacaa gcgtaacgag actcccatct    4860
acgagttcgg tcacggtttg tcctacacca ccttcaacta ctccggtctc cacatccaag    4920
tccttaacgc ctcctccaac gcccaagtcg ccaccgagac tggtgccgcc cctaccttcg    4980
gtcaagtcgg taacgcctcc gactacgtct accccgaggg tcttacccgt atctccaagt    5040
tcatctaccc ctggcttaac tctaccgact gaaggcttc ctccggtgac ccctactacg    5100
gtgttgacac cgccgagcac gtccccgagg gtgccaccga cggttccccc caacccgtcc    5160
ttcccgctgg tggtggttcc ggtggtaacc ctcgtcttta cgacgagctt atccgtgtct    5220
ccgtcaccgt caagaacacc ggtcgtgtcg ccggtgacgc cgtcccccaa ctttacgttt    5280 ccccttggtgg tcccaacgag cccaaggtcg tccttcgtaa gttcgaccgt cttaccttga    5340
agccctccga ggagactgtc tggaccacca cccttacccg tcgtgacctt ccaactggg    5400 acgtcgccgc ccaagactgg gtcatcacct cctaccccaa gaaggtccac gtcggttcct    5460
cttcccgtca acttcccctt cacgccgccc ttcccaaggt ccaatgataa tctagagtcg    5520
acctgcaggc atgcaagctt aaataggaaa gtttcttcaa caggattaca gtgtagctac    5580
ctacatgctg aaaaatatag cctttaaatc attttttatat tataactctg tataatagag    5640
ataagtccat tttttaaaaa tgttttcccc aaaccataaa accctataca agttgttcta    5700
gtaacaatac atgagaaaga tgtctatgta gctgaaaata aaatgacgtc acaagacgat    5760
ctgcctcgcg cgtttcggtg atgacggtga aaacctctga cacatgcagc tcccggagac    5820
ggtcacagct tgtctgtaag cggatgccgg gagcagacaa gcccgtcagg gcgcgtcagc    5880
gggtgttggc gggtgtcggg gcgcagccat gacccagtca cgtagcgata gcggagcccg    5940
ggcactagtg aattcgagta tgtgtacgag ttgtcttta acccacagag gtagaatgta    6000
tatataaaat taataagcta agtgtaatac ttaaaaaata cattaattgg aactcgtatc    6060
ctaccattta caatgttcat ccaattttt cagattgtac tgtaaatagc gtttgaaaac    6120
accaaatttt agaagctaat cactctcatc ataatcgtct acatcctcat cgttatcgac    6180
gataaaagaa tcatcttgca tgctgggttc atccatgcta tcaaacgagg gatcaacgta    6240
aataggtgtt ttcactgtag ccgctgctct tctggttggc ctctttctaa tcggagaatc    6300
tgaatcttct ggtggctctg cgttagtcga actagctttt ggagttgaac tactacctgg    6360
aataataaaa tcatcatcgt catcttcagg tgattgtttc tttaccgagc ttgcttttt    6420 ccctttattc ttcgcagaag ccttcgtgga tgttatggtg gaaggtttca aactgctagg    6480
```

```
caacaaatca tcttcatcgt ctgaagaaaa tatggtagta gcaactggtt tattagtctt    6540
tcttcctctt ccagacgccg aggctgctat ttttttgacg ggttttttac tacctgcgtc    6600
ttcagagtca acagattgac ttcttttttct tgattttcca ctatcactgc tatccaatcc    6660
cgggctctta gatatgcgat tttcttcaac tgataagcca tgagagttat cctctgtctt    6720
gacaatgttt atgtcagatg atttctcagg ttctttcgac gctgcgaact caagtaaagt    6780
ttgttgcttt cgatttgttg tagatggttt ggattcgctg ctagcttctt ttttaacagc    6840
agtacttgag gaggatccgg caatagccct gggtttccta gtaccagtgg atttacctcg    6900
aggcttcttt ttcgttcgat ttacaaaatc tcttgaggat tgctcttctt ctaacatttc    6960
tctctgaata tcatccataa ccttattcca agcatgctca aatgcatcca aatcatgaag    7020
ccacaattct ttaggagttt ttttaatcaa agcatccagt tcggccatta cttcgtcctt    7080
tttcttgaga agttccacat accgttcata ggtcaaagac cataaaggca ttgaaagaag    7140
gtaattgtag gcatctgaat cctcgtcttg cgaaacatca ccagattgtt cttcttcagc    7200
aagagcattt tcaacttcta aatcaaccaa atgcccttc tttggtttac tgataggttg    7260
aaacttcttt tccttcagct ccacaatgag atccttttc ttctttttg aaactacaag    7320 ctcccccttct ataatcatat gaataaaccg cgcttgattt gaaaatctat caaacccttt    7380
ttccaattca ttaaccatat gctctttacg tctctggtat gtccttaaac gtacttcgta    7440
aaactcggtc aaaatatctt caacactgtc atacttcttg atccgtccag atgcatcaaa    7500
agcaatcata ttactcgttg cttgagtacg cgacagttta aacttaactt ccaaggattc    7560
atttaatgct tctttcatgc cagcttcggt aagcgtgaca ttaaagtgaa catttccttc    7620
accgtgatgg cttcatagt ccacgatgaa tttacgaatt ttttccgtac caacaagacc    7680
agcctccaga tactccttca ttcgtacgat ttaaatgcgg ccgcttcggc tgcggcgagc    7740
gggtatcagc tcactcaaag gcggtaatac ggttatccac agaatcaggg gataacgcag    7800
gaaagaacat gtgagcaaaa ggccagcaaa aggccaggaa ccgtaaaaag gccgcgttgc    7860
tggcgttttt ccataggctc cgcccccctg acgagcatca caaaaatcga cgctcaagtc    7920
agaggtggcg aaacccgaca ggactataaa gataccaggc gtttccccct ggaagctccc    7980
tcgtgcgctc tcctgttccg accctgccgc ttaccggata cctgtccgcc tttctccctt    8040
cgggaagcgt ggcgctttct caatgctcac gctgtaggta tctcagttcg gtgtaggtcg    8100
ttcgctccaa gctgggctgt gtgcacgaac cccccgttca gcccgaccgc tgcgccttat    8160
ccggtaacta tcgtcttgag tccaacccgg taagacacga cttatcgcca ctggcagcag    8220
ccactggtaa caggattagc agagcgaggt atgtaggcgg tgctacagag ttcttgaagt    8280
ggtggcctaa ctacggctac actagaagga cagtatttgg tatctgcgct ctgctgaagc    8340
cagttacctt cggaaaaaga gttggtagct cttgatccgg caaacaaacc accgctggta    8400
gcggtggttt ttttgtttgc aagcagcaga ttacgcgcag aaaaaaagga tctcaagaag    8460
atcctttgat cttttctacg gggtctgacg ctcagtggaa cgaaaactca cgttaaggga    8520
ttttggtcat gagcttgcgc cgtcccgtca agtcagcgta atg                       8563
```

<210> SEQ ID NO 5
<211> LENGTH: 8550
<212> TYPE: DNA
<213> ORGANISM: Artificial Sequence
<220> FEATURE:
<223> OTHER INFORMATION: Description of Artificial Sequence:
      pSL14P3AaBGL1

<400> SEQUENCE: 5

```
actagtgaat tcgagtatgt gtacgagttg tctttaaacc cacagaggta gaatgtatat    60
ataaaattaa taagctaagt gtaatactta aaaatacat taattggaac tcgtatccta    120
ccatttacaa tgttcatcca attttttcag attgtactgt aaatagcgtt tgaaaacacc    180
aaattttaga agctaatcac tctcatcata atcgtctaca tcctcatcgt tatcgacgat    240
aaaagaatca tcttgcatgc tgggttcatc catgctatca aacgagggat caacgtaaat    300
aggtgttttc actgtagccg ctgctcttct ggttggcctc tttctaatcg gagaatctga    360
atcttctggt ggctctgcgt tagtcgaact agcttttgga gttgaactac tacctggaat    420
aataaaatca tcatcgtcat cttcaggtga ttgtttcttt accgagcttg ctttttttccc    480
tttattcttc gcagaagcct tcgtggatgt tatggtggaa ggtttcaaac tgctaggcaa    540
caaatcatct tcatcgtctg aagaaaatat ggtagtagca actggtttat tagtcttttct    600
tcctcttcca gacgccgagg ctgctatttt tttgacgggt ttttactac ctgcgtcttc    660
agagtcaaca gattgacttc ttttttcttga ttttccacta tcactgctat ccaatcccgg    720
gctcttagat atgcgatttt cttcaactga taagccatga gagttatcct ctgtcttgac    780
aatgtttatg tcagatgatt tctcaggttc tttcgacgct gcgaactcaa gtaaagtttg    840
ttgcttttcga tttgttgtag atggtttgga ttcgctgcta gcttctttttt taacagcagt    900
acttgaggag gatccggcaa tagccctggg tttcctagta ccagtggatt tacctcgagg    960
cttctttttc gttcgattta caaaatctct tgaggattgc tcttcttcta acatttctct    1020
ctgaatatca tccataacct tattccaagc atgctcaaat gcatccaaat catgaagcca    1080
caattcttta ggagtttttt taatcaaagc atccagttcg gccattactt cgtccttttt    1140
cttgagaagt tccacatacc gttcataggt caaagaccat aaaggcattg aaagaaggta    1200
attgtaggca tctgaatcct cgtcttgcga aacatcacca gattgttctt cttcagcaag    1260
agcattttca acttctaaat caaccaaatg cccctttcttt ggtttactga taggttgaaa    1320
cttcttttcc ttcagctcca caatgagatc ctttttcttc ttttttgaaa ctacaagctc    1380
ccccctctata atcatatgaa taaaccgcgc ttgatttgaa aatctatcaa accttttttc    1440
caattcatta accatatgct ctttacgtct ctggtatgtc cttaaacgta cttcgtaaaa    1500
ctcggtcaaa atatcttcaa cactgtcata cttcttgatc cgtccagatg catcaaaagc    1560
aatcatatta ctcgttgctt gagtacgcga cagtttaaac ttaacttcca aggattcatt    1620
taatgcttct ttcatgccag cttcggtaag cgtgacatta aagtgaacat ttccttcacc    1680
gtgatggctt tcatagtcca cgatgaattt acgaattttt tccgtaccaa caagaccagc    1740
ctccagatac tccttcattc gtacgattta aatgcggccg cttcggctgc ggcgagcggg    1800
tatcagctca ctcaaaggcg gtaatacggt tatccacaga atcagggat aacgcaggaa    1860
agaacatgtg agcaaaaggc cagcaaaagg ccaggaaccg taaaaaggcc gcgttgctgg    1920
cgttttttcca taggctccgc ccccctgacg agcatcacaa aaatcgacgc tcaagtcaga    1980
ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcaa tgctcacgct gtaggtatct cagttcggtg taggtcgttc    2160
gctccaagct gggctgtgtg cacgaacccc ccgttcagcc cgaccgctgc gccttatccg    2220
gtaactatcg tcttgagtcc aacccggtaa gacacgactt atcgccactg gcagcagcca    2280
```

```
ctggtaacag gattagcaga gcgaggtatg taggcggtgc tacagagttc ttgaagtggt   2340
ggcctaacta cggctacact agaaggacag tatttggtat ctgcgctctg ctgaagccag   2400
ttaccttcgg aaaaagagtt ggtagctctt gatccggcaa acaaaccacc gctggtagcg   2460
gtggtttttt tgtttgcaag cagcagatta cgcgcagaaa aaaaggatct caagaagatc   2520
ctttgatctt ttctacgggg tctgacgctc agtggaacga aaactcacgt taagggattt   2580
tggtcatgag cttgcgccgt cccgtcaagt cagcgtaatg ctctgccagt gttacaacca   2640
attaaccaat tctgattaga aaaactcatc gagcatcaaa tgaaactgca atttattcat   2700
atcaggatta tcaataccat attttttgaaa aagccgtttc tgtaatgaag gagaaaactc   2760
accgaggcag ttccatagga tggcaagatc ctggtatcgg tctgcgattc cgactcgtcc   2820
aacatcaata aacctatta atttcccctc gtcaaaaata aggttatcaa gtgagaaatc   2880
accatgagtg acgactgaat ccggtgagaa tggcaagagc ttatgcattt ctttccagac   2940
ttgttcaaca ggccagccat tacgctcgtc atcaaaatca ctcgcatcaa ccaaaccgtt   3000
attcattcgt gattgcgcct gagcgaggcg aaatacgcga tcgctgttaa aaggacaatt   3060
acaaacagga atcgaatgca accggcgcag gaacactgcc agcgcatcaa caatattttc   3120
acctgaatca ggatattctt ctaatacctg gaatgctgtt ttcccaggga tcgcagtggt   3180
gagtaaccat gcatcatcag gagtacggat aaaatgcttg atggtcggaa gaggcataaa   3240
ttccgtcagc cagtttagtc tgaccatctc atctgtaaca tcattggcaa cgctacccttt   3300 gccatgtttc agaaacaact ctggcgcatc gggcttccca tacaatcggt agattgtcgc   3360
acctgattgc ccgacattat cgcgagccca tttataccca tataaatcag catccatgtt   3420
ggaatttaat cgcggcctcg tcgagcaaga cgtttcccgt tgaatatggc tcataacacc   3480
ccttgtatta ctgtttatgt aagcagacag ttttattgtt catttaaatg cggccgcgta   3540
cggcggcttc gatagcttca gcctccttag gagcattcaa accataacga aggagaaggg   3600
aagcagataa aattgtacca acaggattaa caatgccctt gccagcgata tcgggagcgc   3660
taccgtgaat gggctcaacc aaacaatgaa ccttttcttc tgattttcct accacaccgg   3720
aaagggaggc agaaggcaaa aggcccaagc taccaggaat gacagaagcc tcatctgaaa   3780
taatgtcacc aaacaagttg tcagtcaaaa caacaccgtt aagtgtacga gggctcttga   3840
ccaaaagcat ggctgcggag tcaatgagct ggttttttaa ggtaaggtga ggatattcct   3900
ccttaaaaat cttagctaca gtcttgcgcc aaagacgaga agttgccaaa acattagctt   3960
tgtcgagtaa tgtgacggga gcaggagggt tggaagtttc agctaaccaa gcagccaaac   4020
gagcaatacg agaaacttct tccaaactgt aaggccaagt gtccatagca taacccgatc   4080
cgttgtcctc agtgcgctca ccaaagtaac aacctccagt aagttctcgt acaacacaaa   4140
aatcgacacc ttcaacgatt tcaggcttca aagggctgta cttgactaaa gacttgctgg   4200
caaagttgca aggtcgaagg ttggcccaaa cacccatact cttacgaagc ttcaataaac   4260
cttgctcagg acgacaattg gggttggtcc attcaggacc accaacggca cccaaaagaa   4320
caccgtcagc ttccaaacaa gccttcacag tctcgtcagt caagggggtt ccataggcat   4380
caatagaggc acctccaatc ttgtgttctt caaactcgag ttttaactca ggtcgcttct   4440
tctcaacgac tttcaaaacc tccaaggcag aagcaacaat tcagggcca atatggtctc   4500 ctggtaagac gacgattttc tttgcacaca tgttgttgaa gaagtttgt tgtgaaatgg   4560 tttcgtgaaa gtttcagacc ctaccgcaaa aatgcctggt tcgggaaac tcaacactgt   4620 tgcactttt atactacaga ttgggatatc gataatattg cgtaaaaaat cctttttta   4680
```

-continued

```
aaaagcttgt ttacagtaac gtaaatgacc agaaatcaga tgaaaatcac aagaaagcaa    4740
ataattcacg ttaaatcctg atatgtttga ttttgtgatg aaatcatgga tgttcatagg    4800
aattgttgaa attgcgcttt tttaacgaaa tatacaagta tcctggagct tacttaatta    4860
attaatgaat ctttgtttct agttttaccc atcgtaaaga tcttgagagc tctccacttt    4920
gaacctctaa cctagcgagg gttttaccgt actcgctatc tcgctttgca aatccacaaa    4980
gcttctgtat tacatcataa gaaagtagag tgggcgctca ttggaaatag cttacgtagc    5040
tcagaaaacg aatggtgcga agaaaagggg ctttgctaga agctgctcat tatttgtctg    5100
attggatagc gagctatctg atagaaaact acgtaattcc ttggatcgca gttttctcca    5160
gtttctaatg ctaactgacg caaatgtgat gtaatgggct gcgatcataa tgacatgagc    5220
aattggacaa gaagctataa atacgagtcc aagttcaaca gtttaatcat tcaattcaat    5280
tccaatcaat ttaattgtct taaatattca aaacatgaag atcaccgctg tcattgccct    5340
tttattctca cttgctgctg cctcacctat tccagttgcc gatcctggtg tggtttcagt    5400
tagccttaag aagcgtgccg acgagttggc cttctccccc cccttctacc cctcccctg     5460 ggccaacggt caaggtgagt gggccgaggc ttaccaacgt gccgtcgcca ttgtctccca    5520
aatgacccct gacgagaagg tcaaccttac caccggtact ggttgggagc ttgagaagtg    5580
cgtcggtcaa accggtggtg tcccccgtct taacatcggt ggtatgtgcc ttcaagactc    5640
cccccttggt atccgtgact ccgactacaa ctccgccttc cctgccggtg tcaacgtcgc    5700
cgccacctgg gacaagaacc ttgcctacct tcgtggtcaa gctatgggtc aagagttctc    5760
cgacaagggt atcgacgtcc aacttggtcc tgccgccggt ccccttggtc gttccccga    5820 cggtggtcgt aactgggagg gtttctcccc cgaccccgcc cttaccggtg tccttttcgc    5880
cgagactatc aagggtatcc aagacgctgg tgtcgtcgcc accgccaagc actacatcct    5940
taacgagcaa gagcacttcc gtcaagtcgc cgaggccgct ggttacggtt tcaacatctc    6000
cgacaccatc tcttccaacg ttgacgacaa gaccatccac gagatgtacc tttggcccct    6060
cgccgacgcc gtccgtgccg gtgtcggtgc catcatgtgc tcctacaacc aaatcaacaa    6120
ctcctacggt tgccaaaact cctacaccct taacaagttg ttgaaggccg agcttggttt    6180
ccaaggtttc gtcatgtccg actggggtgc ccaccactcc ggtgttggtt ccgcccttgc    6240
cggtcttgac atgtccatgc ccggtgacat caccttcgac tccgctacct ccttctgggg    6300
caccaacctt accattgccg tccttaacgg tactgtcccc caatggcgtg ttgacgacat    6360
ggccgtccgt atcatggccg cctactacaa ggtcggtcgt gaccgtcttt accaaccccc    6420
caacttctcc tcctggaccc gtgacgagta cggtttcaag tacttctacc cccaagaggg    6480
tccctacgag aaggttaacc acttcgtcaa cgtccaacgt aaccactccg aggtcatccg    6540
taagttgggt gccgactcca ccgtcctttt gaagaacaac aacgccttgc ccttgaccgg    6600
taaggagcgt aaggtcgcca tccttggtga ggacgccggt tccaactctt acggtgccaa    6660
cggttgctcc gaccgtggtt gcgacaacgg tactcttgct atggcctggg gttccggtac    6720
tgccgagttc ccctaccttg tcacccccga gcaagccatc caagccgagg tcttgaagca    6780
caagggttcc gtctacgcca tcaccgacaa ctgggcttg tcccaagtcg agactcttgc    6840
caagcaagcc tctgtctccc ttgttttcgt caactccgac gccggtgagg gttacatctc    6900
cgttgacggt aacgagggtg accgtaacaa ccttaccctt tggaagaacg gtgacaacct    6960
tatcaaggcc gctgccaaca actgcaacaa caccatcgtc gtcatccact ccgtcggtcc    7020
```

| | |
|---|---|
| cgtccttgtt gacgagtggt acgaccaccc aacgtcacc gccatcctttt gggccggttt | 7080 |
| gcccggtcaa gagtccggta actcccttgc cgacgtcctt tacggtcgtg tcaaccccgg | 7140 |
| tgccaagtcc cccttcacct ggggtaagac ccgtgaggct tacggtgact accttgtccg | 7200 |
| tgagcttaac aacggtaacg gtgcccccca agacgacttc tccgagggtg ttttcatcga | 7260 |
| ctaccgtggt ttcgacaagc gtaacgagac tcccatctac gagttcggtc acggtttgtc | 7320 |
| ctacaccacc ttcaactact ccggtctcca catccaagtc cttaacgcct cctccaacgc | 7380 |
| ccaagtcgcc accgagactg gtgccgcccc taccttcggt caagtcggta acgcctccga | 7440 |
| ctacgtctac cccgagggtc ttacccgtat ctccaagttc atctacccct ggcttaactc | 7500 |
| taccgacttg aaggcttcct ccggtgaccc ctactacggt gttgacaccg ccgagcacgt | 7560 |
| ccccgagggt gccaccgacg gttccccca accgtccctt cccgctggtg gtggttccgg | 7620 |
| tggtaaccct cgtctttacg acgagcttat ccgtgtctcc gtcaccgtca agaacaccgg | 7680 |
| tcgtgtcgcc ggtgacgccg tcccccaact ttacgtttcc cttggtggtc ccaacgagcc | 7740 |
| caaggtcgtc cttcgtaagt tcgaccgtct taccttgaag ccctccgagg agactgtctg | 7800 |
| gaccaccacc cttacccgtc gtgaccttc caactgggac gtcgccgccc aagactgggt | 7860 |
| catcacctcc taccccaaga aggtccacgt cggttcctct tcccgtcaac ttccccttca | 7920 |
| cgccgccctt cccaaggtcc aatgataatc tagagtcgac ctgcagtcta gagtcgacct | 7980 |
| gcaggcatgc aagcttatat tttgtttcaa gttaggaaag tataataact tttgtccctg | 8040 |
| catattcaat tgtaaagttt agtttatcct ttcatcgtaa ccacaattgt cacctaaatc | 8100 |
| tctaaaaatc tcttcactta tctagttaat gtcgtaacaa aaaagtccag tagcttcggg | 8160 |
| aaatgatgct tggaatcata caagtcgacg tgggttttcc cttcaacaat gtacagctct | 8220 |
| tttggctcgg aagcgacagc atatgcttcc tttgaaaaat acagagtgtc agccttctca | 8280 |
| ccagctatgt acaacaaagg cctaggagcc atttgtttaa gaacatccgt ggctccataa | 8340 |
| aagccagcca ataactccat gctccacggc tggaaaatac cggtggatcg aggatgggaa | 8400 |
| ccacgcggtg tacaataata gtcataggct tctttgaata ataatggggt ggcatcagac | 8460 |
| aattgctctc tttgggggaa taaattgaac aagtcatatg actcacccctt acaaatttgg | 8520 |
| ttcgcgaggc agcggcacct tctagtaggc | 8550 |

<210> SEQ ID NO 6
<211> LENGTH: 400
<212> TYPE: DNA
<213> ORGANISM: Schizosaccharomyces pombe

<400> SEQUENCE: 6

| | |
|---|---|
| tccactttga acctctaacc tagcgagggt tttaccgtac tcgctatctc gctttgcaaa | 60 |
| tccacaaagc ttctgtatta catcataaga aagtagagtg ggcgctcatt ggaaatagct | 120 |
| tacgtagctc agaaaacgaa tggtgcgaag aaaaggggct ttgctagaag ctgctcatta | 180 |
| tttgtctgat tggatagcga gctatctgat agaaaactac gtaattcctt ggatcgcagt | 240 |
| tttctccagt ttctaatgct aactgacgca aatgtgatgt aatgggctgc gatcataatg | 300 |
| acatgagcaa ttggacaaga agctataaat acgagtccaa gttcaacagt ttaatcattc | 360 |
| aattcaattc caatcaattt aattgtctta aatattcaaa | 400 |

<210> SEQ ID NO 7
<211> LENGTH: 6675
<212> TYPE: DNA
<213> ORGANISM: Artificial Sequence
<220> FEATURE:
<223> OTHER INFORMATION: Description of Artificial Sequence: pSL14lacZ

<400> SEQUENCE: 7

```
actagtgaat tcgagtatgt gtacgagttg tctttaaacc cacagaggta gaatgtatat      60
ataaaattaa taagctaagt gtaatactta aaaaatacat taattggaac tcgtatccta     120
ccatttacaa tgttcatcca attttttcag attgtactgt aaatagcgtt tgaaaacacc     180
aaattttaga agctaatcac tctcatcata atcgtctaca tcctcatcgt tatcgacgat     240
aaaagaatca tcttgcatgc tgggttcatc catgctatca aacgagggat caacgtaaat     300
aggtgttttc actgtagccg ctgctcttct ggttggcctc tttctaatcg gagaatctga     360
atcttctggt ggctctgcgt tagtcgaact agcttttgga gttgaactac tacctggaat     420
aataaaatca tcatcgtcat cttcaggtga ttgtttcttt accgagcttg cttttttccc     480
tttattcttc gcagaagcct tcgtggatgt tatggtggaa ggtttcaaac tgctaggcaa     540
caaatcatct tcatcgtctg aagaaaatat ggtagtagca actggtttat tagtcttttct    600
tcctcttcca gacgccgagg ctgctatttt tttgacgggt tttttactac ctgcgtcttc     660
agagtcaaca gattgacttc ttttttcttga ttttccacta tcactgctat ccaatcccgg    720
gctcttagat atgcgatttt cttcaactga taagccatga gagttatcct ctgtcttgac    780
aatgtttatg tcagatgatt tctcaggttc tttcgacgct cgaactcaa gtaaagtttg     840
ttgctttcga tttgttgtag atggtttgga ttcgctgcta gcttctttttt taacagcagt   900
acttgaggag gatccggcaa tagccctggg tttcctagta ccagtggatt tacctcgagg    960
cttcttttttc gttcgattta caaaatctct tgaggattgc tcttcttcta acatttctct  1020
ctgaatatca tccataacct tattccaagc atgctcaaat gcatccaaat catgaagcca   1080
caattcttta ggagtttttt taatcaaagc atccagttcg gccattactt cgtccttttt   1140
cttgagaagt tccacatacc gttcataggt caaagaccat aaaggcattg aaagaaggta   1200
attgtaggca tctgaatcct cgtcttgcga aacatcacca gattgttctt cttcagcaag   1260
agcattttca acttctaaat caaccaaatg ccctttcttt ggtttactga taggttgaaa   1320
cttcttttcc ttcagctcca caatgagatc cttttttcttc tttttttgaaa ctacaagctc   1380
cccctctata atcatatgaa taaaccgcgc ttgatttgaa aatctatcaa accttttttc   1440
caattcatta accatatgct ctttacgtct ctggtatgtc cttaaacgta cttcgtaaaa   1500
ctcggtcaaa atatcttcaa cactgtcata cttcttgatc cgtccagatg catcaaaagc   1560
aatcatatta ctcgttgctt gagtacgcga cagtttaaac ttaacttcca aggattcatt   1620
taatgcttct ttcatgccag cttcggtaag cgtgacatta aagtgaacat tccttcacc    1680
gtgatggctt tcatagtcca cgatgaattt acgaattttt tccgtaccaa caagaccagc   1740
ctccagatac tccttcattc gtacgattta aatgcggccg cttcggctgc ggcgagcggg   1800
tatcagctca ctcaaaggcg gtaatacggt tatccacaga atcaggggat aacgcaggaa   1860
agaacatgtg agcaaaaggc cagcaaaagg ccaggaaccg taaaaaggcc gcgttgctgg   1920
cgttttttcca taggctccgc cccccctgacg agcatcacaa aaatcgacgc tcaagtcaga   1980
ggtggcgaaa cccgacagga ctataaagat accaggcgtt tcccccctgga agctccctcg   2040
tgcgctctcc tgttccgacc ctgccgctta ccggatacct gtccgccttt ctcccttcgg   2100
gaagcgtggc gctttctcaa tgctcacgct gtaggtatct cagttcggtg taggtcgttc   2160
gctccaagct gggctgtgtg cacgaacccc ccgttcagcc cgaccgctgc gccttatccg   2220
```

```
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaagagtt ggtagctctt gatccggcaa acaaaccacc gctggtagcg    2460 gtggttttt tgtttgcaag cagcagatta cgcgcagaaa aaaggatct caagaagatc     2520 ctttgatctt ttctacgggg tctgacgctc agtggaacga aaactcacgt taagggattt    2580
tggtcatgag cttgcgccgt cccgtcaagt cagcgtaatg ctctgccagt gttacaacca    2640
attaaccaat tctgattaga aaaactcatc gagcatcaaa tgaaactgca atttattcat    2700
atcaggatta tcaataccat attttgaaa aagccgtttc tgtaatgaag gagaaaactc     2760
accgaggcag ttccatagga tgcaagatc ctggtatcgg tctgcgattc cgactcgtcc     2820
aacatcaata caacctatta atttccctc gtcaaaaata aggttatcaa gtgagaaatc     2880
accatgagtg acgactgaat ccggtgagaa tggcaagagc ttatgcattt ctttccagac    2940
ttgttcaaca ggccagccat tacgctcgtc atcaaaatca ctcgcatcaa ccaaaccgtt    3000
attcattcgt gattgcgcct gagcgaggcg aaatacgcga tcgctgttaa aaggacaatt    3060
acaaacagga atcgaatgca accggcgcag gaacactgcc agcgcatcaa caatattttc    3120
acctgaatca ggatattctt ctaatacctg gaatgctgtt ttcccaggga tcgcagtggt    3180
gagtaaccat gcatcatcag gagtacggat aaaatgcttg atggtcggaa gaggcataaa    3240
ttccgtcagc cagtttagtc tgaccatctc atctgtaaca tcattggcaa cgctacctt     3300 gccatgtttc agaaacaact ctggcgcatc gggcttccca tacaatcggt agattgtcgc    3360
acctgattgc ccgacattat cgcgagccca tttataccca tataaatcag catccatgtt    3420
ggaatttaat cgcggcctcg tcgagcaaga cgtttcccgt tgaatatggc tcataacacc    3480
ccttgtatta ctgtttatgt aagcagacag ttttattgtt catttaaatg cggccgcgta    3540
cggcggcttc gatagcttca gcctccttag gagcattcaa accataacga aggagaaggg    3600
aagcagataa aattgtacca acaggattaa caatgccctt gccagcgata tcgggagcgc    3660
taccgtgaat gggctcaacc aaacaatgaa cctttcttc tgattttcct accacaccgg    3720
aaagggaggc agaaggcaaa aggcccaagc taccaggaat gacagaagcc tcatctgaaa    3780
taatgtcacc aaacaagttg tcagtcaaaa caacaccgtt aagtgtacga gggctcttga    3840
ccaaaagcat ggctgcggag tcaatgagct ggtttttaa ggtaaggtga ggatattcct     3900
ccttaaaaat cttagctaca gtcttgcgcc aaagacgaga agttgccaaa acattagctt    3960
tgtcgagtaa tgtgacggga gcaggagggt tggaagtttc agctaaccaa gcagccaaac    4020
gagcaatacg agaaacttct tccaaactgt aaggccaagt gtccatagca taacccgatc    4080
cgttgtcctc agtgcgctca ccaaagtaac aacctccagt aagttctcgt acaacacaaa    4140
aatcgacacc ttcaacgatt tcaggcttca aagggctgta cttgactaaa gacttgctgg    4200
caaagttgca aggtcgaagg ttggcccaaa cacccatact cttacgaagc ttcaataaac    4260
cttgctcagg acgacaattg gggttggtcc attcaggacc accaacggca cccaaaagaa    4320
caccgtcagc ttccaaacaa gccttcacag tctcgtcagt caagggggtt ccataggcat    4380
caatagaggc acctccaatc ttgtgttctt caaactcgag ttttaactca ggtcgcttct    4440
tctcaacgac tttcaaaacc tccaaggcag aagcaacaat ttcagggcca atatggtctc    4500
ctggtaagac gacgattttc tttgcacaca tgttgttgaa gaagttttgt tgtgaaatgg    4560
tttcgtgaaa gtttcagacc ctaccgcaaa aatgcctggt ttcgggaaac tcaacactgt    4620
```

```
tgcactttt   atactacaga  ttgggatatc  gataatattg  cgtaaaaaat  ccttttttta   4680
aaaagcttgt  ttacagtaac  gtaaatgacc  agaaatcaga  tgaaaatcac  aagaaagcaa   4740
ataattcacg  ttaaatcctg  atatgtttga  ttttgtgatg  aaatcatgga  tgttcatagg   4800
aattgttgaa  attgcgcttt  tttaacgaaa  tatacaagta  tcctggagct  tacttaatta   4860
attaatgaat  ctttgtttct  agttttaccc  atcgtaaaga  tcttgagagc  tctccacttt   4920
gaacctctaa  cctagcgagg  gttttaccgt  actcgctatc  tcgctttgca  aatccacaaa   4980
gcttctgtat  tacatcataa  gaaagtagag  tgggcgctca  ttggaaatag  cttacgtagc   5040
tcagaaaacg  aatggtgcga  agaaaagggg  ctttgctaga  agctgctcat  tatttgtctg   5100
attggatagc  gagctatctg  atagaaaact  acgtaattcc  ttggatcgca  gttttctcca   5160
gtttctaatg  ctaactgacg  caaatgtgat  gtaatgggct  gcgatcataa  tgacatgagc   5220
aattggacaa  gaagctataa  atacgagtcc  aagttcaaca  gtttaatcat  tcaattcaat   5280
tccaatcaat  ttaattgtct  taaatattca  aaacatgtaa  agcaggtgtc  agggcgatgg   5340
cccactacgt  gaaccatcac  cctaatcaag  tttttgggg   tcgaggtgcc  gtaaagcact   5400
aaatcggaac  cctaaaggga  gcccccgatt  tagagcttga  cggggaaagc  cggcgaacgt   5460
ggcgagaaag  gaagggaaga  aagcgaaagg  agcgggcgct  agggcgctgg  caagtgtagc   5520
ggtcacgctg  cgcgtaacca  ccacacccgc  cgcgcttaat  gcgccgctac  agggcgcgtc   5580
ccattcgcca  ttcaggctgc  gcaactgttg  ggaagggcga  tcggtgcggg  cctcttcgct   5640
attacgccag  ctggcgaaag  ggggatgtgc  tgcaaggcga  ttaagttggg  taacgccagg   5700
gttttcccag  tcacgacgtt  gtaaaacgac  ggccagtgag  cgcgcgtaat  acgactcact   5760
atagggcgaa  ttggagctcc  accgcggtgg  cggccgctct  agaactagtg  atccccggg   5820 gctgcaggaa  ttcgatatca  agcttatcga  taccgtcgac  ctcgagggg   ggcccggtac   5880 ccagcttttg  ttccctttag  tgagggttaa  ttgcgcgctt  ggcgtaatca  tggtcatagc   5940
tgtttcctgt  gtgaaattgt  tatccgctca  caattccaca  acaatacga   gccgggagca   6000 taaagtgtaa  agcctggggt  gcctaatgag  tgagctaact  cacattaatt  gcgttgcgcc   6060
atgtgaagca  ggtgtcggta  cccggggatc  ctctagagtc  gacctgcagg  catgcaagct   6120
tatattttgt  ttcaagttag  gaaagtataa  taacttttgt  ccctgcatat  tcaattgtaa   6180
agtttagttt  atcctttcat  cgtaaccaca  attgtcacct  aaatctctaa  aaatctcttc   6240
acttatctag  ttaatgtcgt  aacaaaaaag  tccagtagct  tcgggaaatg  atgcttggaa   6300
tcatacaagt  cgacgtgggt  tttcccttca  acaatgtaca  gctcttttgg  ctcggaagcg   6360
acagcatatg  cttcctttga  aaaatacaga  gtgtcagcct  tctcaccagc  tatgtacaac   6420 aaaggctag   gagccatttg  tttaagaaca  tccgtggctc  cataaaagcc  agccaataac   6480
tccatgctcc  acggctggaa  ataccggtg   gatcgaggat  gggaaccacg  cggtgtacaa   6540
taatagtcat  aggcttcttt  gaataataat  ggggtggcat  cagacaattg  ctctctttgg   6600
gggaataaat  tgaacaagtc  atatgactca  cccttacaaa  tttggttcgc  gaggcagcgg   6660
caccttctag  taggc                                                       6675
```

<210> SEQ ID NO 8
<211> LENGTH: 3801
<212> TYPE: DNA
<213> ORGANISM: Artificial Sequence
<220> FEATURE:
<223> OTHER INFORMATION: Description of Artificial Sequence: ihc1
      promoter containing fragment

<400> SEQUENCE: 8

```
gattaagatc gttgactttc ttctataaaa gcaaagcatc gagaaagatt cgaacattgc    60
aaaaaaaaag gattacctat tccatataca ccatctgtct ctctcttttt gttgaggttg   120
ctagagtttg gttattggaa ctttcttttt tttgttgtat catcatttgt ttccttcctt   180
ccatctttat tttgggaaag cgacttgatc tctcttcgct gcacgaatct gtgataacaa   240
tatcttcact cattctttc gccagcatcc aattttgttt ttttttgag aaacaaatct    300
gctcttgtac atattctaca ttcttttgaa ttacaagtgg gtattttaca ttcatttgaa   360
taatttaaaa taaatctggc tagcatttat tttttaatat tctcccctt tttcttaca    420
tcccccattc tatcgtctag gatttcgggt tgaaattggg ttttaagttg tcctacattt   480
acacaaaata aacactgggt aatttcgtgt ttgggttggt ttggtaatac agcttgcgaa   540
tctcctttca tccagttatt ttttatttat atatattatt tctttcatta atcttttcgc   600
aattttgcat tcatttaaac cctcttttct tcattctctg ttgaaactac gaagcttagc   660
tacaaatccc actggctata tgtatgcatt tgtgttaaaa aagtttgtat agattattta   720
atctactcag cattctttct ctaaatagga atttgttact taatggagaa aaaaatgttt   780
cgatttacct agtgtatttg tttgtatact cacgtttaat ttcaaacatc cattctatct   840
tgtgtaattt ttggcatggt gaaaagata atcagcctta taatctttac aaaagtaaga   900
aattctgtaa ataagcctta atgcccttgc tttaaattaa aatggttctt tttcatgata   960
atgtttgcac tttgtgaata tattttagat agttctgtga ggtataatta agatgttta  1020
gagacttata caattttgtc tttataaatt cttaattgat tttaccatcc cagtttaact  1080
atgcttcgtc ggcatctctg cacatgtcgt gttttcttac cgtattgtcc taccaagaac  1140
ctctttttg cttggatcga aattaaaggt ttaaaagcaa agttatggat gctagagtat  1200
ttcaaagcta ttcagctaga gctgagggga tgaaaaatcc cattgccaag gaattgttgg  1260
ctttgatgga agaaaagcaa agcaacttgt cagtcgcggt cgatttgacg aagaaatccg  1320
aaatcttaga attggtagat aaaattggac cctatgtctg tgttatcaag acacatattg  1380
acgttgtcga ggatttcgac caggatatgg tagaaaaact ggtggcctta ggtaaaaagc  1440
atcgttttct tatctttgag gatcgcaaat tcgcagacat tggaaatacc gtcaagctac  1500
aatatgcatc tggtgtgtac aaaattgctt cttgggctca tatcacaaat tgccatacag  1560
tgccaggcga gggtattata caaggcctca aagaagttgg tttacctttg ggacgtggtc  1620
tcttgctttt ggctgaaatg tcttccaaag gctctttggc tactggttcc tacacagaga  1680
aaaccttaga atggtttgag aagcataccg attttgctt tggctttata gctggtcgtc  1740
gatttcctaa ccttcaaagc gactacataa ctatgtcccc tggtatcggc ttggatgtta  1800
aaggagacgg gctgggacag caatatcgta ctcctgaaga agtgattgta aactgcggta  1860
gcgatatcat cattgttggt cgtggagtct atggagctgg tcgtaatcct gttgtcgaag  1920
ccaagagata tagagaagct ggttggaagg catatcagca aagactttct cagcattaaa  1980
aaaagactaa tgtaaaattt ttttggttgg ttattgaaaa agtcgatgcc ttgtttgcgt  2040
ttgttttcct aggcgtttta tgtcagaagg catttagaat tagtatacaa gtactctttg  2100
gtaaaatttt atgtagcgac taaaatatta actattatag ataaacacct tgggaataaa  2160
aagtaatttg ctatagtaat ttattaaaca tgctcctaca acattaccac aatcttttct  2220
cttggattga cattgaataa gaaaagagtg aatttttta gacttgtaat gataactatg  2280
```

| | | |
|---|---|---|
| tacaaagcca atgaaagatg tatgtagatg aatgtaaaat accatgtaga caaacaagat | 2340 |
| aaaacttggt tataaacatt ggtgttggaa cagaataaat tagatgtcaa aaagtttcgt | 2400 |
| caatatcaca agctttggat ccttacctcc atgttcccga gatagagatt attccctagc | 2460 |
| cgaaattaga atttgcgaag aggttttatg ttatcgcggg gtcttccaca taggtgacaa | 2520 |
| cgattttta aattcgaatt caaaatgttt ctctaaaaaa agaaaaactt gcaaaaacgg | 2580 |
| ggaacatttg agaaaagggt catcggggta cagagggctt caactagctc gggatgatat | 2640 |
| cccatatttt atgcccgaca ccgtttgtca tccgcttagt cgtgataccc gtctgccaca | 2700 |
| tagcgaatgt caaggatta tgctacttta cgtgagaatg aaatatagac tttacacatc | 2760 |
| gccacatgat ggcatcgata gagctgctag tttcaattac tttcaattaa cgagtgaaaa | 2820 |
| gcggatgtac cgcatcatct gttgagcgaa atagtctacg taaaatcaaa tgggctaatt | 2880 |
| tgtcgctgaa ttaacccaaa agcaaaaata cgattgcaat tctcattacg aaatgctgaa | 2940 |
| tgggatggaa aataaattga tgtcacaatt tccgaggact cttacaaata ttatatatag | 3000 |
| agcacggggt acatcactat cgattcgaat tttcaagaag taatatttcg caccgtagta | 3060 |
| cttttttgtaa gccgttttat taaatcagaa agaactccaa ttttatttat aaacaatgtc | 3120 |
| tgttagaagg ttttatcca catctgctcg ggcattactt tcacggctg ctcttcttcc | 3180 |
| ctccttgact tctggtctac cttctggaaa tgtcaggatt tgcaaaagg gaatggaacc | 3240 |
| tgaagattac ctttcctctg catcacaaaa tgaagtgcct cacgatattt cacttccaaa | 3300 |
| gaccgagctt gcggatccaa atttcctagt tgacgatatg ccaaccttac ttggcagaga | 3360 |
| cgctgctgtt gatcctagca tgtttactag caccttcaca gtaaaaaatg gaaatgatgc | 3420 |
| taactacatt actgctagtc ccgttagcaa cgacgcttcc atgactgcta ttagcacttt | 3480 |
| tacctcaggg aaagaagctt cttatgcaat tcaagcaagc ccatctacct ttcttcctga | 3540 |
| ttcgactacc acttcaggtt cacaagtttc aaatgctgtt gaagcgagct caacttttgt | 3600 |
| agctgatacg actagcacct catgcaaccc agcaacggtt ttaattgtaa ccacatctgg | 3660 |
| ttcaacaagt actagttgtc cccctccaac aacaattctt attgttacag tccctaccac | 3720 |
| aaccacaaca actactgttg gatatcctgg atccgtcact actaccttga ctggaactcc | 3780 |
| tagcaatggt actgttattg a | 3801 |

<210> SEQ ID NO 9
<211> LENGTH: 501
<212> TYPE: DNA
<213> ORGANISM: Schizosaccharomyces pombe

<400> SEQUENCE: 9

| | | |
|---|---|---|
| tggcttcaac tagctcggga tgatatccca tattttatgc ccgacaccgt ttgtcatccg | 60 |
| cttagtcgtg ataccgtct gccacatagc gaatgtcaaa ggattatgct actttacgtg | 120 |
| agaatgaaat atagctttta cacatcgcca catgatggca tcgatagagc tgctagtttc | 180 |
| aattactttc aattaacgag tgaaaagcgg atgtaccgca tcatctgttg agcgaaatag | 240 |
| tctacgtaaa atcaaatggg ctaatttgtc gctgaattaa cccaaaagca aaatacgat | 300 |
| tgcaattctc attacgaaat gctgaatggg atggaaaata aattgatgtc acaatttccg | 360 |
| aggactctta caaatattat atatagagca cggggtacat cactatcgat tcgaattttc | 420 |
| aagaagtaat atttcgcacc gtagtacttt ttgtaagccg ttttattaaa tcagaaagaa | 480 |
| ctccaatttt atttataaac a | 501 |

<210> SEQ ID NO 10
<211> LENGTH: 5526
<212> TYPE: DNA
<213> ORGANISM: Artificial Sequence
<220> FEATURE:
<223> OTHER INFORMATION: Description of Artificial Sequence: pUC19-ura4

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ccgtacggtg tgtactttga     420
aagtctagct ttacagcttg gcattgttca tacaaacgtc ttcagcatat ctttccacac     480
ttgctctgta cacgtattct ttccctctta tcattcctgt ttttctttt taataaacca      540
acatgcctgt aagtagtttt atctttagaa atctgtgcat catggatcct aactatgtct     600
tttagacggt tcaaactccc tctcagcgtc gtgcaaacac acagtttcag aagaacatta     660
ctcgtcgtgt aaaacaaat tcaaaagaac gttatgttgc caaacatcct cctaccaaga      720
ttcctcgtaa cattgccagt aagtaagaat tgatcctatt gttagcaact ttggcttgtg     780
tttcatactg acaatgcatc ttagtgtttt ttattcttct catgtcagga ggaattattt     840
tgggaatact tagatttctt ttgacgtttt tttcttaaga acatgtgatt ggagcaattt     900
taaaacctat ttgcaccgat attgtgtatt atactccgag aaaaagtata ctagttttga     960
ataataaagc ttgtgatatt gacgaaactt tttgacatct aatttattct gttccaacac    1020
caatgtttat aaccaagttt tatcttgttt gtctacatgg tattttacat tcatctacat    1080
acatctttca ttggctttgt acatagttat cattacaagt ctaaaaaaat tcactctttt    1140
cttattcaat gtcaatccaa gagaaaagat tgtggtaatg ttgtaggagc atgtttaata    1200
aattactata gcaaattact ttttattccc aaggtgttta tctataatag ttaatatttt    1260
agtcgctaca taaaatttta ccaaagagta cttgtatact aattctaaat gccttctgac    1320
ataaaacgcc taggaaaaca aacgcaaaca aggcatcgac tttttcaata accaaccaaa    1380
aaaattttac attagtctttt ttttaatgct gagaaagtct ttgctgatat gccttccaac    1440
cagcttctct atatctcttg gcttcgacaa caggattacg accagctcca tagactccac    1500
gaccaacaat gatgatatcg ctaccgcagt ttacaatcac ttcttcagga gtacgatatt    1560
gctgtcccag cccgtctcct ttaacatcca agccgatacc aggggacata gttatgtagt    1620
cgctttgaag gttaggaaat cgacgaccag ctataaagcc aaagcaaaaa tcggtatgct    1680
tctcaaacca ttctaaggtt ttctctgtgt aggaaccagt agccaagag cctttggaag     1740
acatttcagc caaaagcaag agaccacgtc ccaaaggtaa accaacttct tgaggccctt    1800
gtataatacc ctcgcctggc actgtatggc aatttgtgat atgagcccaa gaagcaattt    1860
tgtacacacc agatgcatat tgtagcttga cggtatttcc aatgtctgcg aatttgcgat    1920
cctcaaagat aagaaaacga tgcttttac ctaaggccac cagttttct accatatcct      1980
ggtcgaaatc ctcgacaacg tcaatatgtg tcttgataac acagacatag ggtccaattt    2040
tatctaccaa ttctaagatt tcggattcct tcgtcaaatc gaccgcgact gacaagttgc    2100
```

```
tttgctttc  ttccatcaaa  gccaacaatt  ccttggcaat  gggatttttc  atcccctcag   2160
ctctagctga  atagctttga  aatactctag  catccataac  tttgcttta   aacctttaat   2220 ttcgatccaa  gcaaaaaga   ggttcttggt  aggacaatac  ggtaagaaaa  cacgacatgt   2280
gcagagatgc  cgacgaagca  tagttaaact  gggatggtaa  aatcaattaa  gaatttataa   2340
agacaaaatt  gtataagtct  ctaaaacatc  ttaattatac  ctcacagaac  tatctaaaat   2400
atattcacaa  agtgcaaaca  ttatcatgaa  aaagaaccat  tttaatttaa  agcaagggca   2460
ttaaggctta  tttacagaat  ttcttacttt  tgtaaagatt  ataaggctga  ttatcttttt   2520
caccatgcca  aaaattacac  aagatagaat  ggatgtttga  aattaaacgt  gagtatacaa   2580
acaaatacac  taggtaaatc  gaaacatttt  tttctccatt  aagtaacaaa  ttcctattta   2640
gagaaagaat  gctgagtaga  ttaaataatc  tatacaaact  tttttaacac  aaatgcatac   2700
atatagccag  tgggatttgt  agctaagctt  caggagtttt  atccatttaa  tgtatggaat   2760
caaaatttaa  agcttctgtc  aaagtttaac  aatatttctt  ttggtttaaa  tcaaatcttc   2820
catgcgatta  agaagataga  tgctgaacaa  agaagcaca   tggataacca  caaaagcagt   2880
ttgctcatgg  gtacaaccat  gaattttttt  ttcgacaatg  attcaaagac  cagtatatcc   2940
aatacgcatc  ctagaatcta  gtcaaagaag  aacctaaagt  agagatgcaa  atgcgctaaa   3000
aagagtggat  ataaattcaa  tatcatttat  aaaacaactt  cttccattaa  aaattccttg   3060
ggcaaaacaa  aagttccaat  cataaaaagt  taataagttc  tgagttgtgt  caaatctgac   3120
atggcattcc  tcaataatga  cactcactca  ttatgtaagc  atcgaaaaca  tattaaaatc   3180
tatacaagct  gttttgtcat  tacggtctgg  catcaacttt  tttagaggcg  gtacgaagat   3240
gattttgcac  acggataacc  aattcttcat  gagacgtacg  gcatgcaagc  ttggcgtaat   3300
catggtcata  gctgtttcct  gtgtgaaatt  gttatccgct  cacaattcca  cacaacatac   3360
gagccggaag  cataaagtgt  aaagcctggg  gtgcctaatg  agtgagctaa  ctcacattaa   3420
ttgcgttgcg  ctcactgccc  gctttccagt  cgggaaacct  gtcgtgccag  ctgcattaat   3480
gaatcggcca  acgcgcgggg  agaggcggtt  tgcgtattgg  gcgctcttcc  gcttcctcgc   3540
tcactgactc  gctgcgctcg  tcgttcggc   tgcggcgagc  ggtatcagct  cactcaaagg   3600
cggtaatacg  gttatccaca  gaatcagggg  ataacgcagg  aaagaacatg  tgagcaaaag   3660
gccagcaaaa  ggccaggaac  cgtaaaaagg  ccgcgttgct  ggcgtttttc  cataggctcc   3720
gcccccctga  cgagcatcac  aaaaatcgac  gctcaagtca  gaggtggcga  aacccgacag   3780
gactataaag  ataccaggcg  tttccccctg  gaagctccct  cgtgcgctct  cctgttccga   3840
ccctgccgct  taccggatac  ctgtccgcct  ttctcccttc  gggaagcgtg  gcgctttctc   3900
atagctcacg  ctgtaggtat  ctcagttcgg  tgtaggtcgt  tcgctccaag  ctgggctgtg   3960
tgcacgaacc  ccccgttcag  cccgaccgct  gcgccttatc  cggtaactat  cgtcttgagt   4020
ccaacccggt  aagacacgac  ttatcgccac  tggcagcagc  cactggtaac  aggattagca   4080
gagcgaggta  tgtaggcggt  gctacagagt  tcttgaagtg  gtggcctaac  tacggctaca   4140
ctagaagaac  agtatttggt  atctgcgctc  tgctgaagcc  agttaccttc  ggaaaaagag   4200
ttggtagctc  ttgatccggc  aaacaaacca  ccgctggtag  cggtggtttt  tttgtttgca   4260
agcagcagat  tacgcgcaga  aaaaaggat   ctcaagaaga  tcctttgatc  ttttctacgg   4320
ggtctgacgc  tcagtggaac  gaaaactcac  gttaagggat  tttggtcatg  agattatcaa   4380
aaaggatctt  cacctagatc  cttttaaatt  aaaaatgaag  ttttaaatca  atctaaagta   4440
tatatgagta  aacttggtct  gacagttacc  aatgcttaat  cagtgaggca  cctatctcag   4500
```

```
cgatctgtct atttcgttca tccatagttg cctgactccc cgtcgtgtag ataactacga    4560
tacgggaggg cttaccatct ggccccagtg ctgcaatgat accgcgagac ccacgctcac    4620
cggctccaga tttatcagca ataaaccagc cagccggaag ggccgagcgc agaagtggtc    4680
ctgcaacttt atccgcctcc atccagtcta ttaattgttg ccgggaagct agagtaagta    4740
gttcgccagt taatagtttg cgcaacgttg ttgccattgc tacaggcatc gtggtgtcac    4800
gctcgtcgtt tggtatggct tcattcagct ccggttccca acgatcaagg cgagttacat    4860
gatccccat gttgtgcaaa aaagcggtta gctccttcgg tcctccgatc gttgtcagaa    4920
gtaagttggc cgcagtgtta tcactcatgg ttatggcagc actgcataat tctcttactg    4980
tcatgccatc cgtaagatgc ttttctgtga ctggtgagta ctcaaccaag tcattctgag    5040
aatagtgtat gcggcgaccg agttgctctt gcccggcgtc aatacgggat aataccgcgc    5100
cacatagcag aactttaaaa gtgctcatca ttggaaaacg ttcttcgggg cgaaaactct    5160
caaggatctt accgctgttg agatccagtt cgatgtaacc cactcgtgca cccaactgat    5220
cttcagcatc ttttactttc accagcgttt ctgggtgagc aaaaacagga aggcaaaatg    5280
ccgcaaaaaa gggaataagg gcgacacgga aatgttgaat actcatactc ttcctttttc    5340
aatattattg aagcatttat cagggttatt gtctcatgag cggatacata tttgaatgta    5400
tttagaaaaa taaacaaata ggggttccgc gcacatttcc ccgaaaagtg ccacctgacg    5460
tctaagaaac cattattatc atgacattaa cctataaaaa taggcgtatc acgaggccct    5520
ttcgtc                                                               5526

<210> SEQ ID NO 11
<211> LENGTH: 5960
<212> TYPE: DNA
<213> ORGANISM: Artificial Sequence
<220> FEATURE:
<223> OTHER INFORMATION: Description of Artificial Sequence: pSL6

<400> SEQUENCE: 11
aacccacaga ggtagaatgt atatataaaa ttaataagct aagtgtaata cttaaaaaat      60
acattaattg gaactcgtat cctaccattt acaatgttca tccaattttt tcagattgta     120
ctgtaaatag cgtttgaaaa caccaaattt tagaagctaa tcactctcat cataatcgtc     180
tacatcctca tcgttatcga cgataaaaga atcatcttgc atgctgggtt catccatgct     240
atcaaacgag ggatcaacgt aaataggtgt tttcactgta gccgctgctc ttctggttgg     300
cctcttctca atcggagaat ctgaatcttc tggtggctct gcgttagtcg aactagcttt     360
tggagttgaa ctactacctg gaataataaa atcatcatcg tcatcttcag gtgattgttt     420
ctttaccgag cttgcttttt tccctttatt cttcgcagaa gccttcgtgg atgttatggt     480
ggaaggtttc aaactgctag gcaacaaatc atcttcatcg tctgaagaaa atatggtagt     540
agcaactggt ttattagtct ttcttcctct tccagacgcc gaggctgcta ttttttttgac    600
gggtttttta ctacctgcgt cttcagagtc aacagattga cttcttttc ttgattttcc     660
actatcactg ctatccaatc ccgggctctt agatatgcga ttttcttcaa ctgataagcc    720
atgagagtta tcctctgtct tgacaatgtt tatgtcagat gatttctcag gttctttcga    780
cgctgcgaac tcaagtaaag tttgttgctt tcgatttgtt gtagatggtt tggattcgct    840
gctagcttct tttttaacag cagtacttga ggaggatccg gcaatagccc tgggtttcct   900
agtaccagtg gatttacctc gaggcttctt tttcgttcga tttacaaaat ctcttgagga   960
```

```
ttgctcttct tctaacattt ctctctgaat atcatccata accttattcc aagcatgctc    1020
aaatgcatcc aaatcatgaa gccacaattc tttaggagtt tttttaatca aagcatccag    1080
ttcggccatt acttcgtcct ttttcttgag aagttccaca taccgttcat aggtcaaaga    1140
ccataaaggc attgaaagaa ggtaattgta ggcatctgaa tcctcgtctt gcgaaacatc    1200
accagattgt tcttcttcag caagagcatt ttcaacttct aaatcaacca aatgcccttt    1260
ctttggttta ctgataggtt gaaacttctt ttccttcagc tccacaatga gatcctttt    1320 cttcttttt gaaactacaa gctcccctc tataatcata tgaataaacc gcgcttgatt    1380
tgaaaatcta tcaaacctt tttccaattc attaaccata tgctctttac gtctctggta    1440
tgtccttaaa cgtacttcgt aaaactcggt caaaatatct tcaacactgt catacttctt    1500
gatccgtcca gatgcatcaa aagcaatcat attactcgtt gcttgagtac gcgacagttt    1560
aaacttaact tccaaggatt catttaatgc ttctttcatg ccagcttcgg taagcgtgac    1620
attaaagtga acatttcctt caccgtgatg gctttcatag tccacgatga atttacgaat    1680
tttttccgta ccaacaagac cagcctccag atactccttc attcgtacga tttaaatgcg    1740
gccgcttcgg ctgcggcgag cgggtatcag ctcactcaaa ggcggtaata cggttatcca    1800
cagaatcagg ggataacgca ggaaagaaca tgtgagcaaa aggccagcaa aaggccagga    1860
accgtaaaaa ggccgcgttg ctggcgtttt tccataggct ccgcccccct gacgagcatc    1920
acaaaaatcg acgctcaagt cagaggtggc gaaacccgac aggactataa agataccagg    1980
cgtttccccc tggaagctcc ctcgtgcgct ctcctgttcc gaccctgccg cttaccggat    2040
acctgtccgc ctttctccct tcgggaagcg tggcgctttc tcaatgctca cgctgtaggt    2100
atctcagttc ggtgtaggtc gttcgctcca agctgggctg tgtgcacgaa ccccccgttc    2160
agcccgaccg ctgcgcctta tccggtaact atcgtcttga gtccaacccg gtaagacacg    2220
acttatcgcc actggcagca gccactggta acaggattag cagagcgagg tatgtaggcg    2280
gtgctacaga gttcttgaag tggtggccta actacggcta cactagaagg acagtatttg    2340
gtatctgcgc tctgctgaag ccagttacct tcggaaaaag agttggtagc tcttgatccg    2400
gcaaacaaac caccgctggt agcggtggtt ttttgtttg caagcagcag attacgcgca    2460 gaaaaaagg atctcaagaa gatcctttga tcttttctac ggggtctgac gctcagtgga    2520
acgaaaactc acgttaaggg attttggtca tgagcttgcg ccgtcccgtc aagtcagcgt    2580
aatgctctgc cagtgttaca accaattaac caattctgat tagaaaaact catcgagcat    2640
caaatgaaac tgcaatttat tcatatcagg attatcaata ccatattttt gaaaaagccg    2700
tttctgtaat gaaggagaaa actcaccgag gcagttccat aggatggcaa gatcctggta    2760
tcggtctgcg attccgactc gtccaacatc aatacaacct attaatttcc cctcgtcaaa    2820
aataaggtta tcaagtgaga aatcaccatg agtgacgact gaatccggtg agaatggcaa    2880
gagcttatgc atttctttcc agacttgttc aacaggccag ccattacgct cgtcatcaaa    2940
atcactcgca tcaaccaaac cgttattcat tcgtgattgc gcctgagcga ggcgaaatac    3000
gcgatcgctg ttaaaaggac aattacaaac aggaatcgaa tgcaaccggc gcaggaacac    3060
tgccagcgca tcaacaatat tttcacctga atcaggatat tcttctaata cctggaatgc    3120
tgttttccca gggatcgcag tggtgagtaa ccatgcatca tcaggagtac ggataaaatg    3180
cttgatggtc ggaagaggca taaattccgt cagccagttt agtctgacca tctcatctgt    3240
aacatcattg gcaacgctac ctttgccatg tttcagaaac aactctggcg catcgggctt    3300
cccatacaat cggtagattg tcgcacctga ttgcccgaca ttatcgcgag cccatttata    3360
```

```
cccatataaa tcagcatcca tgttggaatt taatcgcggc ctcgtcgagc aagacgtttc    3420
ccgttgaata tggctcataa caccccttgt attactgttt atgtaagcag acagttttat    3480
tgttcattta aatgcggccg cgtacggcgg cttcgatagc ttcagcctcc ttaggagcat    3540
tcaaaccata acgaaggaga agggaagcag ataaaattgt accaacagga ttaacaatgc    3600
ccttgccagc gatatcggga gcgctaccgt gaatgggctc aaccaaacaa tgaaccttt    3660 cttctgattt tcctaccaca ccggaaaggg aggcagaagg caaaaggccc aagctaccag    3720
gaatgacaga agcctcatct gaaataatgt caccaaacaa gttgtcagtc aaaacaacac    3780
cgttaagtgt acgagggctc ttgaccaaaa gcatggctgc ggagtcaatg agctggtttt    3840
ttaaggtaag gtgaggatat tcctccttaa aaatcttagc tacagtcttg cgccaaagac    3900
gagaagttgc caaaacatta gctttgtcga gtaatgtgac gggagcagga gggttggaag    3960
tttcagctaa ccaagcagcc aaacgagcaa tacgagaaac ttcttccaaa ctgtaaggcc    4020
aagtgtccat agcataaccc gatccgttgt cctcagtgcg ctcaccaaag taacaacctc    4080
cagtaagttc tcgtacaaca caaaaatcga caccttcaac gatttcaggc ttcaaagggc    4140
tgtacttgac taaagacttg ctggcaaagt tgcaaggtcg aaggtggcc caaacaccca    4200 tactcttacg aagcttcaat aaaccttgct caggacgaca attggggttg gtccattcag    4260
gaccaccaac ggcacccaaa agaacaccgt cagcttccaa acaagccttc acagtctcgt    4320
cagtcaaagg ggttccatag gcatcaatag aggcacctcc aatcttgtgt tcttcaaact    4380
cgagttttaa ctcaggtcgc ttcttctcaa cgactttcaa aacctccaag gcagaagcaa    4440
caatttcagg gccaatatgg tctcctggta agacgacgat tttctttgca cacatgttgt    4500
tgaagaagtt ttgttgtgaa atggtttcgt gaaagtttca gacctaccg caaaaatgcc    4560 tggtttcggg aaactcaaca ctgttgcact ttttatacta cagattggga tatcgataat    4620
attgcgtaaa aaatccttt tttaaaaagc ttgtttacag taacgtaaat gaccagaaat    4680
cagatgaaaa tcacaagaaa gcaaataatt cacgttaaat cctgatatgt ttgattttgt    4740
gatgaaatca tggatgttca taggaattgt tgaaattgcg ctttttttaac gaaatataca    4800 agtatcctgg agcttactta attaattaat gaatctttgt tcctaggccc gggctagtaa    4860
tcaattacgg ggtcattagt tcatagccca tatatggagt tccgcgttac ataacttacg    4920
gtaaatggcc cgcctggctg accgcccaac gacccccgcc cattgacgtc aataatgacg    4980
tatgttccca tagtaacgcc aatagggact ttccattgac gtcaatgggt ggagtattta    5040
cggtaaactg cccacttggc agtacatcaa gtgtatcata tgccaagtac gccccctatt    5100
gacgtcaatg acggtaaatg gcccgcctgg cattttgccc agtacatgac cttatgggac    5160
tttcctactt ggcagtacat ctacgtatta gtcatcgcta ttaccatggt gatgcggttt    5220
tggcagtaca tcaatgggcg tggatagcgg tttgactcac ggggatttcc aagtctccac    5280
cccattgacg tcaatgggag tttgttttgg caccaaaatc aacgggactt tccaaaatgt    5340
cgtaacaact ccgccccatt gacgcaaatg ggcggtaggc gtgtacggtg ggaggtctat    5400
ataagcagat ttctctttag ttcttttgcaa gaaggtagag ataaagacac ttttcaaac    5460 atgtgaagca ggtgtcggta cccggggatc ctctagagtc gacctgcagg catgcaagct    5520
taaataggaa agtttcttca acaggattac agtgtagcta cctacatgct gaaaaatata    5580
gcctttaaat cattttttata ttataactct gtataataga gataagtcca ttttttaaaa    5640
atgttttccc caaaccataa aaccctatac aagttgttct agtaacaata catgagaaag    5700
```

```
atgtctatgt agctgaaaat aaaatgacgt cacaagacga tctgcctcgc gcgtttcggt    5760
gatgacggtg aaaacctctg acacatgcag ctcccggaga cggtcacagc ttgtctgtaa    5820
gcggatgccg ggagcagaca agcccgtcag ggcgcgtcag cgggtgttgg cgggtgtcgg    5880
ggcgcagcca tgacccagtc acgtagcgat agcggagccc gggcactagt gaattcgagt    5940
atgtgtacga gttgtcttta                                                5960

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: ihc1-
      promoter-F

<400> SEQUENCE: 12
aattcctagg ggcttcaact agctcgggat                                       30

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: ihc1-
      promoter-R

<400> SEQUENCE: 13
aattggtacc gacacctgct tcacattgtt tataaataaa attggagtt                  49

<210> SEQ ID NO 14
<211> LENGTH: 5847
<212> TYPE: DNA
<213> ORGANISM: Artificial Sequence
<220> FEATURE:
<223> OTHER INFORMATION: Description of Artificial Sequence: pSL12

<400> SEQUENCE: 14
gaatgtatat ataaaattaa taagctaagt gtaatactta aaaatacat taattggaac        60 tcgtatccta ccatttacaa tgttcatcca atttttcag attgtactgt aaatagcgtt       120
tgaaaacacc aaattttaga agctaatcac tctcatcata atcgtctaca tcctcatcgt      180
tatcgacgat aaaagaatca tcttgcatgc tgggttcatc catgctatca aacgagggat      240
caacgtaaat aggtgttttc actgtagccg ctgctcttct ggttggcctc tttctaatcg      300
gagaatctga atcttctggt ggctctgcgt tagtcgaact agcttttgga gttgaactac      360
tacctggaat aataaaatca tcatcgtcat cttcaggtga ttgtttcttt accgagcttg      420
cttttttccc tttattcttc gcagaagcct tcgtggatgt tatggtggaa ggtttcaaac      480
tgctaggcaa caaatcatct tcatcgtctg aagaaaatat ggtagtagca actggtttat      540
tagtctttct tcctcttcca gacgccgagg ctgctatttt tttgacgggt ttttactac        600 ctgcgtcttc agagtcaaca gattgacttc ttttttcttga ttttccacta tcactgctat     660
ccaatcccgg gctcttagat atgcgatttt cttcaactga taagccatga gagttatcct      720
ctgtcttgac aatgtttatg tcagatgatt tctcaggttc tttcgacgct gcgaactcaa      780
gtaaagtttg ttgctttcga tttgttgtag atggtttgga ttcgctgcta gcttctttt       840 taacagcagt acttgaggag gatccggcaa tagccctggg tttcctagta ccagtggatt      900
tacctcgagg cttcttttc gttcgattta caaaatctct tgaggattgc tcttcttcta       960
acatttctct ctgaatatca tccataaccct tattccaagc atgctcaaat gcatccaaat    1020
```

```
catgaagcca caattcttta ggagttttt  taatcaaagc atccagttcg gccattactt   1080 cgtcctttt  cttgagaagt tccacatacc gttcataggt caaagaccat aaaggcattg   1140
aaagaaggta attgtaggca tctgaatcct cgtcttgcga acatcacca  gattgttctt   1200 cttcagcaag agcattttca acttctaaat caaccaaatg ccctttcttt ggtttactga   1260
taggttgaaa cttcttttcc ttcagctcca caatgagatc ctttttcttc tttttgaaa   1320 ctacaagctc cccctctata atcatatgaa taaaccgcgc ttgatttgaa atctatcaa    1380 accttttttc caattcatta accatatgct ctttacgtct ctggtatgtc cttaaacgta   1440
cttcgtaaaa ctcggtcaaa atatcttcaa cactgtcata cttcttgatc cgtccagatg   1500
catcaaaagc aatcatatta ctcgttgctt gagtacgcga cagtttaaac ttaacttcca   1560
aggattcatt taatgcttct ttcatgccag cttcggtaag cgtgacatta aagtgaacat   1620
ttccttcacc gtgatggctt tcatagtcca cgatgaattt acgaattttt tccgtaccaa   1680
caagaccagc ctccagatac tccttcattc gtacgattta aatgcggccg cttcggctgc   1740
ggcgagcggg tatcagctca ctcaaaggcg gtaatacggt tatccacaga atcaggggat   1800
aacgcaggaa agaacatgtg agcaaaaggc cagcaaaagg ccaggaaccg taaaaaggcc   1860
gcgttgctgg cgtttttcca taggctccgc cccctgacg  agcatcacaa aaatcgacgc   1920
tcaagtcaga ggtggcgaaa cccgacagga ctataaagat accaggcgtt ccccctgga   1980 agctccctcg tgcgctctcc tgttccgacc ctgccgctta ccggatacct gtccgccttt   2040
ctcccttcgg gaagcgtggc gctttctcaa tgctcacgct gtaggtatct cagttcggtg   2100
taggtcgttc gctccaagct gggctgtgtg cacgaacccc ccgttcagcc cgaccgctgc   2160
gccttatccg gtaactatcg tcttgagtcc aacccggtaa gacacgactt atcgccactg   2220
gcagcagcca ctggtaacag gattagcaga gcgaggtatg taggcggtgc tacagagttc   2280
ttgaagtggt ggcctaacta cggctacact agaaggacag tatttggtat ctgcgctctg   2340
ctgaagccag ttaccttcgg aaaaagagtt ggtagctctt gatccggcaa acaaaccacc   2400
gctggtagcg gtggtttttt tgtttgcaag cagcagatta cgcgcagaaa aaaggatct   2460 caagaagatc ctttgatctt ttctacgggg tctgacgctc agtggaacga aaactcacgt   2520
taagggattt tggtcatgag cttgcgccgt cccgtcaagt cagcgtaatg ctctgccagt   2580
gttacaacca attaaccaat tctgattaga aaaactcatc gagcatcaaa tgaaactgca   2640
atttattcat atcaggatta tcaataccat attttgaaa  aagccgtttc tgtaatgaag   2700
gagaaaactc accgaggcag ttccatagga tggcaagatc ctggtatcgg tctgcgattc   2760
cgactcgtcc aacatcaata caacctatta atttcccctc gtcaaaaata aggttatcaa   2820
gtgagaaatc accatgagtg acgactgaat ccggtgagaa tggcaagagc ttatgcattt   2880
ctttccagac ttgttcaaca ggccagccat tacgctcgtc atcaaaatca ctcgcatcaa   2940
ccaaaccgtt attcattcgt gattgcgcct gagcgaggcg aaatacgcga tcgctgttaa   3000
aaggacaatt acaaacagga atcgaatgca accggcgcag gaacactgcc agcgcatcaa   3060
caatattttc acctgaatca ggatattctt ctaatacctg gaatgctgtt ttcccaggga   3120
tcgcagtggt gagtaaccat gcatcatcag gagtacggat aaaatgcttg atggtcggaa   3180
gaggcataaa ttccgtcagc cagtttagtc tgaccatctc atctgtaaca tcattggcaa   3240
cgctaccttt gccatgtttc agaaacaact ctggcgcatc gggcttccca tacaatcggt   3300
agattgtcgc acctgattgc ccgacattat cgcgagccca tttataccca tataaatcag   3360
```

```
catccatgtt ggaatttaat cgcggcctcg tcgagcaaga cgtttcccgt tgaatatggc    3420
tcataacacc ccttgtatta ctgtttatgt aagcagacag ttttattgtt catttaaatg    3480
cggccgcgta cggcggcttc gatagcttca gcctccttag gagcattcaa accataacga    3540
aggagaaggg aagcagataa aattgtacca acaggattaa caatgcccct gccagcgata    3600
tcgggagcgc taccgtgaat gggctcaacc aaacaatgaa ccttttcttc tgattttcct    3660
accacaccgg aaagggaggc agaaggcaaa aggcccaagc taccaggaat gacagaagcc    3720
tcatctgaaa taatgtcacc aaacaagttg tcagtcaaaa caacaccgtt aagtgtacga    3780
gggctcttga ccaaaagcat ggctgcggag tcaatgagct ggttttttaa ggtaaggtga    3840
ggatattcct ccttaaaaat cttagctaca gtcttgcgcc aaagacgaga agttgccaaa    3900
acattagctt tgtcgagtaa tgtgacggga gcaggagggt tggaagtttc agctaaccaa    3960
gcagccaaac gagcaatacg agaaacttct tccaaactgt aaggccaagt gtccatagca    4020
taacccgatc cgttgtcctc agtgcgctca ccaaagtaac aacctccagt aagttctcgt    4080
acaacacaaa aatcgacacc ttcaacgatt tcaggcttca aagggctgta cttgactaaa    4140
gacttgctgg caaagttgca aggtcgaagg ttggcccaaa cacccatact cttacgaagc    4200
ttcaataaac cttgctcagg acgacaattg gggttggtcc attcaggacc accaacggca    4260
cccaaaagaa caccgtcagc ttccaaacaa gccttcacag tctcgtcagt caaggggtt    4320
ccataggcat caatagaggc acctccaatc ttgtgttctt caaactcgag ttttaactca    4380
ggtcgcttct tctcaacgac tttcaaaacc tccaaggcag aagcaacaat tcagggcca    4440
atatggtctc ctggtaagac gacgattttc tttgcacaca tgttgttgaa gaagttttgt    4500
tgtgaaatgg tttcgtgaaa gtttcagacc ctaccgcaaa aatgcctggt tcgggaaac    4560
tcaacactgt tgcactttt atactacaga ttgggatatc gataatattg cgtaaaaaat    4620
cctttttta aaagcttgt ttacagtaac gtaaatgacc agaaatcaga tgaaaatcac    4680
aagaaagcaa ataattcacg ttaaatcctg atatgtttga ttttgtgatg aaatcatgga    4740
tgttcatagg aattgttgaa attgcgcttt tttaacgaaa tatacaagta tcctggagct    4800
tacttaatta attaatgaat cttttgttcct aggggcttca actagctcgg gatgatatcc    4860
catattttat gcccgacacc gtttgtcatc cgcttagtcg tgatacccgt ctgccacata    4920
gcgaatgtca aaggattatg ctactttacg tgagaatgaa atatagactt tacacatcgc    4980
cacatgatgg catcgataga gctgctagtt tcaattactt tcaattaacg agtgaaaagc    5040
ggatgtaccg catcatctgt tgagcgaaat agtctacgta aaatcaaatg ggctaatttg    5100
tcgctgaatt aacccaaaag caaaaatacg attgcaattc tcattacgaa atgctgaatg    5160
ggatggaaaa taattgatg tcacaatttc cgaggactct tacaaatatt atatatagag    5220
cacggggtac atcactatcg attcgaattt tcaagaagta atatttcgca ccgtagtact    5280
ttttgtaagc cgttttatta aatcagaaag aactccaatt ttatttataa acaatgtgaa    5340
gcaggtgtcg gtacccgggg atcctctaga gtcgacctgc aggcatgcaa gcttaaatag    5400
gaaagtttct tcaacaggat tacagtgtag ctacctacat gctgaaaaat atagccttta    5460
aatcattttt atattataac tctgtataat agagataagt ccatttttta aaatgtttt    5520
ccccaaacca taaaacccta tacaagttgt tctagtaaca atacatgaga aagatgtcta    5580
tgtagctgaa aataaaatga cgtcacaaga cgatctgcct cgcgcgtttc ggtgatgacg    5640
gtgaaaacct ctgacacatg cagctcccgg agacggtcac agcttgtctg taagcggatg    5700
ccgggagcag acaagcccgt cagggcgcgt cagcgggtgt tggcgggtgt cggggcgcag    5760
```

```
ccatgaccca gtcacgtagc gatagcggag cccgggcact agtgaattcg agtatgtgta    5820
cgagttgtct ttaaacccac agaggta                                        5847
```

<210> SEQ ID NO 15
<211> LENGTH: 200
<212> TYPE: DNA
<213> ORGANISM: Schizosaccharomyces pombe

<400> SEQUENCE: 15

```
ttgctgccca gttgattacc cgtcattgct ttgatgtgtc tgaagtatct tcagttttga     60
ttttatgttg ttaatacaga attccatagt aatgatgagt atacatgttt atgatcttat    120
gaatattatt tcattcacca gcttttaact tttgaaaccg ttgtccttgt agaagtagtc    180
gacaccccat agcatacaat                                                200
```

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: ihc1-
      terminator-F

<400> SEQUENCE: 16

```
cctgcaggca tgcaagctta ttgctgccca gttgattacc c                         41
```

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: ihc1-
      terminator-R

<400> SEQUENCE: 17

```
gaaacgcgcg aggcagatca ttgtatgcta tggggtgtcg ac                        42
```

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: pSL12-F

<400> SEQUENCE: 18

```
gtcgacaccc catagcatac aatgatctgc ctcgcgcgtt tc                        42
```

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: pSL12-R

<400> SEQUENCE: 19

```
gggtaatcaa ctgggcagca ataagcttgc atgcctgcag g                         41
```

<210> SEQ ID NO 20
<211> LENGTH: 5831
<212> TYPE: DNA
<213> ORGANISM: Artificial Sequence
<220> FEATURE:
<223> OTHER INFORMATION: Description of Artificial Sequence: pSL17

```
<400> SEQUENCE: 20
gaatgtatat ataaaattaa taagctaagt gtaatactta aaaaatacat taattggaac    60
tcgtatccta ccatttacaa tgttcatcca attttttcag attgtactgt aaatagcgtt   120
tgaaaacacc aaattttaga agctaatcac tctcatcata atcgtctaca tcctcatcgt   180
tatcgacgat aaaagaatca tcttgcatgc tgggttcatc catgctatca aacgagggat   240
caacgtaaat aggtgttttc actgtagccg ctgctcttct ggttggcctc tttctaatcg   300
gagaatctga atcttctggt ggctctgcgt tagtcgaact agcttttgga gttgaactac   360
tacctggaat aataaaatca tcatcgtcat cttcaggtga ttgtttcttt accgagcttg   420
cttttttccc tttattcttc gcagaagcct tcgtggatgt tatggtggaa ggtttcaaac   480
tgctaggcaa caaatcatct tcatcgtctg aagaaaatat ggtagtagca actggtttat   540
tagtctttct tcctcttcca gacgccgagg ctgctatttt tttgacgggt tttttactac   600
ctgcgtcttc agagtcaaca gattgacttc tttttcttga ttttccacta tcactgctat   660
ccaatcccgg gctcttagat atgcgatttt cttcaactga taagccatga gagttatcct   720
ctgtcttgac aatgtttatg tcagatgatt tctcaggttc tttcgacgct gcgaactcaa   780
gtaaagtttg ttgctttcga tttgttgtag atggtttgga ttcgctgcta gcttcttttt   840
taacagcagt acttgaggag gatccggcaa tagccctggg tttcctagta ccagtggatt   900
tacctcgagg cttcttttc gttcgattta caaaatctct tgaggattgc tcttcttcta   960
acatttctct ctgaatatca tccataacct tattccaagc atgctcaaat gcatccaaat   1020
catgaagcca caattcttta ggagtttttt taatcaaagc atccagttcg gccattactt   1080
cgtccttttt cttgagaagt tccacatacc gttcataggt caaagaccat aaaggcattg   1140
aaagaaggta attgtaggca tctgaatcct cgtcttgcga aacatcacca gattgttctt   1200
cttcagcaag agcatttca acttctaaat caaccaaatg cccttctttt ggtttactga   1260
taggttgaaa cttcttttcc ttcagctcca caatgagatc cttttttcttc ttttttgaaa   1320 ctacaagctc cccctctata atcatatgaa taaaccgcgc ttgatttgaa aatctatcaa   1380 acctttttc caattcatta accatatgct ctttacgtct ctggtatgtc cttaaacgta   1440
cttcgtaaaa ctcggtcaaa atatcttcaa cactgtcata cttcttgatc cgtccagatg   1500
catcaaaagc aatcatatta ctcgttgctt gagtacgcga cagtttaaac ttaacttcca   1560
aggattcatt taatgcttct ttcatgccag cttcggtaag cgtgacatta aagtgaacat   1620
ttccttcacc gtgatggctt tcatagtcca cgatgaattt acgaattttt tccgtaccaa   1680
caagaccagc ctccagatac tccttcattc gtacgattta aatgcggccg cttcggctgc   1740
ggcgagcggg tatcagctca ctcaaaggcg gtaatacggt tatccacaga atcaggggat   1800
aacgcaggaa agaacatgtg agcaaaaggc cagcaaaagg ccaggaaccg taaaaaggcc   1860
gcgttgctgg cgttttccca taggctccgc cccctgacg agcatcacaa aaatcgacgc   1920
tcaagtcaga ggtggcgaaa cccgacagga ctataaagat accaggcgtt tccccctgga   1980
agctccctcg tgcgctctcc tgttccgacc ctgccgctta ccggatacct gtccgccttt   2040
ctcccttcgg gaagcgtggc gctttctcaa tgctcacgct gtaggtatct cagttcggtg   2100
taggtcgttc gctccaagct gggctgtgtg cacgaacccc ccgttcagcc cgaccgctgc   2160
gccttatccg gtaactatcg tcttgagtcc aacccggtaa gacacgactt atcgccactg   2220
gcagcagcca ctggtaacag gattagcaga gcgaggtatg taggcggtgc tacagagttc   2280
ttgaagtggt ggcctaacta cggctacact agaaggacag tatttggtat ctgcgctctg   2340
```

```
ctgaagccag ttaccttcgg aaaaagagtt ggtagctctt gatccggcaa acaaaccacc    2400
gctggtagcg gtggtttttt tgtttgcaag cagcagatta cgcgcagaaa aaaggatct     2460 caagaagatc ctttgatctt ttctacgggg tctgacgctc agtggaacga aaactcacgt    2520
taagggattt tggtcatgag cttgcgccgt cccgtcaagt cagcgtaatg ctctgccagt    2580
gttacaacca attaaccaat tctgattaga aaaactcatc gagcatcaaa tgaaactgca    2640
atttattcat atcaggatta tcaataccat attttttgaaa aagccgtttc tgtaatgaag    2700
gagaaaactc accgaggcag ttccatagga tggcaagatc ctggtatcgg tctgcgattc    2760
cgactcgtcc aacatcaata aacctatta atttccctc gtcaaaaata aggttatcaa      2820
gtgagaaatc accatgagtg acgactgaat ccggtgagaa tggcaagagc ttatgcattt    2880
ctttccagac ttgttcaaca ggccagccat tacgctcgtc atcaaaatca ctcgcatcaa    2940
ccaaaccgtt attcattcgt gattgcgcct gagcgaggcg aaatacgcga tcgctgttaa    3000
aaggacaatt acaaacagga atcgaatgca accggcgcag gaacactgcc agcgcatcaa    3060
caatattttc acctgaatca ggatattctt ctaatacctg gaatgctgtt tcccaggga     3120 tcgcagtggt gagtaaccat gcatcatcag gagtacggat aaaatgcttg atggtcggaa    3180
gaggcataaa ttccgtcagc cagtttagtc tgaccatctc atctgtaaca tcattggcaa    3240
cgctaccttt gccatgtttc agaaacaact ctggcgcatc gggcttccca tacaatcggt    3300
agattgtcgc acctgattgc ccgacattat cgcgagccca tttatacccca tataaatcag    3360 catccatgtt ggaatttaat cgcggcctcg tcgagcaaga cgtttcccgt tgaatatggc    3420
tcataacacc ccttgtatta ctgtttatgt aagcagacag ttttattgtt catttaaatg    3480
cggccgcgta cggcggcttc gatagcttca gcctccttag gagcattcaa accataacga    3540
aggagaaggg aagcagataa aattgtacca acaggattaa caatgccctt gccagcgata    3600
tcgggagcgc taccgtgaat gggctcaacc aaacaatgaa ccttttcttc tgattttcct    3660
accacaccgg aaagggaggc agaaggcaaa aggcccaagc taccaggaat gacagaagcc    3720
tcatctgaaa taatgtcacc aaacaagttg tcagtcaaaa caacaccgtt aagtgtacga    3780
gggctcttga ccaaaagcat ggctgcggag tcaatgagct ggttttttaa ggtaaggtga    3840
ggatattcct ccttaaaaat cttagctaca gtcttgcgcc aaagacgaga agttgccaaa    3900
acattagctt tgtcgagtaa tgtgacggga gcaggagggt tggaagtttc agctaaccaa    3960
gcagccaaac gagcaatacg agaaacttct tccaaactgt aaggccaagt gtccatagca    4020
taacccgatc cgttgtcctc agtgcgctca ccaaagtaac aacctccagt aagttctcgt    4080
acaacacaaa aatcgacacc ttcaacgatt tcaggcttca aagggctgta cttgactaaa    4140
gacttgctgg caaagttgca aggtcgaagg ttggcccaaa cacccatact cttacgaagc    4200
ttcaataaac cttgctcagg acgacaattg gggttggtcc attcaggacc accaacggca    4260
cccaaaagaa caccgtcagc ttccaaacaa gccttcacag tctcgtcagt caaagggtt     4320 ccataggcat caatagaggc acctccaatc ttgtgttctt caaactcgag tttaactca     4380 ggtcgcttct tctcaacgac tttcaaaacc tccaaggcag aagcaacaat tcagggcca    4440 atatggtctc ctggtaagac gacgattttc tttgcacaca tgttgttgaa gaagtttgt    4500 tgtgaaatgg tttcgtgaaa gtttcagacc ctaccgcaaa aatgcctggt tcgggaaac    4560 tcaacactgt tgcacttttt atactacaga ttgggtatc gataatattg cgtaaaaaat    4620 cctttttttta aaaagcttgt ttacagtaac gtaaatgacc agaaatcaga tgaaaatcac    4680
```

-continued

```
aagaaagcaa ataattcacg ttaaatcctg atatgtttga ttttgtgatg aaatcatgga    4740
tgttcatagg aattgttgaa attgcgcttt tttaacgaaa tatacaagta tcctggagct    4800
tacttaatta attaatgaat ctttgttcct aggggcttca actagctcgg gatgatatcc    4860
catattttat gcccgacacc gtttgtcatc cgcttagtcg tgatacccgt ctgccacata    4920
gcgaatgtca aaggattatg ctactttacg tgagaatgaa atatagactt tacacatcgc    4980
cacatgatgg catcgataga gctgctagtt tcaattactt tcaattaacg agtgaaaagc    5040
ggatgtaccg catcatctgt tgagcgaaat agtctacgta aaatcaaatg ggctaatttg    5100
tcgctgaatt aacccaaaag caaaaatacg attgcaattc tcattacgaa atgctgaatg    5160
ggatggaaaa taaattgatg tcacaatttc cgaggactct tacaaatatt atatatagag    5220
cacggggtac atcactatcg attcgaattt tcaagaagta atatttcgca ccgtagtact    5280
ttttgtaagc cgttttatta aatcagaaag aactccaatt ttatttataa acaatgtgaa    5340
gcaggtgtcg gtacccgggg atcctctaga gtcgacctgc aggcatgcaa gcttattgct    5400
gcccagttga ttacccgtca ttgctttgat gtgtctgaag tatcttcagt tttgatttta    5460
tgttgttaat acagaattcc atagtaatga tgagtataca tgtttatgat cttatgaata    5520
ttatttcatt caccagcttt taactttttga aaccgttgtc cttgtagaag tagtcgacac    5580
cccatagcat acaatgatct gcctcgcgcg tttcggtgat gacggtgaaa acctctgaca    5640
catgcagctc ccggagacgg tcacagcttg tctgtaagcg gatgccggga gcagacaagc    5700
ccgtcagggc gcgtcagcgg gtgttggcgg gtgtcggggc gcagccatga cccagtcacg    5760
tagcgatagc ggagcccggg cactagtgaa ttcgagtatg tgtacgagtt gtctttaaac    5820
ccacagaggt a                                                         5831
```

TRANSFORMANT OF *SCHIZOSACCHAROMYCES POMBE* MUTANT AND CLONING VECTOR

TECHNICAL FIELD

The present invention relates to a transformant of a *Schizosaccharomyces pombe* mutant which exhibits non-sexual flocculation and can produce β-glucosidase, and a vector useful for transforming a yeast of the genus *Schizosaccharomyces*.

BACKGROUND ART

To produce biomass fuels including a sugar as a fermentation feedstock, a bioethanol, etc. from a cellulosic biomass such as a wood, rice straw, rice husk or weed, it is required to degrade the main structural component of a plant cell wall, cellulose. To degrade cellulose, an acid saccharification method such as a concentrated sulfuric acid saccharification method or a dilute sulfuric acid saccharification method, an enzymatic saccharification method, etc. may be employed. Because of recent development in biotechnology, research and development of an enzymatic saccharification method are actively carried out.

In the enzymatic saccharification of cellulose, enzymes collectively known as cellulases are utilized. Firstly, an endoglucanase (EG), which has an activity to cleave cellulose chains at random, degrades an amorphous region of cellulose to expose terminal glucose residues. The exposed glucose residues are degraded by a cellobiohydrolase (CBH) to release cellobiose. Thereafter, the released cellobiose is degraded by β-glucosidase (BGL) to release glucose.

For the saccharification of cellulose, filamentous fungi of the genus *Aspergillus* and the genus *Trichoderma* are widely used, since they can produce various cellulases and hemicellulases which are required for degrading and saccharifying a crystalline cellulose, and they can secrete a large amount of such enzymes to their extracellular environment.

Further, it has been tried to express such cellulases of filamentous fungi in a heterologous microorganism. Non-patent document 1 discloses that a budding yeast *Saccharomyces cerevisiae* was transformed with a gene encoding β-glucosidase 1 (BGL 1) of *Aspergillus aculeatus* to obtain a transformant, and the obtained transformant expressed such an enzyme.

However, in the enzymatic saccharification method, as the enzymatic hydrolysis of cellulose proceeds, glucose accumulates in the reaction system and the accumulated glucose inhibits β-glucosidase, whereby accumulation of cellobiose proceeds. Further, there is a problem such that the complete degradation of cellulose may not be achieved since the accumulated cellobiose inhibits endoglucanase and cellobiohydrolase. Accordingly, development of a highly functional β-glucosidase has been desired.

On the other hand, the genetic analysis of a yeast of the genus *Schizosaccharomyces* is more advanced than that of a filamentous fungus of the genus *Aspergillus* or the genus *Trichoderma*, and the yeast has a lot of advantages like availability of various useful mutants and gene transfer vectors, and its suitability for industrial large-scale production of a protein. However, the yeast of the genus *Schizosaccharomyces* does not have endogenous β-glucosidase gene, whereby it cannot utilize cellobiose. The present inventors transformed a yeast of the genus *Schizosaccharomyces* with a gene encoding β-glucosidase thereby to express the enzyme from the obtained transformant (Patent Document 1).

Further, in Non-Patent Document 1, there is no description about an inhibitory effect of glucose to β-glucosidase produced by a budding yeast.

On the other hand, for recovering a β-glucosidase secreted from the transformant, a step of separating a culture broth and cells is required. Although steps of centrifugation, continuous centrifugation, membrane separation, etc. may be mentioned as the separation step, all of them are complicated steps and require a tremendous amount of labor and time.

In addition, it is easily expected that the complexity of the separation step increases as the scale of β-glucosidase production expands.

On the other hand, in the case of using a yeast which exhibits non-sexual flocculation (a property of aggregating non-sexually), aggregated yeast cells are easily separated from a culture broth after cultivation, whereby it is preferred to use a yeast which exhibits non-sexual flocculation as a host cell in the β-glucosidase production.

As the yeast which exhibits non-sexual flocculation, FLO mutants are known for budding yeast *Saccharomyces cerevisiae*. Further, mutants which exhibit non-sexual flocculation have been reported (e.g. Patent Document 2) for fission yeast *Schizosaccharomyces pombe* (hereinafter also referred to as *S. pombe*).

Further, a yeast of the genus *Schizosaccharomyces* such as *S. pombe* is phylogenetically quite different from budding yeast *Saccharomyces cerevisiae*. It is significantly different from other yeasts in its chromosome structure and various mechanisms including genome replication mechanism, RNA splicing mechanism, transcriptional machinery and post-translational modification, and some of them are known to be similar to those of animal cells. Therefore, it has been widely used as a model eukaryote (Non-Patent Document 2).

Because of its various characteristics, *S. pombe* is considered as a unicellular eukaryote closer to higher animal cells and is a very useful yeast as a host for expression of foreign genes, especially genes derived from higher animals. In particular, it is known to be suitable for expression of genes derived from animals such as human (Patent Documents 3 to 9).

For expressing a protein derived from a foreign structural gene by using *S. pombe* hosts, usually, a promoter which promotes transcription of the foreign structural gene encoding the protein is required. As the promoter, endogenous promoters for *S. pombe* genes and promoters from other organisms or viruses are known.

As promoters which have been utilized for the protein expression in *S. pombe* hosts, promoters endogenous to *S. pombe* including an alcohol dehydrogenase (adh1) gene promoter, a nmt1 gene promoter involved in thiamine metabolism, a fructose-1, 6-bis phosphatase (fbp1) gene promoter involved in glucose metabolism, an invertase (inv1) gene promoter involved in catabolite repression (Patent Document 7 or 10), a heat shock protein gene promoter (Patent Document 11) may, for example, be mentioned. Further, a promoter of a virus such as hCMV, SV40, or CaMV (constructive expression) is also known (Patent Document 4, 6 or 12).

PRIOR ART DOCUMENTS

Patent Documents

Patent Document 1: WO 2012/060389
Patent Document 2: JP-A-2000-106867

Patent Document 3: JP-B-2776085
Patent Document 4: JP-A-H07-163373
Patent Document 5: WO 96/23890
Patent Document 6: JP-A-H10-234375
Patent Document 7: JP-A-H11-192094
Patent Document 8: JP-A-2000-136199
Patent Document 9: JP-A-2000-262284
Patent Document 10: WO 99/23223
Patent Document 11: WO 2007/26617
Patent Document 12: JP-A-H5-15380

Non-Patent Documents

Non-Patent Document 1: G. Takada, et al., Biosci. Biotechnol. Biochem., 62(8), 1615-1618, 1998.
Non-Patent Document 2: Giga-Hama and Kumagai, eds., Foreign gene expression in fission yeast *Schizosaccharomyces pombe*, Springer-Verlag, (1997).

DISCLOSURE OF INVENTION

Technical Problem

During the cultivation of yeasts, the pH of a culture broth may be shifted to an acidic range. Particularly, in the case of expressing a large amount of acidic secretory proteins, the pH of a culture broth is likely to be shifted to an acidic range of from 2 to 5 at the end of cultivation. Further, when cultivating yeasts, the optimum pH for the cultivation may be lower than 5, considering productivity of a desired protein.

Therefore, in the case of using yeasts which exhibit flocculation in a culture broth having a relatively high pH, e.g. higher than pH 5, and do not aggregate under an acidic condition of pH 2 to 5, for the aggregation of the yeasts, a neutralization process is required to be carried out at the end of cultivation so as to adjust the pH to a neutral range.

Yeasts disclosed in Patent Document 1 are *S. pombe* mutants which exhibit non-sexual flocculation, and are preferred as host cells for the above-described expression system. However, although such *S. pombe* mutants were found to aggregate non-sexually in a YPD medium (usually, pH 5.6 to 6.0), it is unclear as to whether they exhibit sufficient flocculation under an acidic condition.

Therefore, the present invention is to provide a transformant of a *S. pombe* mutant which can produce and collect β-glucosidase without requiring complicated separation steps, and a method for producing β-glucosidase by using the transformant.

Further, the present invention is to provide an expression vector which is associated with a novel promoter and can express a protein derived from a foreign structural gene efficiently by genetic engineering when a yeast of the genus *Schizosaccharomyces* is used as a host; a cloning vector for preparing the expression vector; a method for producing the expression vector; a transformant comprising the expression vector; a method for producing the transformant; and a method for producing a protein using the transformant.

Solution to Problem

The transformant of a *S. pombe* mutant of the present invention is a transformant of a *Schizosaccharomyces pombe* mutant which exhibits an increased Gsf activity and decreased or no pyruvyl transferase Pvg1 enzymatic activity, and is comprised of a structural gene sequence encoding a β-glucosidase derived from a filamentous fungus, and a promoter sequence and a terminator sequence for expressing the structural gene in a chromosome or as an extrachromosomal gene.

Further, in the transformant of a *S. pombe* mutant of the present invention, the β-glucosidase is preferably BGL1.

Further, in the transformant of a *S. pombe* mutant of the present invention, the filamentous fungus is preferably a microorganism of the genus *Aspergillus*.

Further, in the transformant of a *S. pombe* mutant of the present invention, the β-glucosidase is preferably comprised of an amino acid sequence represented by SEQ ID NO: 1 or is comprised of the amino acid sequence having deletion, substitution or addition of at least one amino acid, and has a catalytic activity to hydrolyze a β-D-glucopyranoside bond.

Further, the method for producing a β-glucosidase of the present invention is characterized by cultivating the above-mentioned transformant and, from a cell or a culture supernatant thereby obtained, recovering a β-glucosidase.

Hereinafter, the invention relates to a transformant comprising a structural gene sequence encoding the β-glucosidase is referred to as the invention of the first embodiment.

The cloning vector of the present invention is characterized by comprising a hsp9 gene promoter or an ihc1 gene promoter of a yeast of the genus *Schizosaccharomyces*, a cloning site for introducing a foreign structural gene which is located downstream from the promoter and is governed by the promoter, and a terminator capable of functioning in the yeast of the genus *Schizosaccharomyces*.

The promoter of hsp9 gene (hereinafter also referred to as hsp9 promoter) is preferably a region containing 1 to 400 bp upstream from the 5' end of a hsp9 gene ORF (open reading frame), and is more preferably one comprised of a nucleotide sequence represented by SEQ ID NO: 6 or the nucleotide sequence having deletion, substitution or addition of at least one nucleotide, and has a promoter activity.

The promoter of ihc1 gene (herein after also referred to as ihc1 promoter) is preferably a region containing 1 to 501 bp upstream from the 5' end an ihc1 gene ORF (open reading frame), and is more preferably one comprised of a nucleotide sequence represented by SEQ ID NO: 9 or the nucleotide sequence having deletion, substitution or addition of at least one nucleotide, and has a promoter activity.

The method for producing an expression vector of the present invention is characterized by introducing a foreign structural gene into a cloning site of the above-described cloning vector, and the expression vector of the present invention is an expression vector comprising a foreign structural gene which is introduced into the cloning site of the above-described cloning vector.

The transformation method for a yeast of the genus *Schizosaccharomyces* of the present invention is characterized by introducing the above-described expression vector into the yeast of the genus *Schizosaccharomyces*, and the transformant of the present invention is a transformant comprising the above-described expression vector.

The method for producing a protein of the present invention is characterized by cultivating the above-described transformant and, from a cell or a culture supernatant thereby obtained, recovering a protein encoded by the above-described foreign structural gene.

Hereinafter, the invention relates to a cloning vector, an expression vector and a transformant having the above-described hsp9 promoter or ihc1 promoter, and the invention relates to a method for producing the expression vector, a method for producing a transformant and a method for producing a protein are referred to as the inventions of the second embodiment.

Advantageous Effect of Invention

According to the transformant of a S. *pombe* mutant of the present invention, it is possible to produce and collect a β-glucosidase without requiring complicated separation steps.

BRIEF DESCRIPTION OF DRAWING(S)

FIG. 6 (*b*) is a graph showing the ethanol concentration of a culture broth for a normal strain or a flocculation strain in Test Example 8.

FIG. 9 (*b*) is a graph showing the ethanol concentration of a culture broth for a normal strain or a flocculation strain in Test Example 10.

DESCRIPTION OF EMBODIMENTS

Figure 1:
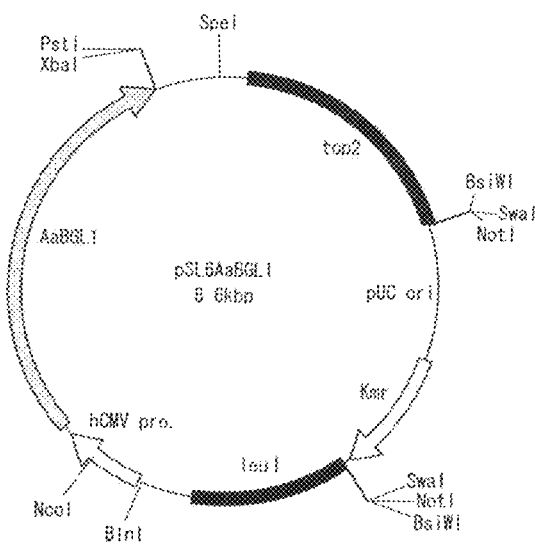
FIG. 1 is a construction map of expression vector pSL6AaBGL1.

In the present specification, "foreign structural gene" is a gene contained in an expression vector and encodes a protein, and may be a structural gene endogenous to a host to be introduced with the expression vector or a structural gene of an organism heterologous to the host.

In the present specification, "protein derived from a foreign structural gene" is a protein derived from a foreign structural gene and produced from a transformant, and hereinafter, it is also referred to as "foreign protein". Further, it is also referred to as a heterologous protein in a case where the foreign structural gene is a structural gene of an organism heterologous to the host.

Firstly, the first embodiment of the present invention will be described.

[S. *pombe* Mutant]

In the present invention, a S. *pombe* mutant to be used as a host of a S. *pombe* mutant transformant is a mutant exhibits, as a result of modifications in at least a part of S. *pombe* genes, an increased Gsf activity and decreased or no pyruvyl transferase Pvg1 enzymatic activity. In S. *pombe*, when the Gsf activity increases and the enzymatic activity of Pvg1 decreases or is lost, a property aggregating non-sexually even under an acidic condition will be obtained. Hereinafter, a property of aggregating non-sexually under an acidic condition is also referred to as "acid-resistance non-sexual flocculation".

In other words, the S. *pombe* mutant of the present invention is a mutant which has acquired acid-resistance non-sexual flocculation.

In the present invention, "non-sexual flocculation" is an aggregating property different from the property of aggregating sexually which is intrinsic to S. *pombe* (sexual flocculation). However, it does not mean that the intrinsic sexual flocculation is lost. Further, "constitutive flocculation" is a property identical to the non-sexual flocculation, and particularly refers to a property of aggregating (non-sexually) concurrently with the cell growth at a growing stage.

In the present invention, "Gsf activity" means non-sexual flocculation exhibited in the pH (e.g. pH 5 to 6) generally used for cultivating S. *pombe*. Further, a gene related to the Gsf activity is referred to as a flocculation gene.

gsf2 gene is a flocculation gene in S. *pombe*. The systematic name of gsf2 gene of S. *pombe* is SPCC1742.01.

Pvg1 is a pyruvate transferase. The systematic name of pvg1 gene encoding Pvg1 of S. *pombe* is SPAC8F11.10c.

Further, the entire nucleotide sequence of the chromosomes of S. *pombe* is stored and opened to the public in "*Schizosaccharomyces pombe* Gene DB (HyperText Markup Language://WorldWideWeb.genedb.org/genedb/pombe/)" of Sanger Institute. The sequence data of S. *pombe* genes described in the present specification are available from the data base by searching with a gene name or a systematic name.

S. *pombe* originally exhibits sexual flocculation induced by pheromones. For example, during the growth process, nutritional deficiencies likely to cause sexual flocculation. However, in an artificial large-scale cultivation such as a tank culture, sexual flocculation is usually less likely to occur since cultivation is carried out with a culture broth containing a sufficient amount of nutrients. On the other hand, since the S. *pombe* mutant used in the present invention exhibits non-sexual flocculation, it is subject to flocculation (constitutive flocculation) even in the case of cultivating in a culture broth containing a sufficient amount of nutrients.

The Gsf activity of a S. *pombe* mutant can be increased by, for example, increasing the expression amount of gsf2 gene. Further, the enzymatic activity of Pvg1 of S. *pombe* can be decreased or inactivated by deleting pvg1 gene encoding Pvg1 or by introducing a mutation which causes decrease or inactivation of the enzymatic activity of Pvg1 into the gene.

Therefore, the S. *pombe* mutant used in the present invention can be produced by employing a S. *pombe* which is prepared via a genetic engineering method and does not exhibit acid-resistance non-sexual flocculation of wild-type strains, etc. as a host, integrating a foreign gsf2 gene, and deleting a gene encoding Pvg1 or introducing a mutation which causes decrease or inactivation of the enzymatic activity of Pvg1 into the gene.

The expression amount of gsf2 gene can be increased by integrating a foreign gsf2 gene via a genetic engineering method. Introduction of a new gsf2 gene into a host is important, and a gsf2 gene to be introduced may be homologous to an endogenous gsf2 gene of the host, or may be a gsf2 gene derived from a heterologous organism.

As a method for introducing gsf2 gene into a host via a genetic engineering method, publicly known methods can be used. As a method for introducing a foreign structural gene into a S. *pombe* host, methods disclosed in JP-A-5-15380, WO 95/09914, JP-A-10-234375, JP-A-2000-262284, JP-A-2005-198612, WO 2010/087344, etc. may be used.

It is preferred to introduce gsf2 gene into the chromosome of S. *pombe*. By introducing gsf2 gene into a chromosome, a transformant having a high passage stability can be obtained. Further, multiple copies of gsf2 gene can be introduced into a chromosome. By introducing multiple copies of gsf2 gene, the expression efficiency of gsf2 gene can be increased. In a S. *pombe* mutant, the copy number of gsf2 gene integrated into the chromosome is preferably from 1 to 20, more preferably from 1 to 8.

As a method for introducing gsf2 gene into a chromosome, publicly known methods can be used. For example, by the method disclosed in JP-A-2000-262284, multiple copies of gsf2 gene can be introduced into a chromosome. Further, single copy of gsf2 gene can be introduced into a chromosome. Further, as described below, single or multiple copies of gsf2 gene can be introduced into multiple sites on a chromosome.

The method for introducing gsf2 gene into the chromosome of S. *pombe* is preferably a homologous recombination method using a vector comprising an expression cassette containing gsf2 gene and a recombination region (hereinafter referred to as gsf2 vector).

The gsf2 vector comprises an expression cassette containing gsf2 gene and a recombination region.

The expression cassette is a combination of DNA necessary for expressing Gsf2, and contains gsf2 gene, a promoter which functions in S. *pombe* and a terminator which functions in S. *pombe*. Further, it may contain at least one of a 5'-untranslation region and a 3'-untranslation region. Further, it may contain an auxotrophic complementation marker. The expression cassette is preferably an expression cassette containing gsf2 gene, a promoter, a terminator, a 5'-untranslation region, a 3'-untranslation region, and an auxotrophic complementation marker. Multiple copies of gsf2 gene may be present in the expression cassette. The copy number of gsf2 gene in the expression cassette is preferably from 1 to 8, more preferably from 1 to 5.

The promoter and terminator which function in S. *pombe* may be those which can maintain expression of Gsf2 by functioning in the transformant even under an acidic condition. As the promoter which functions in S. *pombe*, a promoter endogenous to S. *pombe* (preferably one having a high transcriptional activity), or a promoter exogenous to S. *pombe* (such as a promoter derived from a virus) may be used. Further, two or more types of promoters may be contained in the vector.

As the promoter endogenous to S. *pombe*, an alcohol dehydrogenase gene promoter, a nmt1 gene promoter involved in thiamine metabolism, a fructose 1,6-bisphosphatase gene promoter involved in glucose metabolism, an invertase gene promoter involved in catabolite repression (WO99/23223) or a heat shock protein gene promoter (WO2007/26617) may, for example, be mentioned. As the promoter exogenous to S. *pombe*, promoters derived from an animal cell virus disclosed in JP-A-5-15380, JP-A-7-163373 and JP-A-10-234375 may, for example, be mentioned. Among these promoters, a nmt1 gene promoter or its modified promoter (nmt1+, nmt41 or the like) having a high expression efficiency, a hCMV promoter and a SV40 promoter are preferred.

Further, the below-described hsp9 promoter or ihc1 promoter for the second embodiment of the present invention may also be used.

As the terminator which functions in S. *pombe*, a terminator endogenous to S. *pombe* or a terminator exogenous to S. *pombe* may be used. Further, two or more types of terminators may be contained in the vector.

As the terminator, terminators derived from human disclosed in JP-A-5-15380, JP-A-7-163373 and JP-A-10-234375 may, for example, be mentioned, and human lipocortin-1 terminator is preferred.

The recombination region of the vector is a region having a nucleotide sequence which can induce homologous recombination with a target site in the chromosome of S. *pombe* at which homologous recombination is to be achieved. Further, the target site is a site to become a target for integration of an expression cassette in the chromosome of S. *pombe*. The target site can be designed freely by letting the recombination region of the vector have a nucleotide sequence which induces homologous recombination with the target site.

The recombination region is required to have a nucleotide sequence homology of at least 70% with the nucleotide sequence of the target site. Further, the nucleotide sequence homology between the recombination region and the target site is preferably at least 90%, more preferably at least 95%, in view of increasing the efficiency of homologous recombination. By using a vector having such a recombination region, the expression cassette is integrated into the target site by homologous recombination.

The length (number of base pairs) of the recombination region is preferably from 20 to 2,000 bp. When the length of the recombination region is at least 20 bp, homologous recombination is likely to be induced. Further, when the length of the recombination region is at most 2,000 bp, reduction in the homologous recombination efficiency due to too large vector size is likely to be prevented. The length of the recombination region is preferably at least 100 bp, more preferably at least 200 bp. Further, the length of the recombination region is preferably at most 800 bp, more preferably at most 400 bp.

The vector may contain another DNA region in addition to the above-described expression cassette and recombination region. For example, a replication origin region called "ori" which is necessary for replication in E. coli, an antibiotic resistance gene (neomycin resistance gene or the like), etc. may be mentioned. These are genes generally required for the construction of a vector using E. coli. The replication origin region is preferably removed when integrating the vector into the chromosome of the host, as described below.

The vector is a vector having a circular DNA structure or a linear DNA structure, and is preferably introduced into S. pombe cells in the form of a linear DNA structure. That is, in a case where a vector having a circular DNA structure like a usual plasmid DNA is used, the vector is preferably cut open to a linear form by a restriction enzyme before its introduction into the S. pombe cells.

In this case, the vector having a circular DNA structure is cut open at a position within the recombination region. The resulting vector has parts of the recombination regions exist at both ends and is integrated entirely into the target site of a chromosome by homologous recombination.

The vector may be constructed by other methods without cutting a vector having a circular DNA structure so long as a linear DNA structure having parts of the recombination region at both ends can be obtained.

As the vector, a plasmid derived from E. coli such as pBR322, pBR325, pUC118, pUC119, pUC18, pUC19 or the like may suitably be used.

In this case, it is preferred that the replication origin region called "ori" required for replication in E. coli is removed from the plasmid vector to be used for homologous recombination. Thus, the integration efficiency at the time of integrating the above-described vector into a chromosome can be increased.

The method for constructing the vector in which the replication origin region is removed is not particularly limited, but is preferably the method disclosed in JP-A-2000-262284. That is, it is preferable to preliminarily construct a precursor vector carrying the replication origin region at a position to be cut within the recombination region so that the replication origin region will be cut-off from the vector at the time of preparing a linear DNA structure. Thus, a vector in which the replication origin region is removed can be obtained easily.

Further, it may be a method wherein a precursor vector containing an expression cassette and a recombination region is constructed by using the expression vectors and their construction methods disclosed in JP-A-5-15380, JP-A-7-163373, WO96/23890, JP-A-10-234375, and then the replication origin region is removed from the precursor vector by using a usual genetic engineering method to obtain a vector to be used for homologous recombination.

The target site for integration of the vector may be present in only one position of the chromosome of S. pombe, or may be present in two or more positions thereof. When the target site is present in two or more positions, the vector can be integrated into two or more positions of the chromosome of S. pombe. Further, when the vector has multiple copies of gsf2 gene, multiple copies of gsf2 gene can be integrated into one position of the target site. Further, the expression cassette may be integrated into two or more types of target sites by using two or more types of vectors having recombination regions corresponding to the respective target sites.

When the expression cassette is integrated into one target site, the target site disclosed in JP-A-2000-262284 may, for example, be used. By using two or more types of vectors having different recombination regions, each of the vectors can be integrated into different target sites. However, this method becomes complicated in the case of integrating vectors into two or more positions of the chromosome.

Assuming that nucleotide sequences which are substantially identical to one another and present in plural positions of a chromosome can be used as target sites and vectors can be integrated into the respective plural positions of target sites, vectors can be integrated into two or more positions of the chromosome by using a single type of vector. The nucleotide sequences which are substantially identical to one another means that the homology between the nucleotide sequences is at least 90%. The homology among the target sites is preferably at least 95%. Further, the length of the nucleotide sequences which are substantially identical to one another is a length encompassing the recombination region of a vector, and is preferably at least 1,000 bp. As compared with a case wherein multiple copies of gsf2 gene are integrated into one target site, even if the integration numbers of gsf2 gene are the same, when gsf2 gene is integrated into plural target sites in a dispersed manner, drop-out of every gsf2 gene from the chromosome is less likely to occur during cultivation, whereby the maintenance stability during cultivation of the transformant increases.

The target site present in plural positions of the chromosome is preferably transposon gene Tf2. Tf2 is a transposon gene which exists in every three chromosomes (monoploid) of S. pombe at 13 positions in total and has a length (number of base pairs) of about 4,900 bp, with a nucleotide sequence homology of 99.7% (refer to the below-identified reference).

Nathan J. Bowen et al., "Retrotransposons and Their Recognition of pol II Promoters: A Comprehensive Survey of the Transposable Elements From the Complete Genome Sequence of Schizosaccharomyces pombe", Genome Res., 2003 13: 1984-1997.

It is possible to integrate a vector into only one position of Tf2 which exists in 13 positions of the chromosome. In such a case, by integrating a vector containing two or more copies of gsf2 gene, a transformant having two or more copies of gsf2 gene can be obtained. Further, by integrating a vector into two or more positions of Tf2, a transformant having two or more copies of gsf2 gene can be obtained. In this case, by integrating a vector containing two or more copies of gsf2 gene, a transformant having even more copies of gsf2 gene can be obtained. When a vector is integrated into all 13 positions of Tf2, there is a possibility that the load on the survival and growth of the transformant becomes too large. It is preferred that a vector is integrated into at most 8 positions out of the 13 Tf2 positions, and it is more preferred that a vector is integrated into at most 5 positions.

For producing the S. pombe mutant of the present invention by a genetic engineering method, S. pombe having a marker for selecting a transformant is preferably used as a host. For example, it is preferred to use a host which essentially requires a specific nutrient factor for its growth due to deletion of a certain gene. By using a vector carrying the deleted gene (auxotrophic complementation marker), a transformant lacking the auxotrophy of the host will be obtained.

It is possible to select the transformant by using the difference in auxotrophy between the host and the transformant.

For example, a *S. pombe* host which has been made auxotrophic for uracil by deletion or inactivation of orotidine phosphate decarboxylase (ura4 gene) is transformed with a vector containing ura4 gene (auxotrophic complementation marker), and transformants carrying the vector are obtained by selecting ones lacking uracil auxotrophy. The gene to be deleted to make an auxotrophic host is not limited to ura4 gene when it is used for selection of a transformant, and may, for example, be isopropyl malate dehydrogenase gene (leu1 gene).

Usually, after carrying out homologous recombination, the obtained transformants are subjected to selection. The selection may, for example, be carried out as follows. Screening is carried out by a culture broth which can select transformants by the above-mentioned auxotrophic marker, and two or more colonies are selected among the obtained colonies. Then, after cultivating them separately in a liquid broth, the expression amount of gsf2 gene per cells in each liquid broth is measured so as to select a mutant showing higher expression amount. Further, the copy numbers of a vector and an expression cassette integrated into the chromosomes can be identified by subjecting the selected mutants to a genomic analysis using pulse-field gel electrophoresis.

The copy number of a vector integrated into the chromosomes can be adjusted to some extent by adjusting integration conditions, etc., but the integration efficiency and integration copy number also change due to the size (number of base pairs) and structure of the vector.

By deleting pvg1 gene or introducing a mutation which causes decrease or inactivation of the enzymatic activity of Pvg1 into pvg1 gene via a genetic engineering method, the enzymatic activity of Pvg1 of a *S. pombe* host can be decreased or inactivated. Deleting pvg1 gene per se from the chromosomes is preferred, since it ensures the complete inactivation of the enzymatic activity of Pvg1.

Deletion or inactivation of pvg1 gene can be carried out by publicly known methods. For example, the Latour system (Nucleic Acids Res. (2006) 34: e11, and WO2007/063919) can be used to delete pvg1 gene.

Further, the pvg1 gene may be inactivated by causing deletion, insertion, substitution or addition in a part of the nucleotide sequence of the pvg1 gene. The gene may be mutated by only one of the deletion, insertion, substitution and addition, or by two or more of them.

As a method for introducing the above-described mutation to a part of pvg1 gene, publicly known methods can be used. For example, a mutant screening method using mutagens (Koubo Bunshi Idengaku Jikken-Hou, 1996, Japan Scientific Societies Press), random mutations using PCR (polymerase chain reaction) (PCR Methods Appl., 1992, vol. 2, p. 28-33) and the like.

The *S. pombe* mutant of the present invention can also be obtained by an artificial mutation of a *S. pombe* which does not exhibit non-sexual flocculation. That is, it can be produced by subjecting a *S. pombe* which does not exhibit non-sexual flocculation to a mutation treatment, selecting cells exhibiting an increased Gsf activity as compared with a wild-type strain and having decreased or no Pvg1 enzymatic activity from the treated *S. pombe*, and further selecting ones resulting from dominant mutations in the increased Gsf activity and the decreased Pvg1 enzymatic activity, etc.

The mutation treatment of *S. pombe* may be carried out by using a mutagen such as EMS (ethyl methane sulfonate) or the like, or irradiating light of short wavelength such as ultraviolet rays or the like. Further, the selection of cells exhibiting acid-resistance non-sexual flocculation after subjecting *S. pombe* cells to a mutation treatment may be carried out in the presence of cations such as calcium ions.

The Gsf activity of a *S. pombe* mutant can be evaluated using, as an index, sedimentation rate. Thus, when *S. pombe* cells treated with mutagens are cultivated on a solid medium and colonies thereby formed are introduced into an appropriate solvent, the cells, which form colonies showing significantly faster sedimentation rate as compared with colonies of a wild-type strain (i.e. higher sedimentation rate), are evaluated as ones exhibit an increased Gsf activity as compared with wild-type strains. The colonies of a wild-type strain and the colonies of cells treated with mutagens can be introduced into solvents at almost the same time for comparing their sedimentation rates. The threshold value, determined by the preliminary measured sedimentation rate of a wild-type strain under a specific condition, may be compared with the sedimentation rate of the colonies of cells treated with mutagens. The solvents to be used for the sedimentation test of colonies are not particularly limited so long as they do not kill yeast cells, but are preferably buffers containing at least one cation selected from the group consisting of a calcium ion, a lithium ion, a manganese ion, a copper ion, and a zinc ion. For example, when the dried-cell concentration is 3.6 g/L, the cells having a sedimentation rate of at least 1.0 m/h in a calcium ion-containing lactate buffer solution (80 mM lactic acid, 100 mM calcium chloride, pH 6.0) can be selected as mutants exhibiting increased Gsf activity.

For example, an acid-resistance non-sexual flocculation strain can be obtained by the following operation. At first, mutation of *S. pombe* is induced by using EMS, and then mutated ones are isolated for cultivation. Then, cells collected after removing a culture supernatant are suspended in a lactic acid-sodium hydroxide buffer solution (80 mM lactic acid, 100 mM calcium chloride, pH 2.0) to a dried-cell concentration of 3.6 g/L, followed by measuring sedimentation rate to select a strain showing a sedimentation rate higher than 2.0 m/h as the acid-resistance non-sexual flocculation strain.

The mutant exhibiting increased Gsf activity can be selected by using, as an index, the expression amount of gsf2 gene. The expression amount of gsf2 gene may be measured by a measurement method generally used for gene expression analysis such as RT-PCR, Northern blotting using a labeled probe, or the like.

When the enzymatic activity of Pvg1 is decreased or inactivated, the amount of pyruvic acid contained in the cell surface tends to decrease significantly. Therefore, the enzymatic activity of Pvg1 of *S. pombe* can be evaluated using, as an index, the amount of pyruvic acid contained in the cell surface. That is, from *S. pombe* cells treated with mutagens, cells lacking pyruvic acid in their cell surfaces can be selected as a mutant exhibiting decreased or no Pvg1 enzymatic activity.

The mutant lacking pyruvic acid in its cell surface can by produced in accordance with a method of Andreishcheva et al., (The Journal of biological chemistry; 2004 Aug. 20, 279 (34):35644-55). At first, mutation of *S. pombe* cells is induced by using EMS, and the cells are cultivated for 48 hours in an appropriate liquid culture broth. Then, by using positively charged Q-sepharose, adhered cells are removed from the culture for collecting cells remained in the supernatant. After repeatedly carrying out the selection using Q-sepharose several times, the obtained culture supernatant was applied on a plate, followed by an isolation culture to obtain a mutant lacking pyruvic acid in its cell surface.

The mutant exhibiting decreased or no Pvg1 enzymatic activity can also be obtained by measuring the Pvg1 enzymatic activity of mutagen-treated cells. The Pvg1 enzymatic activity of *S. pombe* may be measured by a measurement method generally used for measuring enzymatic activities of other transferases such as a measurement method of using a labeled substrate, or the like.

The *S. pombe* mutant of the present invention may be prepared by combining a genetic engineering method and a mutation treatment. For example, a mutant in which the expression amount of gsf2 gene is increased by a mutation treatment may be subjected to a genetic engineering method to decrease or inactivate its Pvg1 enzymatic activity. Alternatively, a mutant in which its Pvg1 enzymatic activity is decreased or inactivated by a mutation treatment may be subjected to a genetic engineering method to increase the expression amount of gsf2 gene. Further, a mutant in which its Pvg1 enzymatic activity is decreased or inactivated by a genetic engineering method may be subjected to a mutation treatment to select a mutant in which the expression amount of gsf2 gene is increased.

The *S. pombe* mutant of the present invention may have a mutation in other genes so long as it maintains acid-resistance non-sexual flocculation, and further, it may contain a foreign structural gene in its chromosome or as an extrachromosomal gene.

The acid-resistance non-sexual flocculation of the *S. pombe* mutant of the present invention is not affected by the types of acids contained in a culture broth. That is, the *S. pombe* mutant is subject to non-sexual flocculation in all cases where the acid providing a culture broth pH range of from 2 to 5 is an organic acid such as lactic acid, citric acid, acetic acid, succinic acid, fumaric acid or malic acid, and where the acid is a mineral acid such hydrochloric acid or sulfuric acid.

As an index for the strength of non-sexual flocculation of the *S. pombe* mutant of the present invention, a sedimentation rate may, for example, be used. The sedimentation rate of yeast may, for example, be obtained by suspending yeast cells dispensed in a transparent container such as a test tube, letting them to stand still to start sedimentation, and dividing the distance between the liquid surface and the solid-liquid interface (interface between the sedimented yeast cells and the supernatant) by the time elapsed from the onset of sedimentation.

The *S. pombe* mutant of the present invention has a non-sexual flocculation property in a calcium ion-containing lactate buffer solution (80 mM lactic acid, 100 mM calcium chloride, pH 2.0). The sedimentation rate of the *S. pombe* mutant of the present invention in the calcium ion-containing lactate buffer solution is preferably at least 2.0 m/h, more preferably at least 4.0 m/h, further preferably at least 6.0 m/h, provided that the dried cell concentration is 3.6 g/L.

Further, the *S. pombe* mutant of the present invention has a non-sexual flocculation property in a calcium ion-containing lactate buffer solution (80 mM lactic acid, 100 mM calcium chloride, pH 4.0). The sedimentation rate of the *S. pombe* mutant of the present invention in the calcium ion-containing lactate buffer solution is preferably at least 2.0 m/h, more preferably at least 4.0 m/h, further preferably at least 8.0 m/h, provided that the dried cell concentration is 3.6 g/L.

When the sedimentation rate at pH 4.0 is at least 8.0 m/h, sufficient flocculation will be exhibited at a pH of lower than pH 4.

The acid-resistance non-sexual flocculation exhibited by the *S. pombe* mutant of the present invention may be dependent on at least one cation selected from the group consisting of a calcium ion, a lithium ion, a manganese ion, a copper ion, and a zinc ion. When the acid-resistance non-sexual flocculation is dependent on a calcium ion or the like, the aggregation of the *S. pombe* can be inhibited by adding a chelating agent such as EDTA to the culture broth.

The acid-resistance non-sexual flocculation exhibited by the *S. pombe* mutant of the present invention may be a property which is inhibited by galactose. When the acid-resistance non-sexual flocculation is inhibited by galactose, the aggregation of the *S. pombe* can be inhibited by adding galactose to the culture broth to a final concentration of at least 5 mM.

The *S. pombe* mutant of the present invention exhibits a strong non-sexual flocculation under an acidic condition (e.g. pH 2 to 5). Therefore, the *S. pombe* mutant is particularly suitable as a host of the expression system for synthesizing acidic proteins. Further, it is also suitable as a host of the expression system even in a case where the optimal pH for cultivation is lower than pH 5, considering the productivity of a desired protein.

When the below-described transformant of a *S. pombe* mutant of the present invention is prepared and the transformant is cultivated by a tank culture or the like, for the large scale production of β-glucosidase using the *S. pombe* mutant of the present invention as a host, even in a case where the pH of the culture broth is from 2 to 5 at the end of cultivation, cells can be aggregated without carrying out a solid-liquid separation treatment such as centrifugation or filtration, a neutralization treatment, etc., whereby the cells are easily separated from the culture broth. Further, the *S. pombe* mutant of the present invention may exhibit non-sexual flocculation under not only an acidic condition but also a weak acidic to alkaline (e.g. pH 5 to 10) condition.

[Transformant of *S. pombe* Mutant]

The transformant of a *S. pombe* mutant of the present invention is prepared by using the above-described *S. pombe* mutant, and has a structural gene sequence encoding a β-glucosidase derived from a filamentous fungus, and a promoter sequence and a terminator sequence for expressing the structural gene in a chromosome or as an extrachromosomal gene. Here, having the above-described expression cassette in a chromosome means that the expression cassette is integrated into at least one position of the chromosome of the yeast of the genus *Schizosaccharomyces*, and having as an extrachromosomal gene means that a plasmid having the expression cassette is contained in the yeast cell. From the viewpoint of easiness in subculture passage of the transformant, it is preferred to have the expression cassette in a chromosome.

The expression cassette is the same as one described in [*S. pombe* mutant], and is a combination of DNA necessary for expressing β-glucosidase, and contains a β-glucosidase structural gene, and a promoter and a terminator which function in a yeast of the genus *Schizosaccharomyces*.

Further, since recovery and purification of a β-glucosidase become easier when the amount of a β-glucosidase secreted out of the cells of a yeast of the genus *Schizosaccharomyces* is large, it is preferred that a nucleotide sequence encoding a secretion signal sequence (structural gene of secretion signal) which functions in a yeast of the genus *Schizosaccharomyces* is located at the 5' end side of the β-glucosidase structural gene. The 5' end side of the β-glucosidase structural gene is a region upstream from the β-glucosidase structural gene, and is a position adjacent to the 5' end of the g-glucosidase structural gene. Further, a nucleotide sequence encoding a number of amino acids in the N-terminal side, which does not affect the activity of β-glucosidase, may be removed and a gene encoding a secretion signal sequence may be introduced thereto.

The promoter and the terminator may be ones which function in a *S. pombe* mutant to direct expression of a β-glucosidase derived from a filamentous fungus. As the promoter which functions in a *S. pombe* mutant, those described in [*S. pombe* mutant] may be mentioned.
(β-glucosidase)

β-glucosidase (EC.3.2.1.21) is a generic name of an enzyme which specifically catalyzes hydrolysis of a β-D-glucopyranoside bond. Particularly, it is also called as cellobiase since it degrades cellobiose to glucose, and is widely found in bacteria, filamentous fungi, plants and animals. A plurality of genes encoding β-glucosidase is usually found in each of the species, and for example, existence of bgl1 to bgl7 in a filamentous fungus *Aspergillus oryzae* has been reported (Soy Protein Research, Japan, Vol. 12, pp. 78-83, 2009; and JP-A-2008-086310). Among them, bgl1 which encodes BGL1 is preferred from the viewpoint of its high activity, etc.

The structural gene of β-glucosidase contained in the transformant of a *S. pombe* mutant of the present invention is derived from a filamentous fungus.

The filamentous fungus is, among fungi, an eukaryotic microorganism composed of tubular cells called hyphae. As the filamentous fungus, a fungus of the genus *Aspergillus*, the genus *Trichoderma*, the genus *Fusarium*, the genus *Penicillium*, the genus *Acremonium* or the like may, for example, be mentioned. The structural gene of β-glucosidase of the present invention may be derived from any filamentous fungus so long as it produces β-glucosidase, but is preferably a β-glucosidase derived from a filamentous fungus of the genus *Aspergillus* from the viewpoint of its high enzymatic activity, etc. As the filamentous fungus of the genus *Aspergillus, Aspergillus nidulans, Aspergillus oryzae, Aspergillus aculeatus, Aspergillus niger*, and *Aspergillus pulverulentus* may, for example, be mentioned. The gene encoding a β-glucosidase derived from *Aspergillus aculeatus* is preferred since it has high crystalline cellulose degradation ability and high yield of monosaccharide, and the gene encoding BGL1 (hereinafter also referred to as AaBGL1) derived from *Aspergillus aculeatus* is more preferred.

According to the doctoral dissertation of Dr. Reiichiro Sakamoto (Research on cellulase system of *Aspergillus aculeatus* No. F-50, Osaka Prefecture University, 1984), the wild type AaBGL1 purified from *Aspergillus aculeatus* has a molecular weight of about 133 kDa, an optimal pH of 4.0, and a stable pH range of from 3 to 7 (25° C., 24 hours).

The amino acid sequence of AaBGL1 is an amino acid sequence represented by SEQ ID NO: 1. The gene sequence encoding β-glucosidase of the present invention is preferably a gene sequence encoding a β-glucosidase comprised of the amino acid sequence represented by SEQ ID NO: 1. Further, it may be a gene sequence encoding a β-glucosidase comprised of the amino acid sequence represented by SEQ ID NO:1 having deletion, substitution or addition of from one to tens amino acids, preferably from one to few amino acids, more preferably from one to nine amino acids, and has a catalytic activity to hydrolyze a β-D-glucopyranoside bond.

The β-glucosidase comprised of the amino acid sequence represented by SEQ ID NO: 1 is one retains a catalytic activity to hydrolyze a β-D-glucopyranoside bond even in a case where deletion, substitution or addition of from one to tens amino acids is introduced into the sequence.

The above-described gene encoding a β-glucosidase derived from a filamentous fungus may be used as it is. However, to increase expression in a yeast of the genus *Schizosaccharomyces*, it is preferred to modify the above-described gene sequence by changing its codons to ones frequently used in a gene highly expressed in a yeast of the genus *Schizosaccharomyces*.

In the present invention, as the vector for expressing β-glucosidase (hereinafter also referred to as bgl vector), a vector similar to the above-described gsf2 vector for expressing Gsf2 may be mentioned.

Further, the bgl vector preferably contains a secretion signal gene which functions in *S. pombe*. The secretion signal gene is located at the 5' end side of the β-glucosidase structural gene. The secretion signal gene which functions in *S. pombe* is a gene encoding an amino acid sequence having a function of secreting the expressed foreign protein out of the host cell. A foreign protein to which the secretion signal is attached at its N-terminal is expressed from a foreign structural gene to which the secretion signal gene is bound. The secretion signal is removed from the foreign protein in the endoplasmic reticulum and the Golgi apparatus, etc. of the host cell, and then, the foreign protein detached from the secretion signal is secreted out of the host cell. The secretion signal gene (and the secretion signal) should be capable of functioning in a *S. pombe* mutant. As the secretion signal gene capable of functioning in a *S. pombe* mutant, the secretion signal genes described in WO1996/23890 may be used.

In the present invention, the structural gene of the secretion signal is introduced at the 5' end side of the β-glucosidase structural gene, whereby it becomes possible to express a β-glucosidase to which the secretion signal is attached at its N-terminal, and then secrete the β-glucosidase out of the cells of yeast of the genus *Schizosaccharomyces*. As the secretion signal capable of functioning in a yeast of the genus *Schizosaccharomyces*, P3 signal described in WO1996/23890 is particularly preferred.

By using the above-described bgl vector, a *S. pombe* mutant, as a host, is transformed. The introduction of the β-glucosidase structural gene into the *S. pombe* mutant may be carried out in the same manner as in the introduction of gsf2 gene. Further, the selection of a transformant may be carried out in the same manner.

As the culture broth for cultivating the *S. pombe* mutant of the present invention, a publicly known culture broth for yeasts may be used so long as it contains carbon sources, nitrogen sources, inorganic salts and the like which yeast of the genus *Schizosaccharomyces* can use, and yeast of the genus *Schizosaccharomyces* can grow in it efficiently. The culture broth may be natural or synthetic.

As the carbon sources, saccharides such as glucose, fructose and sucrose may, for example, be mentioned.

As the nitrogen sources, inorganic acids or inorganic ammonium salts such as ammonia, ammonium chloride, and ammonium acetate, peptone and casamino acid may, for example, be mentioned.

As inorganic salts, magnesium phosphate, magnesium sulfate and sodium chloride may, for example, be mentioned.

Cultivation may be carried out by using a publicly known cultivation method for yeasts such as a shaking cultivation, a stirring cultivation or the like.

The cultivation temperature is preferably from 23 to 37° C. Further, the cultivation time may be set appropriately.

Cultivation may be carried by batch culture, fed-batch culture or continuous culture.

In the case of using, as the transformant of a *S. pombe* mutant of the present invention, a transformant having a β-glucosidase structural gene to which the secretion signal gene is bound, β-glucosidase is secreted into the culture broth. Then, when the transformant is cultivated in a tank culture or the like for the large scale production of β-glucosidase, since the transformant exhibits non-sexual flocculation even in a case where the pH of the culture broth is from 2 to 5 at the end of cultivation, cells can be aggregated without carrying out a solid-liquid separation treatment such as centrifugation or filtration, a neutralization treatment, etc., whereby the cells are easily separated from the culture broth.

Further, in the case of using, as the transformant of a *S. pombe* mutant of the present invention, a transformant having a β-glucosidase structural gene to which the secretion signal gene is not bound, a publicly known protein separation method may be used for separating a β-glucosidase.

For example, after cultivation, sedimented cells are separated from the culture broth and the cells are disrupted to obtain a cell lysate containing a β-glucosidase, and then the β-glucosidase is recovered by using a publicly known protein isolation method such as sating-out, column purification, chromatography or immunoprecipitation. Next, the second embodiment of the present invention will be described.

[Cloning Vector]

The cloning vector of the second embodiment of the present invention is a cloning vector for producing an expression vector to be introduced into a yeast of the genus *Schizosaccharomyces* for the expression of a foreign protein, and is characterized by having hsp9 promoter or ihc1 promoter of the yeast of the genus *Schizosaccharomyces* as a promoter which controls the expression of the foreign protein. Further, hereinafter, the cloning vector of the second embodiment of the present invention may also be referred to as the cloning vector of the present invention.

<hsp9 Promoter>

The hsp9 gene of a yeast of the genus *Schizosaccharomyces* is a gene encoding Hsp9 which is a kind of a heat shock protein (hsp) of a yeast of the genus *Schizosaccharomyces*. The systematic name of hsp9 gene registered in a gene sequence database of *S. pombe* (*S. pombe* Gene DB; HyperText Markup Language://WorldWideWeb.genedb.org/genedb/pombe/) is SPAP8A3.04c, Heat shock protein (hsp) is a generic name for proteins which are induced to be synthesized when a cell or an organism is suddenly exposed to a temperature 5 to 10° C. higher than its physiological temperature (heat shock) and function as a chaperon to protect proteins from thermal denaturation or aggregation. In vivo synthesis of heat shock proteins is induced by various chemical substances such as electron transport chain inhibitors, transition metals, SH reagents and ethanol as well as by heat shock.

Therefore, in the transformant prepared by introducing an expression vector having a hsp9 gene promoter, it is possible to control the expression of a foreign gene, in the same manner as in the expression of Hsp9 protein, by heat shock or stimulation with various chemical substances.

The expression efficiency of hsp9 promoter in a yeast of the genus *Schizosaccharomyces* is significantly high. Accordingly, by using this promoter, it becomes possible to prepare an expression vector which can produce an unexpectedly large amount of a foreign protein from a transformant.

The hsp9 promoter may be a promoter of hsp9 gene contained in a yeast of the genus *Schizosaccharomyces*, and may also be a promoter derived from any yeast of the genus *Schizosaccharomyces*, but is preferably a hsp9 promoter of *S. pombe* which is more widely used. The hsp9 promoter of *S. pombe* is a region contained in 1 to 400 bp upstream from the 5' end (A of initiation codon ATG) of a hsp9 gene ORF (SEQ ID NO:6).

As yeasts of the genus *Schizosaccharomyces*, other than *S. pombe*, which have hsp9 promoter, *Schizosaccharomyces japonicus* and *Schizosaccharomyces octosporus* may, for example, be mentioned. Further, the hsp9 promoter used for a cloning vector may be one derived from the same species as, or one derived from a species different from, the yeast of the genus *Schizosaccharomyces* to be introduced with an expression vector prepared from the cloning vector.

The hsp9 promoter is a region comprised of a nucleotide sequence identical to the promoter endogenous to a wild-type yeast of the genus *Schizosaccharomyces* (wild-type hsp9 promoter), or a region which has a promoter activity similar to the wild-type hsp9 promoter and is comprised of the nucleotide sequence having deletion, substitution or addition of at least one amino acid, preferably from one to tens amino acids, more preferably from one to dozen amino acids, further preferably from one to nine amino acids, even further preferably from one to few amino acids.

Further, the hsp9 promoter to be used for the cloning vector of the present invention may be a region which has a promoter activity similar to the wild-type hsp9 promoter and is comprised of an amino acid sequence having a homology to a nucleotide sequence identical to the wild-type hsp9 promoter of at least 80%, preferably at least 85%, more preferably at least 90%, further preferably at least 95%.

The hsp9 promoter of *S. pombe* is a region contained in 1 to 400 bp upstream from the 5' end (A of initiation codon ATG) of a hsp9 gene ORF. The nucleotide sequence of the region is shown as SEQ ID NO:6. That is, the cloning vector of the present invention preferably contains a region comprised of a nucleotide sequence represented by SEQ ID NO:6. Further, a region which has a promoter activity similar to the wild-type hsp9 promoter and is comprised of a nucleotide sequence represented by SEQ ID NO:6 having deletion, substitution or addition of at least one amino acid, preferably from one to tens amino acids, more preferably from one to dozen amino acids, further preferably from one to nine amino acids, even further preferably from one to few amino acids, or a nucleotide sequence having a homology to a sequence represented by SEQ ID NO:6 of at least 80%, preferably at least 85%, more preferably at least 90%, further preferably at least 95%, may also be used suitably as the hsp9 promoter for the cloning vector of the present invention.

<ihc1 Promoter> ihc1 gene is a gene encoding Ihc1 which is a protein having a molecular weight of 15,400. ihc1 gene is widely conserved among fungi including a yeast of the genus *Schizosaccharomyces*.

The expression of Ihc1 protein is suppressed in a low-cell-density state such as the beginning of cell growth, and is induced in a high-cell-density state. The expression of the Ihc1 protein is controlled by the promoter of ihc1 gene. Therefore, the induction of expression by ihc1 promoter is suppressed in a low-cell-density state such as the beginning of cell growth, and the expression is highly inducible in a high-cell-density state. Accordingly, by using this promoter, it becomes possible to prepare an expression vector which enables, in a transformant of a yeast of the genus *Schizosac-*

*charomyces*, the adjustment of the expression of a foreign protein in a cell-density dependent manner.

The ihc1 promoter may be a promoter of ihc1 gene contained in a yeast of the genus *Schizosaccharomyces*, and may also be a promoter derived from any yeast of the genus *Schizosaccharomyces*, but is preferably ihc1 promoter of *S. pombe* which is more widely used.

The ihc1 gene of *S. pombe* is publicly known, and the systematic name of ihc1 gene registered in a gene sequence database of *S. pombe* (*S. pombe* Gene DB; HyperText Markup Language://WorldWideWeb.genedb.org/genedb/pombe/) is SPAC22G7.11c. The ihc1 promoter is a region contained in 1 to 501 bp upstream from the 5' end (A of initiation codon ATG) of an ihc1 gene ORF (SEQ ID NO:9).

The ihc1 promoter to be used for the cloning vector of the present invention may be a promoter of ihc1 gene contained in a yeast of the genus *Schizosaccharomyces*, and may also be a promoter derived from any yeast of the genus *Schizosaccharomyces*. As the yeast of the genus *Schizosaccharomyces*, *S. pombe*, *Schizosaccharomyces japonicus* and *Schizosaccharomyces octosporus* may, for example, be mentioned. Further, the ihc1 promoter used for a cloning vector may be one derived from the same species as, or one derived from a species different from, the yeast of the genus *Schizosaccharomyces* to be introduced with an expression vector prepared from the cloning vector. In the present invention, it is preferred to use ihc1 promoter of *S. pombe* which is more widely used.

The ihc1 promoter is a region comprised of a nucleotide sequence identical to the promoter endogenous to a wild-type yeast of the genus *Schizosaccharomyces* (wild-type ihc1 promoter), or a region which has a promoter activity similar to the wild-type ihc1 promoter and is comprised of the nucleotide sequence having deletion, substitution or addition of at least one amino acid, preferably from one to tens amino acids, more preferably from one to dozen amino acids, further preferably from one to nine amino acids, even further preferably from one to few amino acids.

Further, the ihc1 promoter to be used for the cloning vector of the present invention may be a region which has a promoter activity similar to the wild-type ihc1 promoter and is comprised of an amino acid sequence having a homology to a nucleotide sequence identical to the wild-type ihc1 promoter of at least 80%, preferably at least 85%, more preferably at least 90%, further preferably at least 95%.

The ihc1 promoter of *S. pombe* is a region contained in 1 to 501 bp upstream from the 5' end (A of initiation codon ATG) of an ihc1 gene ORF (SEQ ID NO:9). The nucleotide sequence of the region is shown as SEQ ID NO:9. That is, the cloning vector of the present invention preferably contains a region comprised of a nucleotide sequence represented by SEQ ID NO:9. Further, a region which has a promoter activity similar to the wild-type hsp1 promoter and is comprised of a nucleotide sequence represented by SEQ ID NO:9 having deletion, substitution or addition of at least one amino acid, preferably from one to tens amino acids, more preferably from one to dozen amino acids, further preferably from one to nine amino acids, even further preferably from one to few amino acids, or a nucleotide sequence having a homology to a sequence represented by SEQ ID NO:9 of at least 80%, preferably at least 85%, more preferably at least 90%, further preferably at least 95%, may also be used suitably as the ihc1 promoter for the cloning vector of the present invention.

<Cloning Vector>

The cloning vector of the present invention has, in addition to the hsp9 promoter or the ihc1 promoter, a cloning site for introducing a foreign structural gene which is located downstream from the promoter and is governed by the promoter, and a terminator capable of functioning in a yeast of the genus *Schizosaccharomyces*.

The cloning site contained in the cloning vector is a restriction enzyme recognition site exists only in the cloning site of the cloning vector. The cloning site contained in the cloning vector of the present invention may have only one restriction enzyme recognition site, or may be a multiple cloning site having at least two restriction enzyme recognition sites. As the multiple cloning site, a multiple cloning site contained in publicly known multiple cloning vectors can be used as it is, and one prepared by appropriately modifying a publicly known multiple cloning site can also be used. In addition, the cloning vector of the present invention may have a stop codon at a downstream end region inside of the cloning site or at the downstream of the cloning site.

As the terminator which functions in a yeast of the genus *Schizosaccharomyces*, a terminator endogenous to the yeast of the genus *Schizosaccharomyces* or a terminator exogenous to the yeasts of the genus *Schizosaccharomyces* can be used. Further, two or more types of terminators may be present in the vector. As the terminator endogenous to a yeast of the genus *Schizosaccharomyces*, an inv1 gene terminator of a yeast of the genus *Schizosaccharomyces* may, for example, be mentioned. Further, as the terminator exogenous to a yeast of the genus *Schizosaccharomyces*, the terminator derived from human disclosed in Patent Document 2, 4 or 10 may, for example, be mentioned, and human lipocortin-1 terminator is preferred.

The cloning vector of the present invention preferably contains a 5'-untranslation region located downstream from the promoter and upstream from the cloning site, and preferably contains a 3'-untranslation region located downstream from the cloning site. Further, the cloning vector of the present invention preferably contains, at the cloning site, a marker for discriminating it from an expression vector having a foreign structural gene introduced therein. As the marker, a drug resistance gene capable of functioning in *E. coli* such as an ampicillin resistance gene may, for example, be mentioned.

Further, the cloning vector of the present invention preferably contains a marker for selecting a transformant. As the marker, an auxotrophic complementation marker such as ura4 gene and isopropyl malate dehydrogenase gene (leu1 gene) may, for example, be mentioned.

The cloning vector of the present invention may further contain, in addition to a region which constitutes an expression cassette when a foreign structural gene is introduced into the cloning site, a DNA region necessary for producing a transformant. For example, in the case of introducing an expression cassette into a chromosome, a recombination region is preferably contained therein. The recombination region described in the first embodiment of the present invention, which is used for introducing the expression cassette of gsf2 vector into a chromosome, may be used as it is for introducing an expression cassette containing a foreign structural gene (not limited to gsf2 gene). Even in the case of an expression vector containing a foreign structural gene other than gsf2 gene, for introducing the expression cassette into a chromosome, the genetic engineering method described in the first embodiment of the present invention may be used as it is.

In the case of preparing a transformant in which the expression cassette of the expression vector produced from the cloning vector of the present invention is maintained in host cells as an extrachromosomal gene, the vector of the present invention is preferably a plasmid which contains a sequence required for replication in yeast of the genus *Schizosaccharomyces*, i.e. Autonomously Replicating Sequence (ARS). Further, in the case of integrating the expression cassette into a chromosome, ARS is preferably eliminated from the expression vector before its introduction into a host.

The cloning vector of the present invention can be produced by replacing a promoter region, which is contained in a publicly known cloning vector to be used for producing the expression vector for expressing a foreign gene in a host, with a hsp9 promoter or ihc1 promoter. For example, it can be produced by replacing the promoter region of a multiple cloning vector, which is disclosed in JP-A-H7-163373, JP-A-H10-234375, JP-A-H11-192094, JP-A-2000-136199 or the like, with a hsp9 promoter or ihc1 promoter.

As specific methods for constructing the cloning vector of the present invention, publicly known methods can be used. For example, an operation method described in the article [J. Sambrook et al., "Molecular Cloning $2^{nd}$ ed.", Cold Spring Harbor Laboratory Press (1989)]. In addition, it may be constructed by an enzymatic amplification method using PCR, a chemical synthesis, or the like.

[Expression Vector and its Production Method]

The expression vector of the second embodiment of the present invention can be produced by introducing a foreign structural gene into a cloning site of the cloning vector of the present invention. The introduction of the foreign structural gene into the cloning site may be carried out by using publicly known methods, like the production of the cloning vector.

The foreign structural gene introduced in the expression vector of the present invention is not particularly limited so long as it is a structural gene encoding a protein, and may be a gene homologous to a gene endogenous to the yeast of the genus *Schizosaccharomyces* host or a structural gene derived from a heterologous organism. From the yeast of the genus *Schizosaccharomyces* transformant obtained by using an expression vector containing a structural gene (e.g. the above-mentioned gsf2 gene) encoding an endogenous protein of a yeast of the genus *Schizosaccharomyces*, a large amount of the endogenous protein can be produced. Further, from the yeast of the genus *Schizosaccharomyces* transformant obtained by using an expression vector containing a structural gene derived from a heterologous organism, a large amount of heterologous proteins can be produced.

The protein encoded by a foreign structural gene introduced into the expression vector of the present invention is preferably a heterologous protein, more preferably a protein produced by multicellular organisms such as animals and plants, especially a protein produced by a mammal (including humans). Such a protein is rarely obtained with high activity if a prokaryotic host microorganism such as *E. coli* is used for its production, and its production efficiency is generally low if an animal cell such as CHO cell is used as a host. These problems can be solved by using the expression vector of the present invention and employing a heterologous protein expression system in which a yeast of the genus *Schizosaccharomyces* is used as a host.

The foreign structural gene introduced in the expression vector of the present invention may be a wild-type structural gene, a gene prepared by modifying a wild-type structural gene, or an artificially synthesized gene, so long as it encodes a protein. As a non-wild-type structural gene, a gene encoding a chimeric protein in which two or more wild-type proteins are fused one another and a gene encoding a protein in which an additional peptide or the like is bound to the N-terminal or C-terminal of a wild-type protein may, for example, be mentioned. As the additional peptide, a signal such as a secretion signal, an organelle localization signal or the like, and a tag such as His-tag or FLAG-tag may, for example, be mentioned. The signal should be a signal which functions in a yeast of the genus *Schizosaccharomyces*. The secretion signal is a peptide introduced at the N-terminal and having a function of secreting the expressed protein out of the host cell. As the secretion signal which functions in a yeast of the genus *Schizosaccharomyces*, P3 signal described in WO1996/23890 is particularly preferred.

[Transformant and its Production Method]

The transformant of the second embodiment of the present invention is characterized by containing the above-described expression vector of the second embodiment of the present invention. The transformant of the second embodiment of the present invention is produced by introducing the above-described expression vector into a yeast of the genus *Schizosaccharomyces*.

The host for the transformant of the second embodiment of the present invention is a yeast of the genus *Schizosaccharomyces*. It may be a wild-type or a mutant-type in which a specific gene is deleted or inactivated depending on application. For deletion or inactivation of a specific gene, publicly known methods can be used. Specifically, the Latour system (Nucleic Acids Res. (2006) 34: e11, and WO2007/063919) can be used to delete the gene. Further, the gene can be inactivated by mutating the gene at a certain position by mutant screening using mutagens (Koubo Bunshi Idengaku Jikken-Hou, 1996, Japan Scientific Societies Press), random mutations using PCR (PCR Methods Appl., 1992, vol. 2, p. 28-33) and the like. As the yeast of the genus *Schizosaccharomyces* host in which a specific gene is deleted or inactivated, ones disclosed in WO2002/101038, WO2007/015470, etc. may be used.

Further, the host is preferably a yeast of the genus *Schizosaccharomyces* having a marker for selecting a transformant. For example, it is preferred to use a host which essentially requires a specific nutrient factor for growth due to deletion of a certain gene. When preparing a transformant by using a vector containing a target gene sequence, a transformant lacking the auxotrophy of the host can be obtained by using a vector carrying the deleted gene (auxotrophic complementation marker). It is possible to select the transformant by using the difference in auxotrophy between the host and the transformant. As the auxotrophic complementation marker, ura4 gene (auxotrophic complementation marker) and isopropyl malate dehydrogenase gene (leu1 gene) may, for example, be mentioned.

As the yeast of the genus *Schizosaccharomyces* host, one belongs to the above-mentioned species may be used. Among the above-described yeasts of the genus *Schizosaccharomyces*, *S. pombe* is preferred in view of the availability of various useful mutant strains. The *S. pombe* strain to be used in the present invention may, for example, be ATCC38399 (leu1-32h−) or ATCC38436 (ura4-294h−), which is available from the American Type Culture Collection.

Further, even in the case of introducing an expression vector containing a foreign structural gene other than β-glucosidase gene, the *S. pombe* mutant of the first embodiment of the present invention may be used as a host.

The yeast of the genus *Schizosaccharomyces* host is transformed by using the above-described expression vector, and as the transformation method, any known transformation method for a yeast of the genus *Schizosaccharomyces* may be used. Such a transformation method may, for example, be a conventional method like a lithium acetate method [K. Okazaki et al., Nucleic Acids Res., 18, 6485-6489 (1990)], electroporation method, spheroplast method, glass-beads method, or the like., and a method disclosed in JP-A-2005-198612. Further, a commercially available yeast transformation kit may be used.

After transformation, the resulting transformants are usually subjected to selection. The selection may, for example, be carried out as follows. Screening is carried out by a culture broth which can select transformants by the above-mentioned auxotrophic marker, and two or more colonies are selected among the obtained colonies. In addition, the copy numbers of a vector and an expression cassette integrated into the chromosomes can be identified by subjecting the selected mutants to a genomic analysis using pulse-field gel electrophoresis.

(Cultivation Method)

The transformant of the second embodiment of the present invention may be cultivated in the same manner as a natural yeast of the genus *Schizosaccharomyces*. As the cultivation method, ones described in the first embodiment of the present invention may be mentioned. Specifically, a nutrient medium such as YPD medium (M. D. Rose et al., "Methods In Yeast Genetics", Cold Spring Harbor Laboratory Press (1990)), a minimal medium such as MB Medium (K. Okazaki et al., Nucleic Acids Res., vol. 18, p. 6485-6489 (1990)) and the like may be used.

Publicly known yeast cultivation methods including a shaking cultivation and a stirring cultivation may, for example, be used.

Further, the cultivation temperature is preferably from 23 to 37° C. Further, the cultivation time may be set appropriately.

Cultivation may be carried by batch culture, fed-batch culture or continuous culture.

[Method for Producing a Foreign Protein]

The method for producing a protein of the second embodiment of the present invention is characterized by cultivating the above-described transformant of the second embodiment of the present invention and, from a cell or a culture supernatant thereby obtained, recovering a protein encoded by the above-described foreign structural gene.

The cultivation conditions can be set appropriately taking into consideration the type, etc. of a foreign protein of interest to be produced. For example, at a temperature of from 16 to 42° C., preferably from 25 to 37° C., and a cultivation time of from 8 to 168 hours, preferably from 48 to 96 hours. Either shaking culture or static culture can be employed, and stirring or aeration may be applied if necessary.

When the transformant of the second embodiment of the present invention is a transformant prepared by introducing an expression vector containing a hsp9 promoter, after cultivating the transformant under a condition where an inductive stimulus such as heat stress is applied thereto, the hsp9 promoter is activated by the stress and the transcription of a foreign structural gene governed by the promoter is promoted, whereby the foreign structural protein is expressed. In the case of cultivating under such an inductive stimulus condition, as compared with the case of cultivating under a normal condition, the growth amount of a yeast of the genus *Schizosaccharomyces* is generally low. Therefore, the cultivation is carried out under a normal condition at the beginning of cultivation, and then an inductive stimulus such as heat stress is applied thereto at the time when the concentration of cells in a culture broth is increased to a certain level. Since the amount of cells is increased by the initial cultivation stage, the cultivation system as a whole produces a large amount of heterologous proteins. Here, heat stress is one of available inductive stimuli, and other inductive stimuli may be used as long as their effects are verified as mentioned above. The inductive stimulus is preferably heat, or addition of cadmium, an osmotic pressure increasing agent, hydrogen peroxide, ethanol or the like.

In the case of heat, the temperature can be increased to the maximum survival temperature of a yeast of the genus *Schizosaccharomyces*. Therefore, the temperature for applying heat stress is a temperature of, preferably from 2 to 20° C., more preferably from 3 to 12° C., most preferably from 4 to 6° C., higher than the original cultivation temperature, and is from 15 to 55° C., preferably from 25 to 45° C., more preferably from 30 to 40° C. The heat stress application time is not particularly restricted, but its effect can be confirmed after at least several minutes, and is preferably from 1 to 29 hours, more preferably from 1 to 15 hours.

In the case of cadmium addition, it is added in the form of cadmium ions. The final cadmium concentration is from 0.1 to 1.5 mM, preferably from 0.5 to 1.0 mM. The cultivation time is preferably at most 5 hours, particularly preferably at most 3 hours.

In the case of an osmotic pressure increasing agent, an osmotic pressure increasing agent such as a high concentration electrolyte or sorbitol is added to increase the osmotic pressure. When using potassium chloride at a high concentration, the final potassium concentration is from 0.1 to 2.0 M, preferably from 0.5 to 1.5 M. The addition time is not particularly limited, but is preferably from 1 to 12 hours, more preferably from 1 to 10 hours.

In the case of hydrogen peroxide, its final concentration is from 0.1 to 1.5 mM, preferably from 0.5 to 1.0 mM. The cultivation time is not particularly limited, but is preferably from 1 to 15 hours, more preferably from 1 to 12 hours.

In the case of ethanol, its final concentration is from 5 to 20 V/V %, preferably from 5 to 15 V/V %. The cultivation time is not particularly limited, but is preferably from 1 to 20 hours, particularly preferably from 1 to 15 hours.

The above-mentioned conditions may be applied alone or in combination of two or more of them. The effect of such a combination can be ascertained easily by comparing the expression amounts.

When the transformant of the second embodiment of the present invention is a transformant prepared by introducing an expression vector containing an ihc1 promoter, after cultivating the transformant in a low-cell-density state such as the beginning of cell growth, no expression or significantly low expression of a foreign protein is observed. That is, in a low-cell-density state, the transformant can grow with no (or little) burden of expressing a foreign protein and can grow more efficiently as compared with a case of growing with the burden, whereby the amount of cells can be increased efficiently. On the other hand, as the cell density increases, the induction of the expression proceeds. As a result, the foreign protein can be produced in a large amount.

At the end of cultivation, cells are ruptured sonically or mechanically to obtain a cell extract containing the foreign protein of interest, whereby the foreign protein can be isolated and purified from the cell extract. Further, in a case where the foreign protein is secreted out of the cells, the foreign protein can be isolated and purified from the culture supernatant. As the isolation and purification method for recovering the produced protein, publicly known methods including a method utilizing difference in solubility such as salting out or solvent precipitation, a method utilizing difference in molecular weight such as dialysis, ultrafiltration or gel electrophoresis, a method utilizing difference in electric charge such as ion-exchange chromatography, a method utilizing specific affinity such as affinity chromatography, a method utilizing difference in hydrophobicity such as reverse phase high performance liquid chromatography, and a method utilizing difference in isoelectric point such as isoelectric focusing may, for example, be mentioned.

The isolated and purified protein can be identified by a publicly known method such as western blotting or an activity measurement method. The structure of the purified protein can be identified by amino acid analysis, amino-terminal analysis, primary structure analysis and the like.

EXAMPLES

Now, the present invention will be described in further detail with reference to Examples and Comparative Examples. However, it should be understood that the present invention is by no means thereby restricted.

[Test Example 1] Expression Vector Preparation 1

A gene sequence was designed based on the peptide sequence of AaBGL1, by replacing the codons with codons highly expressed in *S. pombe* (SEQ ID NO: 2. Hereinafter referred to as AaBGL1 gene). The recognition sequences for KpnI and BspHI were added upstream of the initiation codon. The recognition sequences for XbaI and SacI were added downstream of the stop codon. A plasmid containing these sequences (synthesized by Geneart AG, Regensburg, Germany) was digested with restriction enzymes BspHI and XbaI.

On the other hand, separately therefrom, pSL6lacZ was digested with restriction enzymes AarI and XbaI, and then treated with an alkaline phosphatase. Thereafter, gel electrophoresis was carried out on an agarose gel to isolate the digested fragment of vector pSL6 and the digested fragment of AaBGL1 gene from the agarose gel, and then these fragments were ligated to each other. The ligated product was introduced into *E. coli* DH5α (Takara Bio, Inc.) to obtain a transformant. From the obtained transformant, a vector was prepared to obtain expression vector pSL6AaBGL1 (FIG. 1, refer to SEQ ID NO: 3). The obtained expression vector was confirmed to be a desired vector by restriction enzyme mapping.

Figure 2:
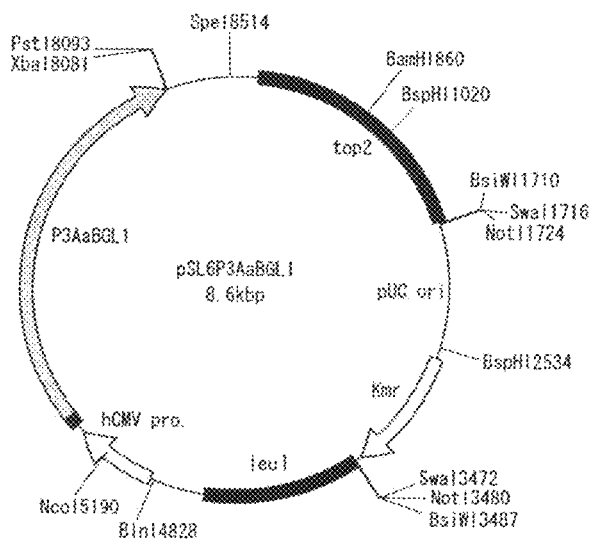
FIG. 2 is a construction map of expression vector pSL6P3AaBGL1.

Further, to prepare AaBGL1 to which secretion signal P3 is attached at the N-terminal, a fragment of AaBGL1 gene was amplified by PCR method with In-fusion primers and pSL6AaBGL1 as template. On the other hand, pSL6P3lacZ was digested with restriction enzymes AR and XbaI. The digested fragments and the PCR-amplified product of the AaBGL1 gene fragment were circularized by In-fusion method, and then introduced into *E. coli* DH5α (Takara Bio, Inc.) to obtain a transformant. From the obtained transformant, a vector was prepared to obtain a desired expression vector pSL6P3AaBGL1 (FIG. 2, refer to SEQ ID NO: 4). The obtained expression vector was confirmed to be a desired vector by restriction enzyme mapping and partial nucleotide sequencing.

[Test Example 2] Expression Vector Preparation 2

Figure 3:
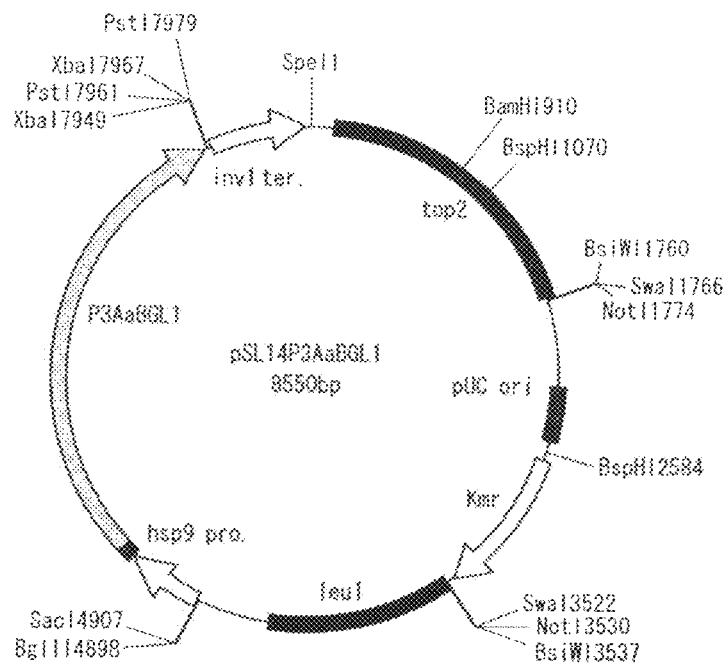
FIG. 3 is a construction map of expression vector pSL14P3AaBGL1.

Further, to prepare AaBGL1 expression vector using a hsp9 promoter, a fragment of pSL6P3AaBGL1 gene was amplified by PCR method with In-fusion primers and pSL6P3AaBGL1 as template. On the other hand, the below-described pSL14lacZ containing a hsp9 promoter was digested with restriction enzymes AarI and XbaI. The digested fragments and the PCR-amplified product of the P3AaBGL1 gene fragment were circularized by In-fusion method, and then introduced into *E. coli* DH5α to obtain a transformant. From the obtained transformant, a vector was prepared to obtain a desired expression vector pSL14P3AaBGL1 (FIG. 3, refer to SEQ ID NO: 5). The obtained expression vector was confirmed to be a desired vector by restriction enzyme mapping and partial nucleotide sequencing.

<Preparation of Multiple Cloning Vector>

Figure 24:
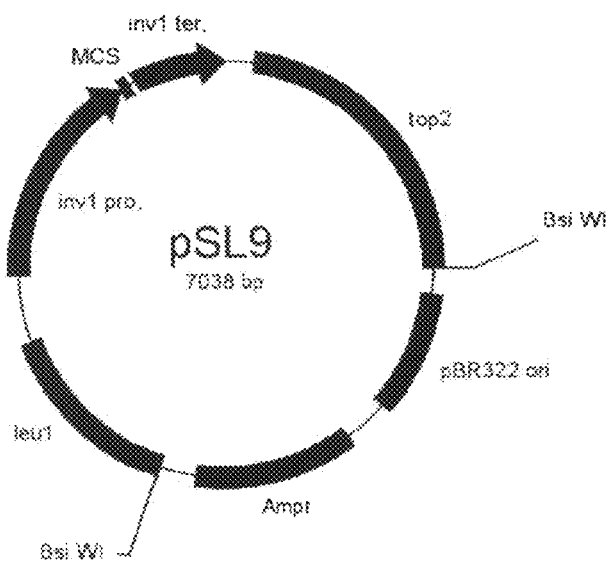
FIG. 24 is a construction map of multiple cloning vector pSL9.
Figure 25:
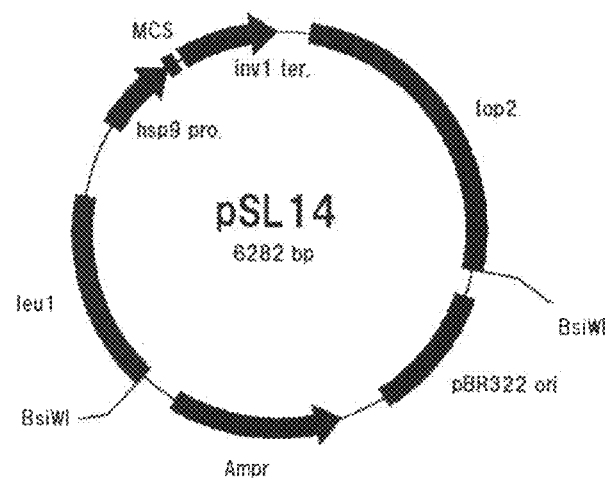
FIG. 25 is a construction map of multiple cloning vector pSL14.

The promoter region ("inv1 pro." in FIG. 24) of multiple cloning vector pSL9 (FIG. 24, 7,038 bp) was replaced with a hsp9 promoter of *S. pombe* (SEQ ID NO: 6) to prepare multiple cloning vector pSL14 (FIG. 25, 6,282 bp).

Specifically, at first, a region 1 to 400 bp (SEQ ID NO: 6) upstream from the 5' end (A of initiation codon ATG) of the ORF of *S. pombe* hsp9 gene was amplified by using genomic DNA derived from a wild-type strain of *S. pombe* (ARC032 strain, corresponds to ATCC38366, 972h⁻) as a template, a forward primer comprising the restriction enzyme recognition site for SacI at the 5' end, and a reverse primer comprising the restriction enzyme recognition site for PciI at the 5' end, thereby to obtain a fragment having the restriction enzyme recognition site for SacI at the 5' end and the restriction enzyme recognition site for PciI at the 3' end.

The promoter portion of pSL9 was subjected to double digestion with restriction enzymes AarI and SalI, followed by ligation for transforming *E. coli* DH5α. After extracting a plasmid, its nucleotide sequences was identified. As a result, the obtained plasmid was found to contain a promoter region having a nucleotide sequence represented by SEQ ID NO: 6, while the sequence has one additional adenine at its 3' end. Thus obtained plasmid was named as pSL14.

Figure 26:
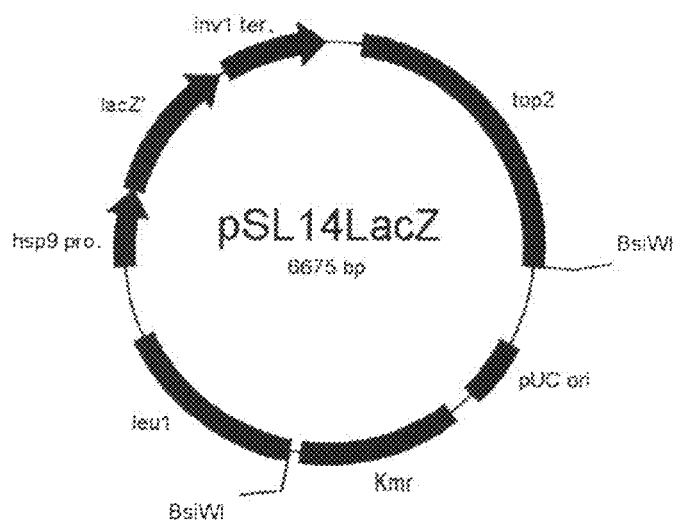
FIG. 26 is a construction map of multiple cloning vector pSL14lacZ.

Then, the region including an ampicillin resistance gene and pBR322ori of pSL14 was replaced with a region including a kanamycin resistance gene and pUCori, and a structural gene encoding lacZ' was integrated into the cloning site, whereby multiple cloning vector pSL14lacZ (FIG. 26, 6,657 bp, refer to SEQ ID NO: 7).

[Test Example 3] Preparation of a Transformant (Transformation of Fission Yeast)

As the host cell, a leucine-auxotrophic strain of *S. pombe* (Genotype: h–, leu1-32, provided from professor Yuichi Iino, Molecular Genetics Research Laboratory, Graduate School of Science, The University of Tokyo) (ATCC38399) was cultivated in YES medium (0.5% of yeast extract, 3% of glucose and 0.1 mg/ml of SP supplements) until $0.6 \times 10^7$ cells/ml. The cells were collected and washed, and then suspended by 0.1M lithium acetate (pH 5.0) to $1.0 \times 10^8$ cells/ml. Thereafter, to 100 µl of the suspension, 1 µg of the above-obtained vector pSL14P3AaBGL1 digested by restriction enzyme SwaI was added, and then 290 µl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 µl of sterile water. The suspension was applied on a minimal-agarose medium. Three days after cultivation, a transformant (AaBGL1 expression strain) was obtained. Thus obtained transformant was named as ASP3660 strain (hereinafter also referred to as normal strain).

[Test Example 4] Preparation of ΔPvg1 Strain
(Pvg1 Gene Deletion Strain)

As the host cell, a uracil-auxotrophic strain of *S. pombe* (ARC010 strain, Genotype: h⁻leu1-32 ura4-D18, provided from professor Yuichi Iino, Molecular Genetics Research Laboratory, Graduate School of Science, The University of Tokyo) was transformed in accordance with the Latour system (Nucleic Acids Res. (2006) 34: e11, and WO2007/063919) to prepare Δpvg1 strain in which pvg1 gene was deleted. Thus obtained mutant was cultivated and subjected to genomic analysis with pulse-field gel electrophoresis, thereby to confirm that pvg1 gene was deleted.

The preparation of a deletion fragment was carried out by a PCR method using whole genomic DNA obtained with DNeasy (manufactured by QIAGEN) from a wild-type strain ARC032 of *S. pombe* (Genotype: h⁻, provided from professor Yuichi Iino, Molecular Genetics Research Laboratory, Graduate School of Science, The University of Tokyo) as the template.

Specifically, a deletion fragment was divided into UP region, OL region and DN region, and DNA fragments of these regions were prepared by a PCR method of using KOD-Dash (manufactured by Toyobo Co. Ltd.), and then full-length deletion fragments were prepared by a similar PCR method using the fragments as templates.

[Test Example 5] Preparation of Δpvg1gsf2⁺ Strain
(Pvg1 Gene Deletion+Gsf2 Expression Increase Strain)

The above-described Δpvg1 strain was cultivated in YES medium (0.5% of yeast extract, 3% of glucose and 0.1 mg/ml of SP supplements) until $0.6 \times 10^7$ cells/ml. The cells were collected and washed, and then suspended by 0.1 M lithium acetate (pH 5.0) to $1.0 \times 10^8$ cells/ml. Thereafter, to 100 μl of the suspension, 1 μg of the below-described gene fragment (SEQ ID NO: 8) containing an ihc1 promoter and gsf2 gene was added, and then 290 μl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 μl of sterile water. The suspension was applied on a minimal-agarose medium containing leucine. Three days after cultivation, a transformant (pvg1 gene deletion+gsf2 expression increase strain) was obtained. FOA treatment was carried out to make it auxotrophic for uracil again. Thus obtained mutant was named as IGF799 strain.

The above-described gene fragment containing an ihc1 promoter and gsf2 gene was prepared as follows. At first, a sequence containing an ihc1 promoter (SEQ ID NO: 9), a gsf2 promoter sequence and a Ura4 sequence at the 5' end side of the ihc1 promoter, and a gsf2-ORF at the 3' end side was prepared as a template, and then amplified by PCR to obtain the above-mentioned gene fragment.

[Test Example 6] Preparation of a Transformant
(Transformation of a Non-Sexual Flocculation Fission Yeast)

As the host cell, the above-described IGF799 strain of *S. pombe* which exhibits non-sexual flocculation was cultivated in YES medium (0.5% of yeast extract, 3% of glucose and 0.1 mg/ml of SP supplements) until $0.6 \times 10^7$ cells/ml. The cells were collected and washed, and then suspended by 0.1 M lithium acetate (pH 5.0) to $1.0 \times 10^8$ cells/ml. Thereafter, to 100 μl of the suspension, 1 μg of the above-obtained vector pSL14P3AaBGL1 digested by restriction enzyme SwaI was added, and then 290 μl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 μl of sterile water. The suspension was applied on a minimal-agarose medium containing uracil. Three days after cultivation, a transformant (AaBGL1 expression strain) was obtained. Thus obtained transformant was named as ASP4106 strain.

[Test Example 7] Preparation of a Transformant
(Uracil-Auxotrophy Complementation)

Figure 4:
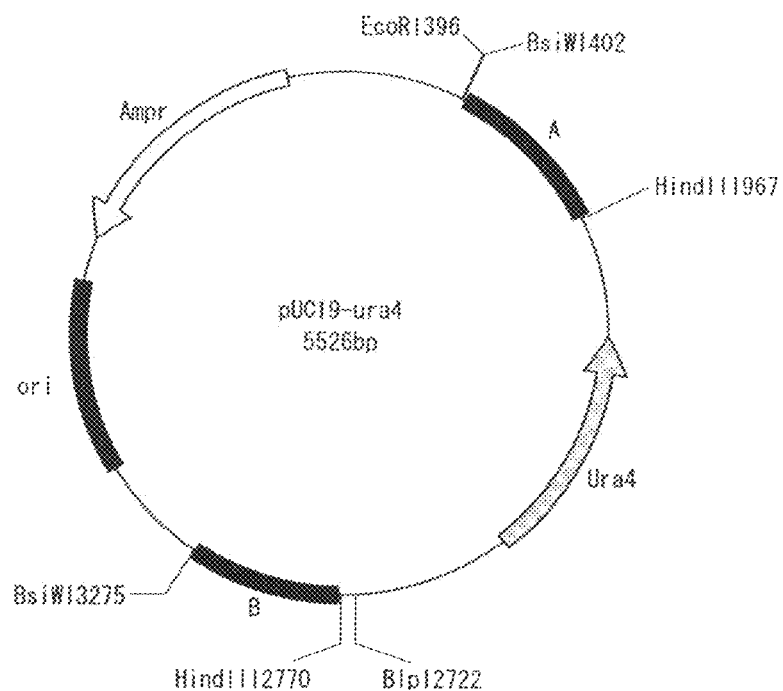
FIG. 4 is a construction map of expression vector pUC19-ura4.

The above-prepared ASP4106 strain was cultivated in YES medium (0.5% of yeast extract, 3% of glucose and 0.1 mg/ml of SP supplements) until $0.6 \times 10^7$ cells/ml. The cells were collected and washed, and then suspended by 0.1 M lithium acetate (pH 5.0) to $1.0 \times 10^8$ cells/ml. Thereafter, to 100 μl of the suspension, 1 μg of pUC19-ura4 (FIG. 4, refer to SEQ ID NO: 10) vector digested by restriction enzyme BsiwI was added, and then 290 μl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 μl of sterile water. The suspension was applied on a minimal-agarose medium. In FIG. 4, the sequences of A and B indicate the recombination regions of the vector. Three days after cultivation, a transformant was obtained. Thus obtained transformant lacking the uracil-auxotrophy of ASP4106 strain was named as ASP4150 strain (hereinafter also referred to as flocculation strain).

[Test Example 8] Batch Culture of a Transformant

The above-obtained AaBGL1 expression strains (normal strain and flocculation strain) were cultivated in YES medium by a test tube for 24 hours at 32° C. 2 ml of the culture broth was transferred to 50 ml of YPD medium (1% of yeast extract, 2% of peptone, and 2% of glucose), and then cultivated by a 500 ml Erlenmeyer flask for 48 hours at 32° C.

To evaluate the cell growth of the transformant, the absorbance of a culture broth at OD660 nm was measured by a spectrophotometer (Spectrophotometer U-1500). In a case where the concentration of the culture broth is high, dilution with RO (Reverse Osmosis) water was carried out for the measurement. In the case of measuring the OD660 of the flocculation strain, before the measurement, suspension with 100 mM to 500 mM EDTA was carried out for deflocculation.

Figure 5:
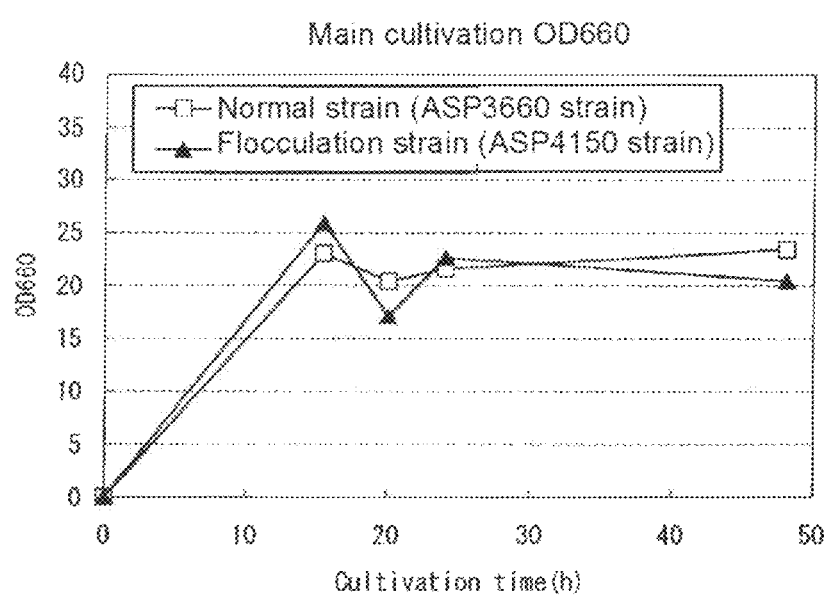
FIG. 5 is a graph showing the cell growth (OD660 values) of a normal strain or a flocculation strain in Test Example 8.

The results of the cell growth are shown in FIG. 5. Comparing the normal strain and the flocculation strain, the time-course changes in the OD660 values during the cultivation were generally similar, and the final OD660 values of the normal strain and the flocculation strain were found to be 23.4 and 20.3, respectively.

The concentration of residual glucose or a metabolite thereof, ethanol, in the culture broth was measured by a biosensor BF5. The collected culture broth was transferred to an Eppendorf tube, and a culture supernatant was obtained by centrifugation using a high-speed microcentrifuge. 300 μl of the culture supernatant was transferred to a BF5 sampling cup, and then the cup was placed in BF5 autosampler which had already been adjusted for the measurement.

BF5 was operated under the following biosensor operation conditions for the analysis.
Equipment: Biosensor BF5 (Oji Scientific Instruments)
Flow rate: 1.0 mL/min
Injection volume: 5 μL
Thermostatic bath temperature: 37° C.
Measurement time: 90 seconds
Concentration determination method: Hydrogen peroxide generated by enzymatic degradation of glucose and ethanol was detected, and calculated based on the peak height of a standard solution.

Figure 6:
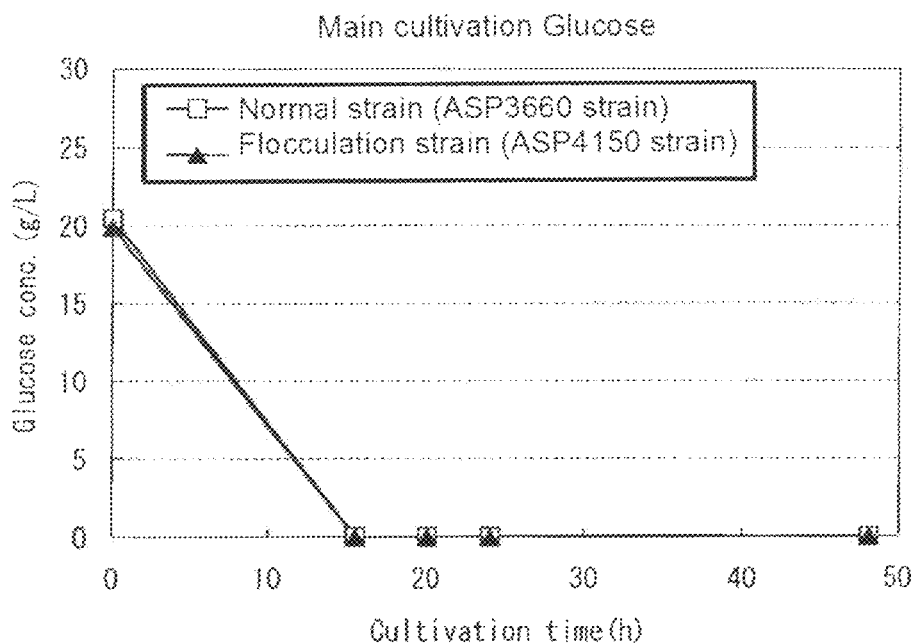
FIG. 6 (*a*) is a graph showing the glucose concentration of a culture broth for a normal strain or a flocculation strain in Test Example 8.
Figure 6:
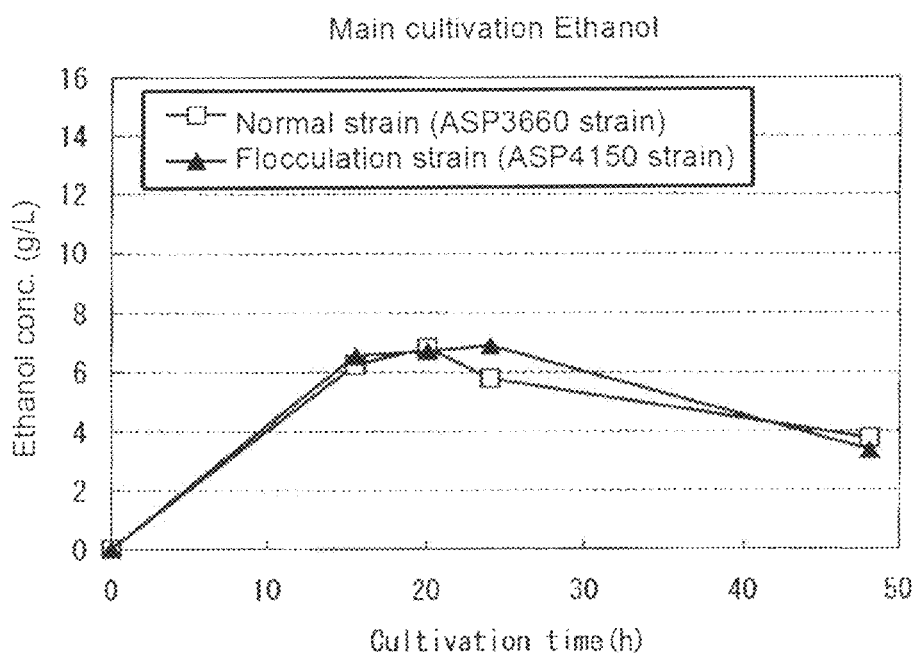

The concentration of residual glucose in the culture broth was shown in FIG. 6 (a) and the concentration of ethanol, a metabolite of glucose, was shown in FIG. 6 (b). Comparing the normal strain and the flocculation strain, the time-course changes in each of the glucose concentration and the ethanol concentration during the cultivation were generally similar.

Comparing the normal strain and the flocculation strain, the time-course changes in each of the OD660 value, the glucose concentration and the ethanol concentration during the cultivation were generally similar. From this, it can be assumed that the glucose metabolism and the cell growth proceeded at approximately the same rate in the normal strain and the flocculation strain by cultivating them under identical conditions. It seems that the cell-growth properties were less affected by the genetic engineering operation for imparting a flocculation property.

[Test Example 9] Confirmation of AaBGL1 Expression by Activity Measurement

By using the above-obtained culture supernatant of the AaBGL1 expression strain, a diluted enzyme sample was prepared, and then the activity was measured in accordance with the following method.
(Activity Measurement Method)
To 10 μl of 20 mM p-nitrophenyl-P-D-glucoside (hereinafter abbreviated as pNPG), 10 μl of 1M sodium acetate buffer solution (pH 4.5) and 130 μl of water were added, and then 50 μl of the diluted enzyme sample was introduced for reacting them at 37° C. for 10 minutes. 100 μl of the reaction mixture was mixed with 100 μl of 2% sodium carbonate solution to terminate reaction, and then the amount of free p-nitrophenol was colorimetrically measured at a wavelength of 450 nm.

The amount of enzyme that produces 1 μmol of p-nitrophenol per minute was defined as 1 U. The pNPG degradation activity (hereinafter also referred to as pNPG activity) per 1 ml of the normal strain or flocculation strain culture supernatant was shown in FIG. 7.

Figure 7:
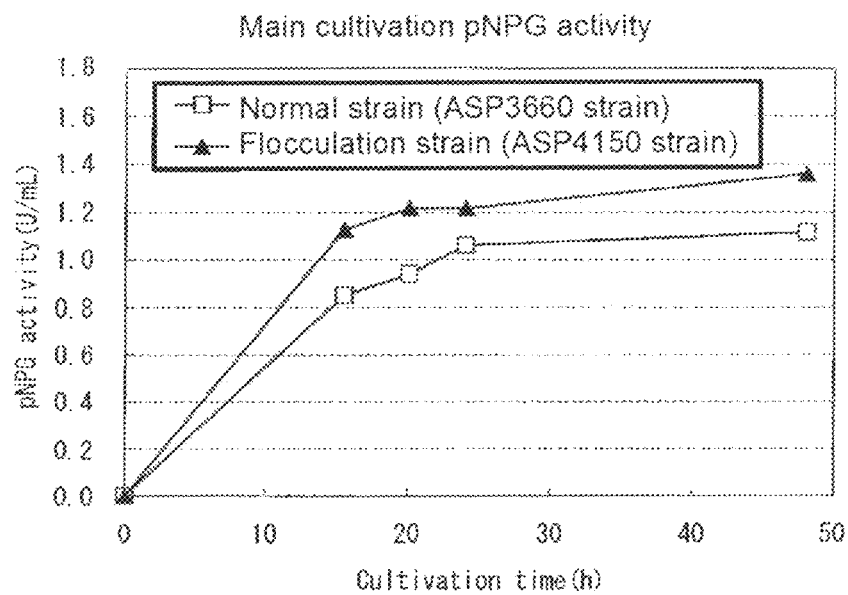
FIG. 7 is a graph showing the pNPG degradation activity of an AaBGL1 of a normal strain or a flocculation strain in Test Example 9.

As shown in FIG. 7, the flocculation strain showed an activity value 1.38 times higher than that of the normal strain after cultivating for 15.5 hours and immediately after the depletion of glucose, and showed an activity value 1.27 times higher than that of the normal strain after cultivating for 48 hours.

[Test Example 10] Fed-Batch Culture of a Transformant

The normal strain or the flocculation strain was inoculated in 5 ml of YES medium, and then subjected to pre-culture 1 in a test tube for 24 hours at 32° C. Further, to 200 ml of YES medium, 4 ml of the culture broth obtained by pre-culture 1 was added, and then pre-culture 2 was carried out in a 1 L Sakaguchi flask for 24 hours at 30° C.

Thereafter, by using a 5 L jar fermenter, the culture broth obtained by pre-culture 2 was added into 1,800 ml of an initial culture medium having the composition shown in Table 1, followed by cultivation at 30° C. Here, the concentration of each component in Table 1 indicates the concentration after the inoculation of pre-culture 2. 14.0 hours after starting the cultivation, upon ascertaining that the concentration of residual glucose in the culture broth was lower than 1.0 g/L, feeding was started. The feeding was continued for 81 hours, and 1,450 ml of a feed medium having the composition of Table 2 was added into the jar fermenter, thereby to cultivate for 95 hours (a cultivation time after starting the cultivation) at 30° C. The pH was maintained at 4.5 by controlling the addition of 12.5% ammonia water.

TABLE 1

| Component | Concentration |
|---|---|
| Yeast extract | 10 g/L |
| Glucose (hydrous) | 33 g/L |
| $(NH_4)_2SO_4$ | 15 g/L |
| $KH_2PO_4$ | 8 g/L |
| $MgSO_4 \cdot 7H_2O$ | 5.34 g/L |
| $Na_2HPO_4$ | 0.04 g/L |
| $CaCl_2 \cdot 2H_2O$ | 0.2 g/L |
| Choline chloride | 15.00 mg/L |
| Folic acid | 0.08 mg/L |
| Pyridoxine | 2.16 mg/L |
| Thiamine | 26.49 mg/L |
| Thymidine | 8.75 mg/L |
| Riboflavin sodium phosphate | 7.97 mg/L |
| p-aminobenzoic acid | 38.16 mg/L |
| Pantothenic acid Ca | 15.70 mg/L |
| Nicotinic acid | 49.00 mg/L |
| Inositol | 27.00 mg/L |
| Biotin | 0.08 mg/L |
| $FeC_6H_5O_7 \cdot nH_2O$ | 28.40 mg/L |
| $ZnSO_4 \cdot 7H_2O$ | 25.40 mg/L |
| $MnCl_2 \cdot 4H_2O$ | 4.10 mg/L |
| $CuSO_4 \cdot 5H_2O$ | 3.80 mg/L |
| $H_3BO_3$ | 2.90 mg/L |
| $Na_2MoO_4 \cdot 2H_2O$ | 0.68 mg/L |
| KI | 0.20 mg/L |
| $NiSO_4 \cdot 6H_2O$ | 0.44 mg/L |
| $CoCl_2 \cdot 6H_2O$ | 0.40 mg/L |

(moisture content of glucose: 8.8%)

TABLE 2

| Component | Concentration |
|---|---|
| Yeast extract | 10 g/L |
| Glucose (hydrous) | 550 g/L |
| $CaCl_2 \cdot 2H_2O$ | 0.20 g/L |
| $KH_2PO_4$ | 9.00 g/L |
| $MgSO_4 \; 7H_2O$ | 4.45 g/L |
| $K_2SO_4$ | 3.50 g/L |
| $Na_2SO_4$ | 0.14 g/L |
| $Na_2HPO_4$ | 0.04 g/L |
| Choline chloride | 15.00 mg/L |
| Folic acid | 0.08 mg/L |
| Pyridoxine | 2.16 mg/L |
| Thiamine | 26.49 mg/L |
| Thymidine | 8.75 mg/L |
| Riboflavin sodium phosphate | 7.97 mg/L |
| p-aminobenzoic acid | 38.16 mg/L |
| Pantothenic acid Ca | 82.37 mg/L |
| Nicotinic acid | 715.70 mg/L |
| Inositol | 693.70 mg/L |
| Biotin | 0.74 mg/L |

TABLE 2-continued

| Component | Concentration |
| --- | --- |
| $FeC_6H_5O_7 \cdot nH_2O$ | 473.4 mg/L |
| $ZnSO_4 \cdot 7H_2O$ | 423.4 mg/L |
| $MnCl_2 \cdot 4H_2O$ | 68.4 mg/L |
| $CuSO_4 \cdot 5H_2O$ | 63.4 mg/L |
| $H_3BO_3$ | 48.4 mg/L |
| $Na_2MoO_4 \cdot 2H_2O$ | 11.4 mg/L |
| KI | 3.4 mg/L |
| $NiSO_4 \cdot 6H_2O$ | 7.4 mg/L |
| $CoCl_2 \cdot 6H_2O$ | 6.7 mg/L |

(moisture content of glucose: 8.8%)

To evaluate the cell growth of the transformant, the absorbance of a culture broth at OD660 nm was measured by a spectrophotometer (Spectrophotometer U-1500). In a case where the concentration of the culture broth is high, dilution with RO water was carried out for the measurement. In the case of measuring the OD660 nm of the flocculation strain, before the measurement, suspension with 100 mM to 500 mM EDTA was carried out for deflocculation.

Figure 8:
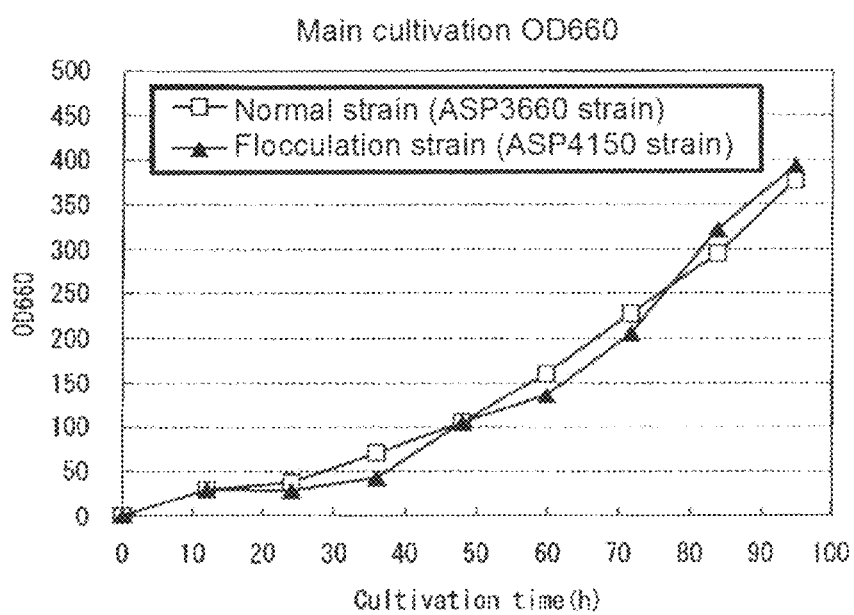
FIG. 8 is a graph showing the cell growth (OD660 values) of a normal strain or a flocculation strain in Test Example 10.

The results of the cell growth are shown in FIG. 8. Comparing the normal strain and the flocculation strain, the time-course changes in the OD660 values during the cultivation were generally similar, and the final OD660 values of the normal strain and the flocculation strain were found to be 376 and 395, respectively. By using a semi-synthetic culture broth prepared by adding Yeast Extract derived from natural sources into a synthetic culture broth, the high cell concentrations were achieved.

The concentration of residual glucose or a metabolite thereof, ethanol, in the culture broth was measured in the same manner as in Test Example 8.

Figure 9:
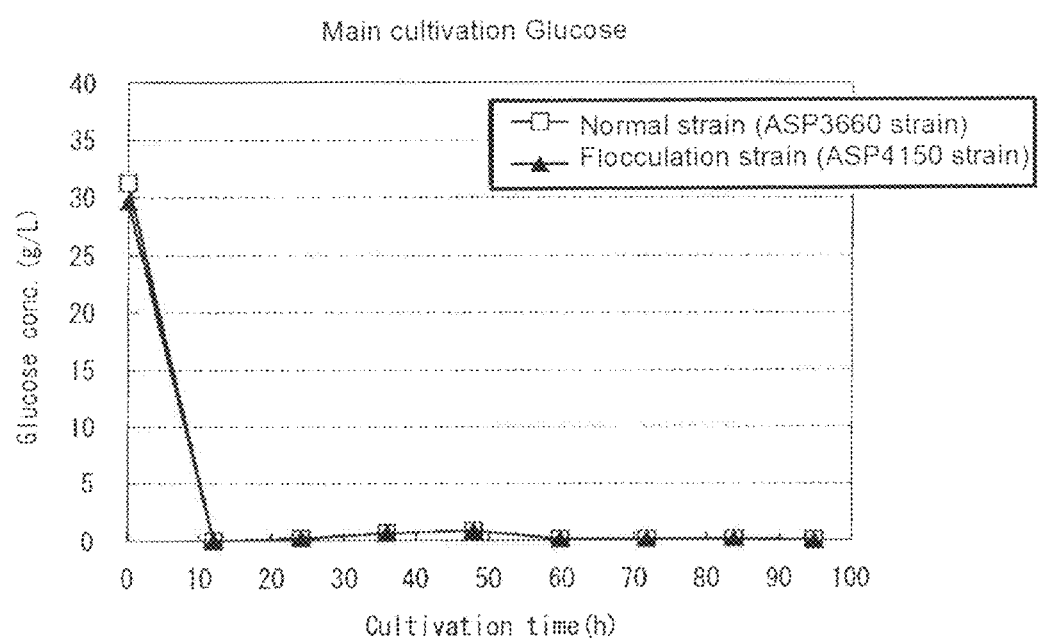
FIG. 9 (*a*) is a graph showing the glucose concentration of a culture broth for a normal strain or a flocculation strain in Test Example 10.
Figure 9:
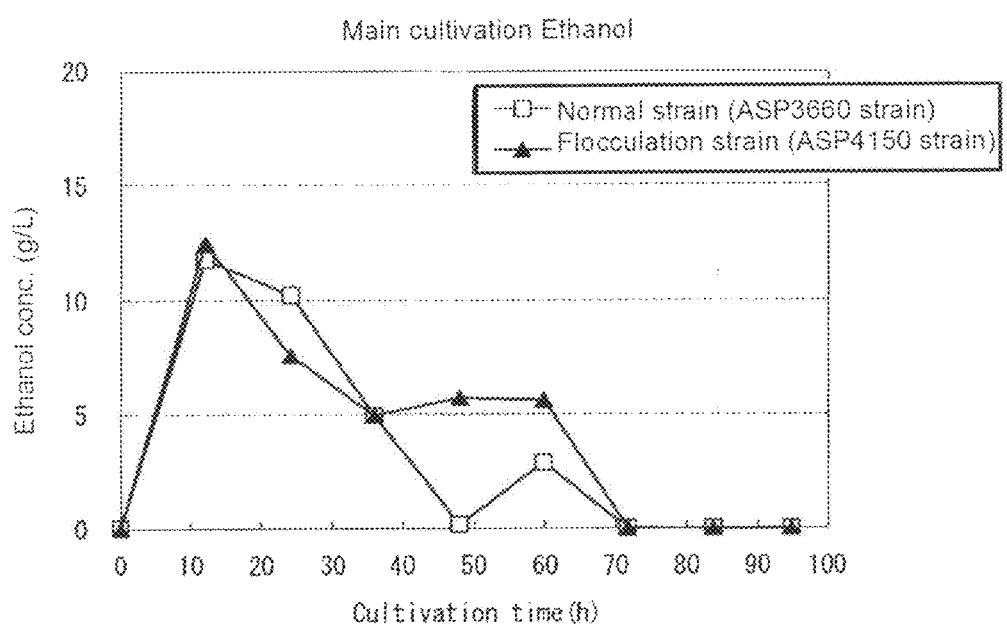

The concentration of residual glucose in the culture broth was shown in FIG. 9 (a) and the concentration of ethanol, a metabolite of glucose, was shown in FIG. 9 (b). Comparing the normal strain and the flocculation strain, the time-course changes in each of the glucose concentration and the ethanol concentration during the cultivation were generally similar. The glucose concentration remained at a low value of 1 g/L or lower after starting feeding. The ethanol concentration of the culture broth finally remained at a low value of 1 g/L or lower, since ethanol generated at the batch culture stage decreased gradually after starting feeding. After starting feeding, until the end of the fed-batch culture, a glucose effect which triggers an ethanol production phase was not observed.

Comparing the normal strain and the flocculation strain, the time-course changes in each of the OD660 value, the glucose concentration and the ethanol concentration during the cultivation were generally similar. From this, it can be assumed that the glucose metabolism and the cell growth proceeded at approximately the same rate in the normal strain and the flocculation strain by cultivating them under identical conditions. It seems that the cell-growth properties were less affected by the genetic engineering operation for imparting a flocculation property.

[Test Example 11] Measurement of a Sedimentation Rate

Each 1 L of the samples obtained at the end of fed-batch culture in Test Example 10 was transferred to a 1 L graduated cylinder, thereby to compare the sedimentation rate. The cells in each graduated cylinder were suspended sufficiently, and the graduated cylinder was allowed to stand still to start sedimentation. The distance between the liquid surface and the solid-liquid interface (interface between the sedimented yeast cells and the supernatant) was divided by the time elapsed from the onset of sedimentation, thereby to calculate the sedimentation rate. The results are shown in FIG. 10.

Figure 10:
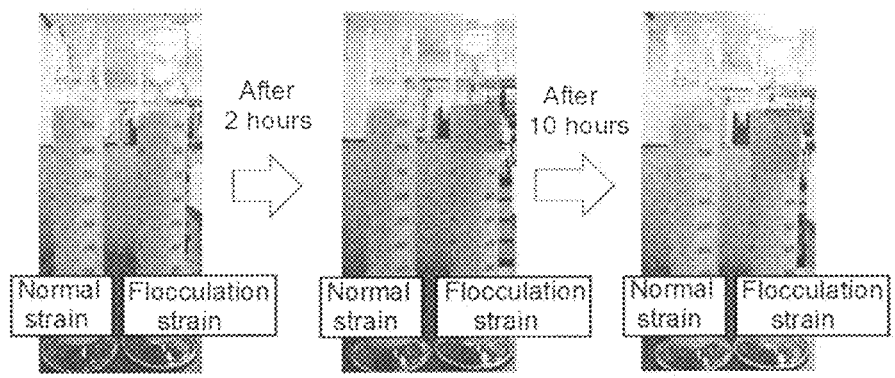
FIG. 10 is a photograph illustrating a sedimentation status of a normal strain or a flocculation strain in Test Example 11.

As shown in FIG. 10, the sedimentation of the flocculation strain was found to be high as compared with the normal strain. The sedimentation rate of the flocculation strain was 30 mm/h at the time of 2 hours after starting the sedimentation, and was 6.7 mm/h at the time of additional 10 hours (12 hours after starting the sedimentation). On the other hand, the sedimentation rate of the normal strain was 1.5 mm/h at the time of 12 hours after starting the sedimentation.

Figure 11:
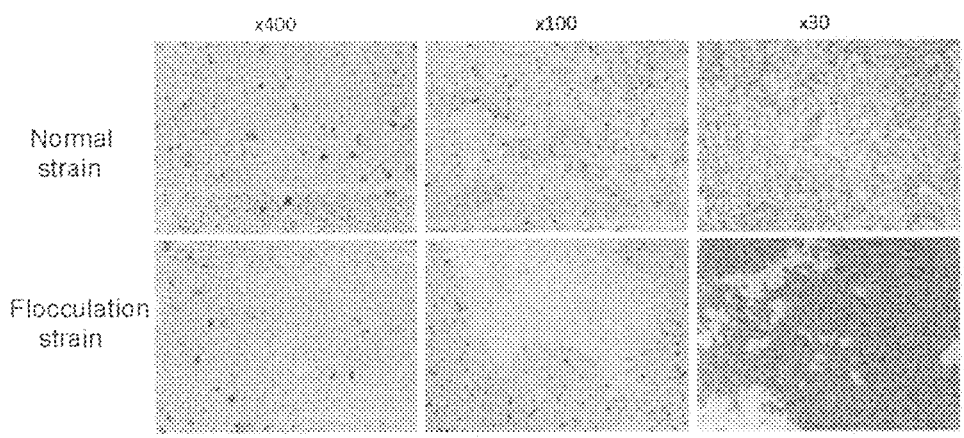
FIG. 11 is a photograph illustrating microscopic observation results of a normal strain or a flocculation strain in Test Example 11.

Further, the results of a microscopic observation (results of trypan blue staining) of the samples obtained at the end of fed-batch culture are shown in FIG. 11. As shown in FIG. 11, from the microscopic observation results of the sample at the end of fed-batch culture, clustering and aggregation of the cells were confirmed in the flocculation strain, disappearance of a flocculation property after fed-batch culture was not observed. In the normal strain, the cells were not aggregated, and were found to be dispersed.

[Test Example 12] Optimization of a Cultivation Temperature (Fed-Batch Culture)

The normal strain (ASP3660 strain) was inoculated in 5 ml of YES medium, and then subjected to pre-culture 1 in a L-shaped test tube for 24 hours at 30° C. Further, to 120 ml of YES medium, 2.4 ml of the culture broth obtained by pre-culture 1 was added, and then pre-culture 2 was carried out in a 500 mL Sakaguchi flask for 24 hours at 30° C.

Thereafter, by using a 3 L jar fermenter, the culture broth obtained by pre-culture 2 was added into 1,080 ml of an initial culture medium, thereby to start cultivation. Cultivation was carried out by using two culture tanks and applying two different temperature conditions of 30° C. and 34° C. As the initial culture medium, a medium prepared by removing Yeast Extract, choline chloride, folic acid, pyridoxine, thiamine, thymidine, riboflavin sodium phosphate and p-aminobenzoic acid from the composition of Table 1 was used. Here, the concentration of each component in Table 1 indicates the concentration after the inoculation of pre-culture 2. 11.8 hours after starting the cultivation, feeding was started. The feeding was continued for 84.2 hours, and 685 ml of a feed medium was added into the jar fermenter, thereby to cultivate for 96 hours (a cultivation time after starting the cultivation) at 30° C. or at 34° C. As the feed medium, a medium prepared by removing Yeast Extract, choline chloride, folic acid, pyridoxine, thiamine, thymidine, riboflavin sodium phosphate and p-aminobenzoic acid from the composition of Table 2 was used. The pH was maintained at 4.5 by controlling the addition of 12.5% ammonia water.

Figure 12:
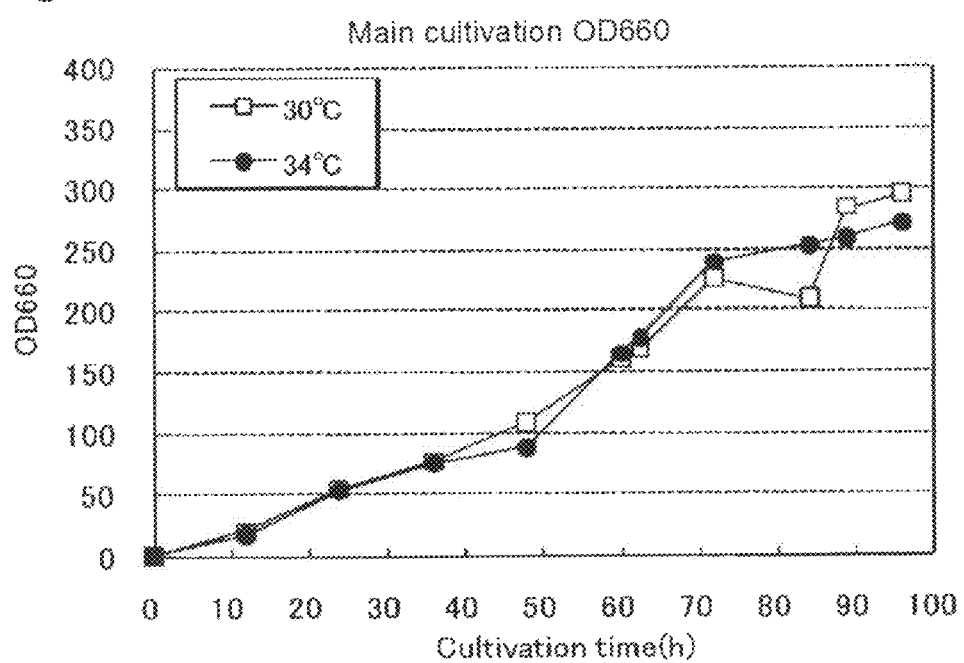
FIG. 12 is a graph showing the cell growth (OD660 values) at 30° C. or 34° C. in Test Example 12.

To evaluate the cell growth of the transformant, the OD660 nm value of the culture broth was measured in the same manner as in Test Example 8. The cell growth results are shown in FIG. 12. Comparing the 30° C. condition and the 34° C. condition, the time-course changes in the OD660 values of culture broths were generally similar. The final OD660 values in the 30° C. condition and the 34° C. condition were respectively found to be 295 and 271, whereby the high cell concentrations were achieved.

Figure 13:
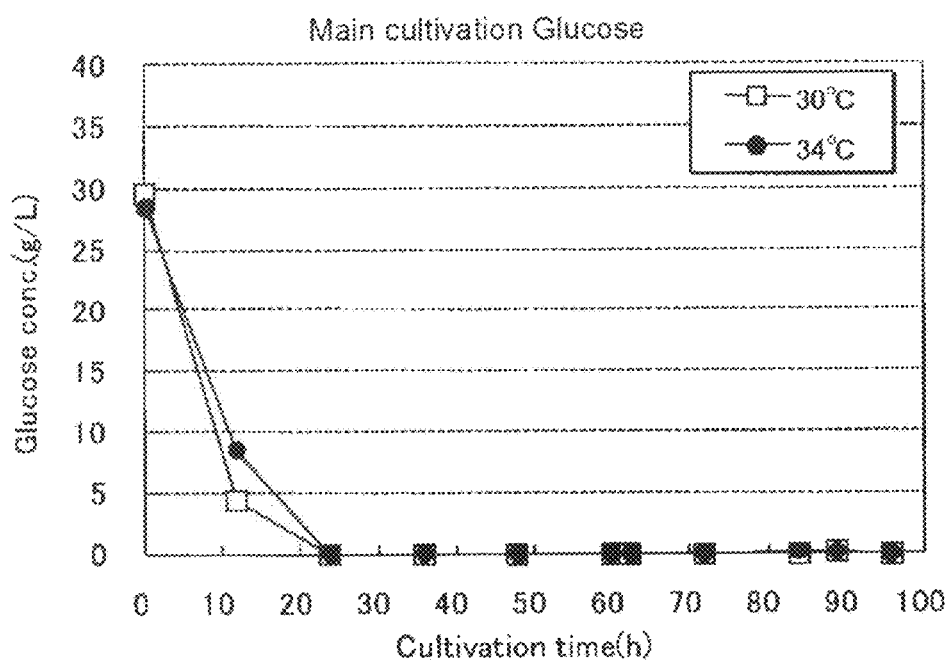
FIG. 13A is a graph showing the glucose concentration of a culture broth at 30° C. or 34° C. in Test Example 12.
FIG. 13B is a graph showing the ethanol concentration of a culture broth at 30° C. or 34° C. in Test Example 12.
Figure 13:
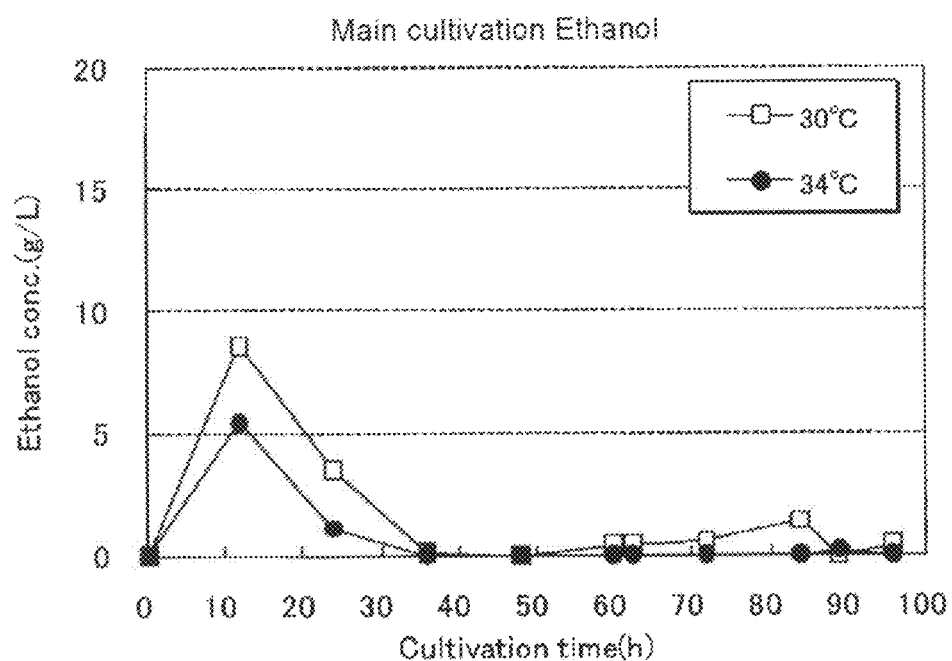

The concentration of residual glucose or a metabolite thereof, ethanol, in the culture broth was measured in the same manner as in Test Example 8. The concentration of residual glucose in the culture broth was shown in FIG. 13A and the concentration of ethanol, a metabolite of glucose, was shown in FIG. 13B. Comparing the 30° C. condition and the 34° C. condition, the time-course changes in each of the glucose concentration and the ethanol concentration during the cultivation were generally similar. The glucose concentration remained at a low value of 1 g/L or lower after cultivating 24 hours. The ethanol concentration of the culture broth finally remained at a low value of 2 g/L or lower, since ethanol generated at the batch culture stage decreased gradually after starting feeding.

Figure 14:
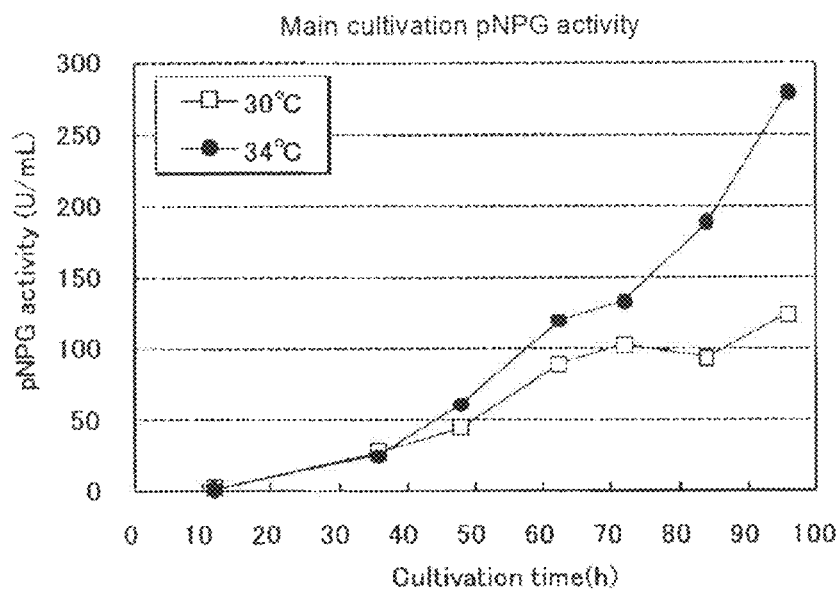
FIG. 14 is a graph showing the pNPG degradation activity of an AaBGL1 at 30° C. or 34° C. in Test Example 12.

The pNPG degradation activity of the culture broth was measured in the same manner as in Test Example 9. The pNPG degradation activity per 1 ml of the culture supernatant in the 30° C. condition or the 34° C. condition was shown in FIG. 14. In terms of a pNPG activity value, the 34° C. condition showed an activity value 2.26 times higher than that of the 30° C. condition at the end of cultivation after cultivating for 96 hours.

[Test Example 13] Confirmation of AaBGL1 Expression by SDS-PAGE Analysis

Figure 15:
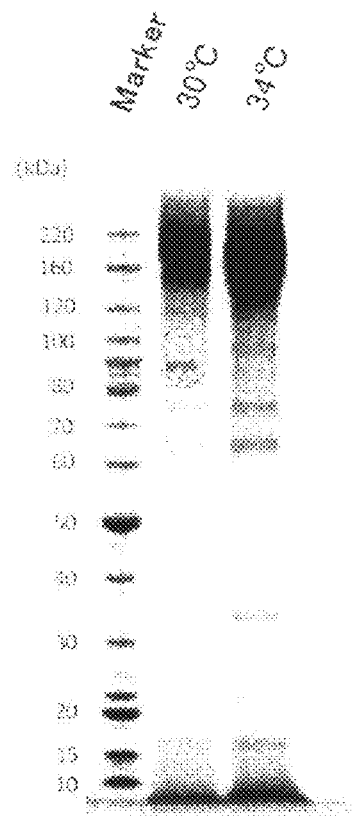
FIG. 15 is a graph showing the results of SDS-PAGE of Test Example 13.

Each 5 µl of the culture supernatant samples obtained at end of fed-batch culture in Test Example 12 was dissolved in a SDS-PAGE sample buffer, and SDS-PAGE was carried out with a 4 to 12% acrylamide gel, followed by staining with Coomassie brilliant blue. The results are shown in FIG. 15. From the results of SDS-PAGE, at end of cultivation after cultivating for 96 hours, in the 34° C. condition, the intensity of an AaBGL1 band at a molecular weight of 120 kDa or larger was more intense than the case of the 30° C. condition, whereby the increase in the secretory expression amount of AaBGL1 was observed. Addition of a saccharide chain to AaBGL1 resulted in the detection of smear bands.

[Test Example 14] Protein Production by Hsp9 Promoter

Figure 16:
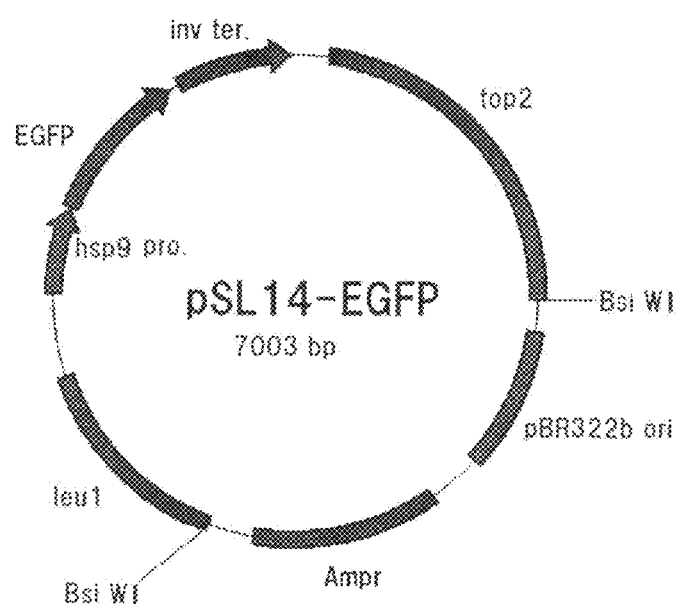
FIG. 16 is a construction map of expression vector pSL14-EGFP.

<Preparation of an Expression Vector>
By a PCR method using In-fusion primers and pEGFP-N1 (manufactured by CLONTECH) containing GFP gene as a template, an ORF fragment of EGFP gene was amplified. On the other hand, pSL14 was subjected to double digestion with restriction enzymes AflII and XbaI. The digested fragment and the ORF fragment of EGFP gene amplified by PCR were circularized by In-fusion method, and then introduced into *E. coli* DH5α (Takara Bio, Inc.) to obtain a transformant. From the obtained transformant, a vector was prepared to obtain a desire expression vector pSL14-EGFP (FIG. 16). The obtained expression vector was confirmed to be a desired vector by restriction enzyme mapping and partial nucleotide sequencing.

Figure 17:
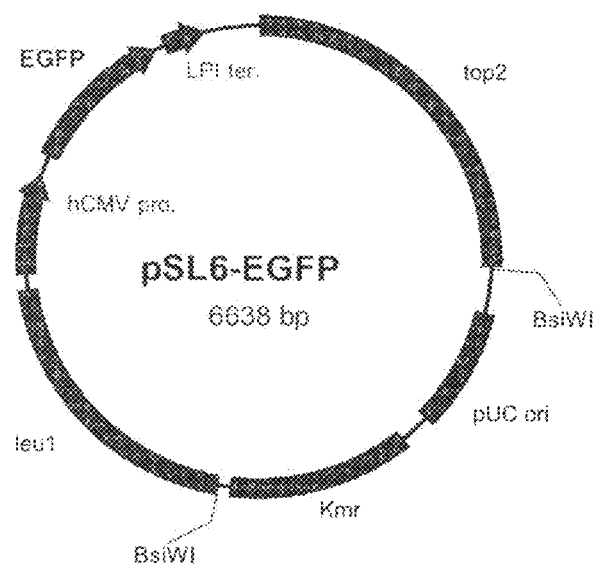
FIG. 17 is a construction map of expression vector pSL6-EGFP.

In the same manner, pSL6-EGFP vector (FIG. 17) was prepared by integrating the ORF fragment of EGFP into pSL6, and was used as a control.
<Preparation of a Transformant>
As the host cell, a leucine-auxotrophic strain of *Schizosaccharomyces pombe* (Genotype: h⁻, leu1-32, provided from professor Yuichi Iino, Molecular Genetics Research Laboratory, Graduate School of Science, The University of Tokyo) (ATCC38399) was cultivated in YES medium (0.5% of yeast extract, 3% of glucose and 0.1 mg/ml of SP supplements) until $0.6 \times 10^7$ cells/ml. The cells were collected and washed, and then suspended by 0.1M lithium acetate (pH 5.0) to $1.0 \times 10^8$ cells/ml. Thereafter, to 100 µl of the suspension, 1 µg of the above-obtained expression vector pSL14-EGFP digested by restriction enzyme NotI was added, and then 290 µl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 µl of sterile water. The suspension was applied on a minimal-agarose medium.

The transformant obtained three days after cultivation was named as ASP3395 strain.

In the same manner, pSL14-EGFP was introduced to obtain a transformant SL14E strain, and pSL6-EGFP was introduced to obtain a transformant SL6E strain.
<EGFP Expression>
The obtained ASP3395 strain was inoculated in 5 ml of YES medium contained in a test tube, and cultivated for 70 hours at 32° C. At the end of cultivation, the fluorescence intensity of the culture broth excited at 488 nm was measured.

As controls, SL14E strain and SL6E strain were cultivated under the same condition, and the florescence intensities of the culture broths at the end of cultivation were measured.

Figure 18:
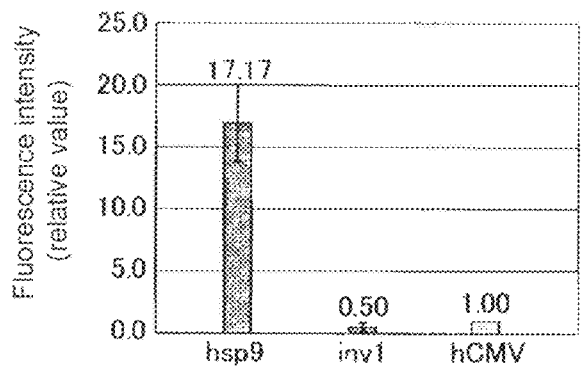
FIG. 18 is a graph showing the results of measuring the fluorescence intensity (relative value obtained by taking the fluorescence intensity of a SL6E strain culture broth as 1) of each culture broth in Test Example 14.

The measurement results are shown in FIG. 18. As a result, the fluorescence intensity (relative value) of SL14E strain was found to be only 0.50, when the fluorescence intensity of SL6E strain was taken as 1, but the fluorescence intensity (relative value) of ASP3395 strain was found to be 17.17, and was significantly high.

The fluorescence intensity of a culture broth is an index for the expression amount of fluorescent protein EGFP. Since the expression efficiency of a hsp9 promoter in a yeast of the genus *Schizosaccharomyces* is significantly high, it is apparent that the transformant obtained by using the expression vector of the present invention can produce a much larger amount of a foreign protein than the case of using other promoters.

[Test Example 15] Protein Production by Ihc1 Promoter

Figure 19:
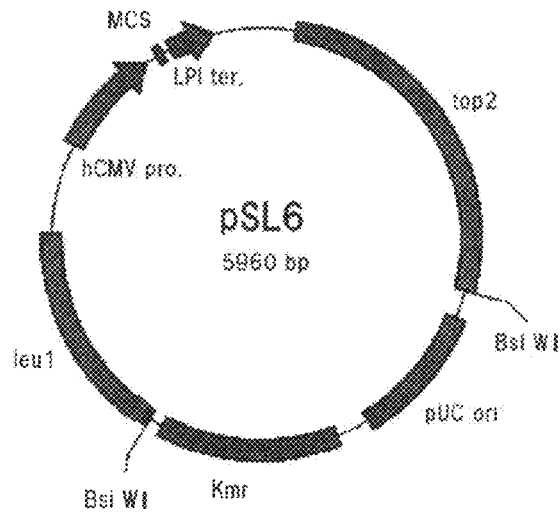
FIG. 19 is a construction map of multiple cloning vector pSL6.
Figure 20:
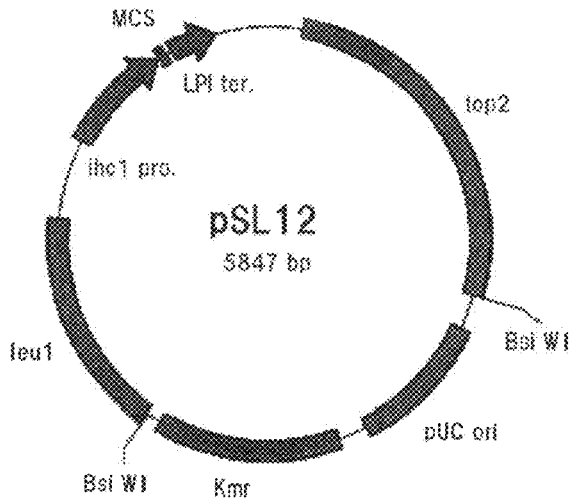
FIG. 20 is a construction map of multiple cloning vector pSL12.

<Preparation of a Multiple Cloning Vector>
Single-locus integration type recombination vector pSL17 was prepared by the following steps. Firstly, the hCMV promoter region of publicly known integration type multiple cloning vector pSL6 for fission yeast (FIG. 19, 5,960 bp, SEQ ID NO: 11) was replaced with the promoter of *S. pombe* ihc1 gene (ihc1 promoter), thereby to prepare multiple cloning vector pSL12 (FIG. 20, 5,847 bp).

Specifically, at first, a region 1 to 501 bp (SEQ ID NO: 9) upstream from the 5' end (A of initiation codon ATG) of the ORF of *S. pombe* ihc1 gene was amplified by using genomic DNA derived from a wild-type strain of *S. pombe* (ARC032 strain, corresponds to ATCC38366, 972h) as a template, a forward primer (ihc1-promoter-F: Table 3) comprising the restriction enzyme recognition site for BlnI at the 5' end, and a reverse primer (ihc1-promoter-R: Table 3) comprising the restriction enzyme recognition site for KpnI at the 5' end, thereby to obtain a fragment (ihc1 promoter fragment) having the restriction enzyme recognition site for BlnI at the 5' end and the restriction enzyme recognition site for KpnI at the 3' end.

Into a fragment prepared by double digestion of pSL9 with restriction enzymes BlnI and KpnI, a fragment prepared by double digestion of the ihc1 promoter fragment with restriction enzymes BlnI and KpnI was integrated by ligation, thereby to obtain integration type vector pSL12 for fission yeast (SEQ ID NO:14).

Figure 21:
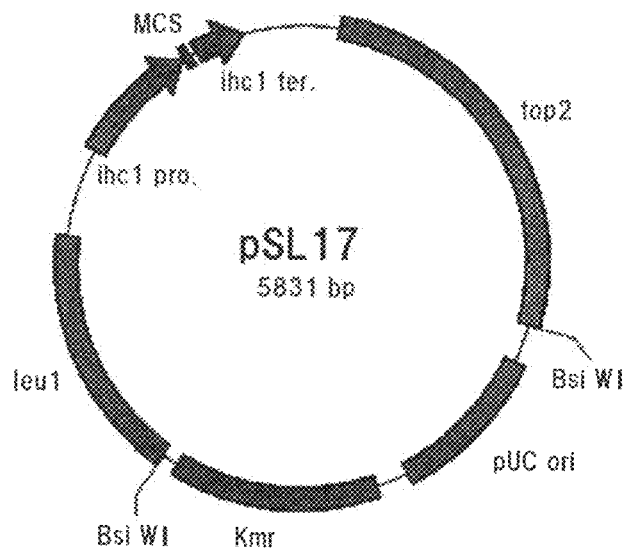
FIG. 21 is a construction map of multiple cloning vector pSL17.

Then, the LPI terminator region of pSL12 was replaced with the terminator of *S. pombe* ihc1 gene (ihc1 terminator), thereby to prepare multiple cloning vector pSL17 (FIG. 21, 5,831 bp).

Specifically, at first, a region 1 to 200 bp (SEQ ID NO: 15) downstream from the 3' end (the third letter of stop codon) of the ORF of *S. pombe* ihc1 gene was amplified by using genomic DNA derived from a wild-type strain of *S. pombe* (ARC032 strain, corresponds to ATCC38366, 972h$^-$) as a template and In-fusion primers (ihc1-terminator-F and ihc1-terminator-R: Table 3), thereby to obtain a fragment having the ihc terminator region (ihc terminator fragment).

By using pSL12 as a template, PCR amplification was carried out with In-fusion primers (pSL12-F and pSL12-R: Table 3) to obtain a pSL12 full-length fragment lacking the LPI terminator region. Then, into thus obtained fragment, the ihc terminator fragment was integrated by using In-fusion cloning kit (product name: In-Fusion HD Cloning Kit w/Cloning Enhancer, Takara Bio Inc.), thereby to prepare multiple cloning vector pSL17 (SEQ ID NO: 20).

TABLE 3

| | Sequence | SEQ ID NO. |
|---|---|---|
| ihc1-promoter-F | 5'-AATTCCTAGGGGCTTCAACTAGCTCGGGAT-3' | 12 |
| ihc1-promoter-R | 5'-AATTGGTACCGACACCTGCTTCACATTGTTT ATAAATAAAATTGGAGTT-3' | 13 |
| ihc1-terminator-F | 5'-CCTGCAGGCATGCAAGCTTATTGCTGCCCAG TTGATTACCC-3' | 16 |
| ihc1-terminator-R | 5'-GAAACGCGCGAGGCAGATCATTGTATGCTAT GGGGTGTCGAC-3' | 17 |
| pSL12-F | 5'-GTCGACACCCCATAGCATACAATGATCTGCC TCGCGCGTTTC-3' | 18 |
| pSL12-R | 5'-GGGTAATCAACTGGGCAGCAATAAGCTTGCA TGCCTGCAGG-3' | 19 |

<Preparation of an Expression Vector>

Figure 22:
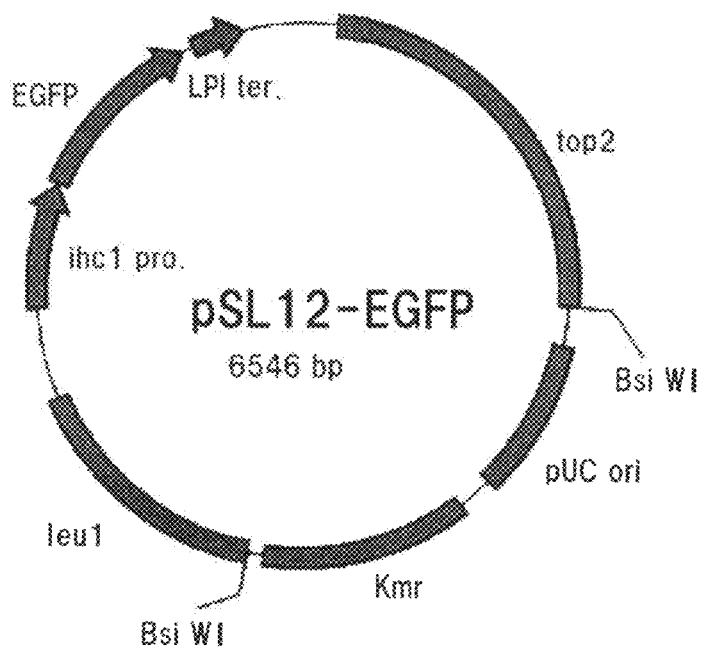
FIG. 22 is a construction map of expression vector pSL12-EGFP.

By a PCR method using In-fusion primers and pEGFP-N1 (manufactured by CLONTECH) containing GFP gene as a template, an ORF fragment of EGFP gene was amplified. On the other hand, the above-described pSL12 was subjected to double digestion with restriction enzymes AflII and XbaI. The digested fragment and the ORF fragment of EGFP gene amplified by PCR were circularized by In-fusion method, and then introduced into *E. coli* DH5α (Takara Bio, Inc.) to obtain a transformant. From the obtained transformant, a vector was prepared to obtain a desired expression vector pSL12-EGFP (FIG. 22). The obtained expression vector was confirmed to be a desired vector by restriction enzyme mapping and partial nucleotide sequencing.

In the same manner, pSL6-EGFP vector (FIG. 17) was prepared by integrating the ORF fragment of EGFP into pSL6, and was used as a control.

<Preparation of a Transformant>

As the host cell, a leucine-auxotrophic strain of *Schizosaccharomyces pombe* (Genotype: h$^-$, leu1-32, provided from professor Yuichi Iino, Molecular Genetics Research Laboratory, Graduate School of Science, The University of Tokyo) (ATCC38399) was cultivated in YES medium (0.5% of yeast extract, 3% of glucose and 0.1 mg/ml of SP supplements) until $0.6 \times 10^7$ cells/ml. The cells were collected and washed, and then suspended by 0.1M lithium acetate (pH 5.0) to $1.0 \times 10^8$ cells/ml. Thereafter, to 100 μl of the suspension, 1 μg of the above-obtained expression vector pSL12-EGFP digested by restriction enzyme NotI was added, and then 290 μl of a 50% (w/v) polyethylene glycol (PEG4000) aqueous solution was added thereto, followed by stirring to incubate them for 60 minutes at 30° C., 5 minutes at 42° C., and 10 minutes at room temperature, in this order. PEG4000 was removed by centrifugation and then the cells were washed to suspend them in 150 μl of sterile water. The suspension was applied on a minimal-agarose medium.

The transformant obtained three days after cultivation was named as 277G strain.

In the same manner, pSL6-EGFP was introduced to obtain a transformant of SL6E strain.

<EGFP Expression>

The obtained 277G strain was inoculated in 5 ml of YES medium contained in a test tube, and cultivated for 72 hours at 32° C. From the start to the end of cultivation, the fluorescence intensity excited at 488 nm and the absorbance at 660 nm of the culture broth were measured over time.

As a control, SL6E strain was cultivated under the same condition, and the florescence intensity and the absorbance at 660 nm of the culture broth were measured over time.

Figure 23:
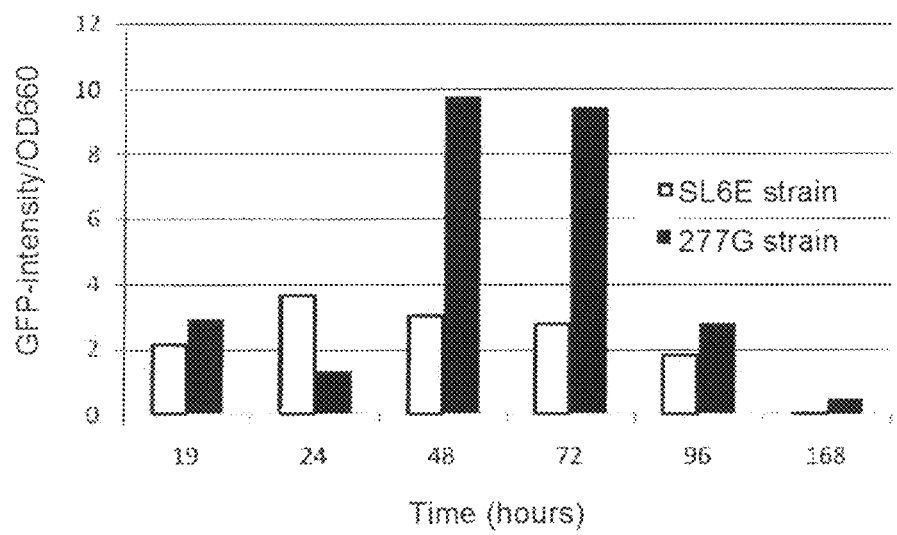
FIG. 23 is a graph showing the results of measuring the time-course changes in [fluorescence intensity/$OD_{600}$] of each culture broth in Test Example 15.

The time-course changes in [fluorescence-intensity/OD$_{600}$] (a value obtained after dividing the fluorescence intensity by the observance at 600 nm) of the culture broth of each strain are shown in FIG. 23. As a result, the [fluorescence-intensity/ODD$_{600}$] of 277G strain ("ihc1p" in Figure) was found to be lower than that of SL6E strain using hCMV promoter ("hCMVp" in Figure) at the time of 24 hours after cultivation, but was found to be higher than that of SL6E strain after cultivating 48 hours, whereby the EGFP expression amount per single cell was found to be high.

This application is a continuation of PCT Application No. PCT/JP2013/072195, filed on Aug. 20, 2013, which is based upon and claims the benefit of priority from Japanese Patent Application No. 2012-181865 filed on Aug. 20, 2012. The contents of those applications are incorporated herein by reference in its entirety.

What is claimed is:

1. A cloning vector comprising the nucleotide sequence of SEQ ID NO: 9 comprising a SPAC22G7.11c gene promoter and a heterologous nucleic acid sequence, wherein the heterologous nucleic acid sequence comprises a cloning site located downstream from the promoter and a terminator capable of functioning in a yeast of the genus *Schizosaccharomyces*, wherein the promoter is capable of regulating expression of a heterologous gene introduced into the cloning site.

2. A method for producing an expression vector, comprising introducing a heterologous gene into the cloning site of the cloning vector of claim 1.

3. An expression vector comprising the cloning vector of claim 1 further comprising a heterologous gene which is introduced into the cloning site.

4. A method comprising introducing the expression vector of claim 3 into a yeast of the genus *Schizosaccharomyces*.

5. A transformant of a yeast of the genus *Schizosaccharomyces*, wherein the transformant comprises the expression vector of claim 3.

6. A method comprising cultivating the transformant of claim 5, expressing a protein encoded by the heterologous gene, and recovering the protein.

* * * * *